United States Patent
Reguera et al.

(10) Patent No.: US 9,601,227 B2
(45) Date of Patent: *Mar. 21, 2017

(54) MICROBIAL NANOWIRES AND METHODS OF MAKING AND USING

(71) Applicant: BOARD OF TRUSTEES OF MICHIGAN STATE UNIVERSITY, East Lansing, MI (US)

(72) Inventors: Gemma Reguera, East Lansing, MI (US); Dena Cologgi, Edmonton (CA); Robert Mark Worden, Holt, MI (US); Angelines A. Castro-Forero, St. Paul, MN (US); Rebecca Steidl, Williamson, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 267 days.

This patent is subject to a terminal disclaimer.

(21) Appl. No.: 14/193,943

(22) Filed: Feb. 28, 2014

(65) Prior Publication Data

US 2014/0239237 A1 Aug. 28, 2014

Related U.S. Application Data

(63) Continuation-in-part of application No. PCT/US2012/053221, filed on Aug. 30, 2012.

(60) Provisional application No. 61/558,091, filed on Nov. 10, 2011, provisional application No. 61/530,708, filed on Sep. 2, 2011.

(51) Int. Cl.
| | |
|---|---|
| C07K 14/00 | (2006.01) |
| H01B 1/12 | (2006.01) |
| B82Y 5/00 | (2011.01) |
| C07K 14/195 | (2006.01) |
| C12N 1/20 | (2006.01) |

(52) U.S. Cl.
CPC ............... H01B 1/12 (2013.01); B82Y 5/00 (2013.01); C07K 14/195 (2013.01); C12N 1/20 (2013.01); C07K 2319/20 (2013.01); Y02P 20/134 (2015.11)

(58) Field of Classification Search
None
See application file for complete search history.

(56) References Cited

U.S. PATENT DOCUMENTS

| | | | |
|---|---|---|---|
| 5,418,140 A | 5/1995 | Chang et al. | |
| 5,834,247 A | 11/1998 | Comb et al. | |
| 5,968,769 A | 10/1999 | Green et al. | |
| 6,897,285 B2 | 5/2005 | Xu et al. | |
| 6,984,505 B2 | 1/2006 | Xu et al. | |
| 6,987,007 B2 | 1/2006 | Xu et al. | |
| 7,001,745 B1 | 2/2006 | Xu et al. | |
| 7,060,465 B2 | 6/2006 | Xu et al. | |
| 7,271,256 B2 | 9/2007 | Evans et al. | |
| 7,498,155 B2 | 3/2009 | Lovley et al. | |
| 7,517,671 B2 | 4/2009 | Taron et al. | |
| 7,732,565 B2 | 6/2010 | Taron et al. | |
| 8,729,233 B2 | 5/2014 | Reguera et al. | |
| 8,846,890 B2 | 9/2014 | Reguera et al. | |
| 2003/0216550 A1 | 11/2003 | Xu et al. | |
| 2005/0196804 A1 | 9/2005 | Xu et al. | |
| 2005/0196841 A1 | 9/2005 | Xu et al. | |
| 2006/0030008 A1 | 2/2006 | Xu et al. | |
| 2006/0035333 A1 | 2/2006 | Taron et al. | |
| 2006/0199225 A1 | 9/2006 | Colussi et al. | |
| 2007/0065880 A1 | 3/2007 | Taron et al. | |
| 2007/0099234 A1 | 5/2007 | Zhang et al. | |
| 2010/0167942 A1 | 7/2010 | Zheng et al. | |
| 2011/0071280 A1 | 3/2011 | Taron et al. | |
| 2011/0097737 A1 | 4/2011 | Samuelson et al. | |
| 2012/0053319 A1 | 3/2012 | Reguera et al. | |
| 2012/0053320 A1 | 3/2012 | Reguera et al. | |
| 2014/0336357 A1 | 11/2014 | Reguera et al. | |

FOREIGN PATENT DOCUMENTS

| | | |
|---|---|---|
| EP | 0036776 A2 | 9/1981 |
| JP | 2010-33344 A | 2/1998 |
| WO | 01/57183 A2 | 8/2001 |
| WO | 03/074660 A2 | 9/2003 |
| WO | 2006/041849 A2 | 4/2006 |
| WO | 2006/096821 A1 | 9/2006 |
| WO | 2009/026089 A1 | 2/2009 |
| WO | 2013/033456 A2 | 3/2013 |
| WO | 2013/033456 A3 | 4/2013 |

OTHER PUBLICATIONS

Final Office Action received for U.S. Appl. No. 14/448,843, mailed on Oct. 22, 2015, 6 pages.
Restriction Requirement received for U.S. Appl. No. 14/448,843, mailed on Apr. 6, 2015, 6 pages.
Non Final Office Action received for U.S. Appl. No. 14/448,843, mailed on Jun. 24, 2015, 21 pages.
Advisory Action received for U.S. Appl. No. 14/448,843, mailed on Jan. 8, 2016, 4 pages.
Lovley et al.. "Novel Mode of Microbial Energy Metabolism: Organic Carbon Oxidation Coupled to Dissimilatory Reduction of Iron or Manganese", Applied and Environmental Microbiology, vol. 54, No. 6, Jun. 1988, pp. 1472-1480.
Lovley et al., "Rapidly Growing Rumen Methanogenic Organism that Synthesizes Coenzyme M and has a High Affinity for Formate", Applied and Environmental Microbology, vol. 48, No. 1, Jul. 1984, pp. 81-87.
Lucas et al., "Pilin [Geobacter sp. M21]", Accession No. YP_003021449.1, 2009, 1 page.
Lucas et al., "Pilin Domain-Containing Protein [Geobacter lovleyi SZ]", Accession No. YP_001952332.1. 2008, 1 page.

(Continued)

Primary Examiner — Anand Desai

(57) ABSTRACT

Electrically conductive nanowires, and genetically or chemically modified production and use of such nanowires with altered conductive, adhesive, coupling or other properties are described. The disclosed nanowires are used as device or device components or may be adapted for soluble metal remediation.

15 Claims, 29 Drawing Sheets

(56) References Cited

OTHER PUBLICATIONS

Lutz et al., "Independent and Tight Regulation of Transcriptional Units in *Escherichia coli* via the LacR/O, the TetR/O and AraC/I1-I2 Regulatory Elements", Nucleic Acids Research, vol. 25, No. 6, Mar. 1997, pp. 1203-1210.

Malhotra, Arun, "Tagging for Protein Expression", Chapter 16, Methods in Enzymology,vol. 463, 2009, pp. 239-258.

Means et al., "Chemical Modifications of Proteins", Holden-Day Inc., San Francisco, 1971, 254 pages.

Meinkoth et al., "Hybridization of Nucleic Acids Immobilized on Solid Supports", Analytical Biochemistry, vol. 138, No. 2, May 1984, pp. 267-284.

Menzella et al., "Novel *Escherichia coli* Strain Allows Efficient Recombinant Protein Production using Lactose as Inducer", Biotechnology and Bioengineering, vol. 82, No. 7, Jun. 2003, pp. 809-817.

Methe et al., "Genome of *Geobacter sulfurreducens*: Metal Reduction in Subsurface Environments", Science, vol. 302, No. 5652, Dec. 2003, pp. 1967-1969.

Methe et al., "Hypothetical Protein GSU1496 [*Geobacter sulfurreducens* PCA]", Accession No. NP_952547, 2003, 1 page.

Mihalyi, "Numerical Values of the Absorbances of the Aromatic Amino Acids in Acid. Neutral, and Alkaline Solutions", Journal of Chemical & Engineering Data, vol. 13, No. 2, Apr. 1968, pp. pp. 179-182.

Mikayama et al., "Molecular Cloning and Functional Expression of a cDNA Encoding Glycosylation-Inhibiting Factor", PNAS, vol. 90, No. 21, Immunology, Nov. 1993, pp. 10056-10060.

Nagarajan et al., "De Novo Assembly of the Complete Genome of an Enhanced Electricity-Producing Variant of *Geobacter sulfurreducens* Using Only Short Reads", PLoS ONE, vol. 5, No. 6, Jun. 2010, 9 pages.

Nagarajan et al., "Type IV Pilin PilA [*Geobacter sulfurreducens* KN400]", Accession No. ADI84335, 2010, 1 page.

Needleman et al., "A General Method Applicable to the Search for Similarities in the Amino Acid Sequence of Two Proteins", Journal of Molecular Biology, vol. 48, No. 3, Mar. 1970, pp. 443-453.

Pearson et al., "Improved Tools for Biological Sequence Comparison", PNAS, vol. 85, No. 8, 1988, pp. 2444-2448.

Provencher et al., "Estimation of Globular Protein Secondary Structure from Circular Dichroism", Biochemistry, vol. 20, No. 1, Jan. 1981, pp. 33-37.

Reguera et al., "Extracellular Electron Transfer via Microbial Nanowires", Letters, Nature, vol. 435, Nature Publishing Group, Jun. 2005, pp. 1098-1101.

Reguera et al., "Possible Nonconductive Role of *Geobacter sulfurreducens* Pilus Nanowires in Biofilm Formation", Journal of Bacteriology, vol. 189, No. 5, Mar. 2007, pp. 2125-2127.

Rudinger et al., "Characteristics of the Amino Acids as Components of a Peptide Hormone Sequence", National Institute for Medical Research, Jun. 1976, pp. 5-7.

Sambrook, Joe, "Molecular Cloning: A Laboratory Manual", 3rd Edition, Cold Spring Harbor Laboratory Press, 2001.

Siegele et al., "Gene Expression from Plasmids Containing the araBAD Promoter at Subsaturating Inducer Concentrations Represents Mixed Populations", PNAS, vol. 94, No. 15, 1997, pp. 8168-8172.

Smith et al., "Comparison of Biosequences", Advances in Applied Mathematics, vol. 2, No. 4, 1981, pp. 482-489.

Sreerama et al., "Estimation of Protein Secondary Structure from Circular Dichroism Spectra: Comparison of CONTIN, SELCON, and CDSSTR Methods with an Expanded Reference Set", Analytical Biochemistry, vol. 287, No. 2, Dec. 2000, pp. 252-260.

Tijssen, P., "Overview of Principles of Hybridization and the Strategy of Nucleic Acid Probe Assays", Chapter 2, Laboratory Techniques in Biochemistry and Molecular Biology—Hybridization with Nucleic Acid Probes, Part 1, 1993, pp. 19-78.

Van Stokkum et al., "Estimation of Protein Secondary Structure and Error Analysis from Circular Dichroism Spectra", Analytical Biochemistry, vol. 191, No. 1, Nov. 1990, pp. 110-118.

Veazey et al., "Microbial Nanowire Electronic Structure Probed by Scanning Tunneling Microscopy", Biophysical Journal, vol. 98, No. 3, S1, Biophysical Society, Jan. 2010, Mar. 2010, pp. 565a.

Veazey et al., "Electronic Properties of Conductive Pili of the Metal-Reducing Bacterium *Geobacter sulfurreducens* Probed by Scanning Tunneling Microscopy", Physical Review E, vol. 84, Dec. 2011, pp. 060901-1-060901-4.

Walker, John M., "The Protein Protocols Handbook", Parts II and III, Second Edition, Humana Press Inc., 2002, 400 pages.

Wallace et al., "Modern Techniques for Circular Dichroism and Synchrotron Radiation Circular Dichroism Spectroscopy", Advances in Biomedical Spectroscopy, vol. 1, 2009, 245 pages.

Whitmore et al., "DICHROWEB, An Online Server for Protein Secondary Structure Analyses from Circular Dichroism Spectroscopic Data", Nucleic Acids Research, vol. 32, Suppl. 2, Jul. 2004, pp. W668-W673.

Whitmore et al., "Protein Secondary Structure Analyses from Circular Dichroism Spectroscopy: Methods and Reference Databases", Biopolymers, vol. 89, No. 5, May 2008, pp. 392-400.

Wootton et al.. "Statistics of Local Complexity in Amino Acid Sequences and Sequence Databases". Computers & Chemistry. vol. 17, No. 2, Jun. 1993, pp. 149-163.

Yang et al., "Metabolic Response of *Geobacter sulfurreducens* towards Electron Donor/Acceptor Variation", Microbial Cell Factories 2010, vol. 9, No. 90, Nov. 2010, 15 pages.

Final Office Action received for U.S. Appl. No. 13/221,459, mailed on Jun. 26, 2013, 14 pages.

Non Final Office Action received for U.S. Appl. No. 13/221,459, mailed on Jan. 8, 2013, 11 pages.

Notice of Allowance received for U.S. Appl. No. 13/221,459, mailed on Jan. 2, 2014, 8 pages.

Advisory Action received for U.S. Appl. No. 13/221,495, mailed on Jan. 27, 2014, 2 pages.

Final Office Action for received for U.S. Appl. No. 13/221,495, mailed on Nov. 7, 2013, 22 pages.

Non Final Office Action received for U.S. Appl. No. 13/221,495, mailed on Jul. 12, 2013, 19 pages.

International Search Report and Written Opinion received for PCT Patent Application No. PCT/US2012/053221, mailed on Mar. 8, 2013, 15 pages.

Aklujkar et al., "Geopilin [*Geobacter bemidjiensis* Bem]", Accession No. YP_002139394.1, 2010, 1 page.

Aklujkar et al., "The Genome Sequence of *Geobacter metallireducens*: Features of Metabolism, Physiology and Regulation Common and Dissimilar to *Geobacter sulfurreducens*", BMC Microbiology, vol. 9, No. 109, BioMed Central Ltd., May 2009, 22 pages.

Altschul et al., "Gapped BLAST and PSI-BLAST: A New Generation of Protein Database Search Programs", Nucleic Acids Research, vol. 25, No. 17, Sep. 1997, pp. 3389-3402.

Ausubel at at., "Current Protocols in Molecular Biology: Informatics for Molecular Biologists", John Wiley & Sons, Inc., © 2003, Chapter 19, Supplement 70, 2005, 137 pages.

Ausubel et al., "Current Protocols in Molecular Biology: Preparation and Analysis of DNA". John Wiley & Sons, Inc., © 2003, Chapter 2, Supplement 58, 2002, 161 pages.

Ausubel et al., "Current Protocols in Molecular Biology", John Wiley & Sons, Inc., © 2003. Section II (Supplement 41) and Section III (Supplement 44), 1998, 517 pages.

Balch et al., "Methanogens: Reevaluation of a Unique Biological Group", Microbiological Reviews, vol. 43, No. 2, Jun. 1979, pp. 260-296.

Bernard et al., "Tight Attachment of Chitin-Binding-Domain-Tagged Proteins to Surfaces Coated with Acetylated Chitosan", Analytical Biochemistry, vol. 327, No. 2, Apr. 2004, pp. 278-283.

Bolivar et al.. "Construction and Characterization of New Cloning Vehicle. II. A Multipurpose Cloning System", Gene, vol. 2, No. 2, Nov. 1977, pp. 95-113.

(56) References Cited

OTHER PUBLICATIONS

Chang et al., "Phenotypic Expression in *E.coli* of a DNA Sequence Coding for Mouse Dihydrofolate Reductase", Nature, vol. 275, Oct. 1978, pp. 617-624.
Chothia et al., "The Relation between the Divergence of Sequence and Structure in Proteins". The EMBO Journal, vol. 5. No. 4. IRL Press Limited, Oxford, England, Apr. 1986, pp. 823-826.
Claverie et al., "Information Enhancement Methods for Large Scale Sequence Analysis", Computers & Chemistry, vol. 17, No. 2, Jun. 1993, pp. 191-201.
Collinson at al., "Purificaton and Characterization of Thin, Aggregative Fimbriae from *Salmonella enteritidis*", Journal of Bacteriology, vol. 173, No. 15, American Society for Microbiology, Aug. 1991, pp. 4773-4781.
Cologgi et al., "Extracellular Reduction of Uranium via *Geobacter* Conductive Pili as a Protective Cellular Mechanism", PNAS, vol. 108, No. 37, Sep. 2011. pp. 15248-15252.
Copeland et al., "N-terminal Methylation [*Geobacter metallireducens* GS-15]", Accession No. YP_384358.1, 2005, 1 page.
Copeland et al., Pilin Domain-Containing Protein [*Pelobacter propionicus* DSM 2379],, Accession No. YP_901328.1, 2006, 1 page.
Coppi et al., "Development of a Genetic System for *Geobacter sulfurreducens*", Applied and Environmental Microbiology, vol. 76, No. 7, Jul. 2001, pp. 3180-3187.
Corpet, "Multiple Sequence Alignment with Hierarchical Clustering", Nucleic Acids Research, vol. 16, No. 22, Nov. 1988, pp. 10881-10890.
Cory et al., "Fluorescence Spectroscopy Reveals Ubiquitous Presence of Oxidized and Reduced Quinones in Dissolved Organic Matter", Environmental Science & Technology, vol. 39, No. 21, American Chemical Society, Nov. 2005, pp. 8142-8149.
Craig et al., "Type IV Pilus Structure by Cryo-Electron Microscopy and Crystallography: Implications for Pilus Assembly and Functions". Molecular Cell, vol. 23. No. 5, Elsevier Inc., Sep. 2006, pp. 651-662.
De Boer et al., "The Tac Promoter: A Functional Hybrid Derived from the trp and lac Promoters", PNAS, vol. 80, No. 1, Jan. 1983, pp. 21-25.
Fasman, Gerald D., "Practical Handbook of Biochemistry and Molecular Biology", CRC Press. 1989, 616 pages.
Feliciano et al., "Molecular and Electronic Structure of the Peptide Subunit of *Geobacter sulfurreducens* Conductive Pili from First Principles", The Journal of Physical Chemistry A, vol. 116, No. 30, Jul. 2012, pp. 8023-8030.
Feng et al., "Progressive Sequence Alignment as a Prerequisite to Correct Phylogenetic Trees", Journal of Molecular Evolution, vol. 25, No. 4, Aug. 1987, pp. 351-360.
Ferrandon et al., "A Single Surface Tryptophan in the Chitin-Binding Domain From *Bacillus Circulans Chitinase A1* Plays a Pivotal Role in Binding Chitin and can be Modified to Create an Elutable Affinity Tag", Biochimica et Biophysica Acta (BBA)—General Subjects, vol. 1621, No. 1, Apr. 2003, pp. 31-40.
Fong et al., "The Potential Role of Self-Cleaving Purification Tags in Commercial-Scale Processes", Trends in Biotechnology, vol. 28, No. 5, May 2010, pp. 272-279.
Forero, "Properties and Applications of Self-Assembled Biomolecules in Nanostructured Biomimetic Interfaces", Michigan State University. 2011.
Genbank Accession No. ZP 05310612.1, "Pilin Domain-containing Protein [*Geobacter* sp. M18]", Available at www.ncbi.nlm.nih.gov/protein/ZP_05310612.1?report=genpept, Nov. 9, 2010, 1 page.
Goeddel at al., "Direct Expression in *Escherichia coli* of a DNA Sequence Coding for Human Growth Hormone", Nature, vol. 281, Oct. 1979, pp. 544-548.
Goeddel et al., Synthesis of Human Fibroblast Interferon by *E. coli*, Nucleic Acids Research, vol. 8, No. 18, Sep. 1980, pp. 4057-4074.
Greenfield, Norma J., "Using Circular Dichroism Spectra to Estimate Protein Secondary Structure". Nature Protocols, vol. 1, No. 6, 2006. pp. 2876-2890.
Guzman et al., "FTSL, An Essential Cytoplasmic Membrane Protein Involved in Cell Division in *Escherichia coli*", Journal of Bacteriology, vol. 174, No. 23, Dec. 1992, pp. 7716-7728.
Guzman et al., "Tight Regulation, Modulation, and High-Level Expression by Vectors Containing the Arabinose Pbad Promoter". Journal of Bacteriology. vol. 177, No. 14, Jul. 1995, pp. 4121-4130.
Haldimann et al., "Use of New Methods for Construction of Tightly Regulated Arabinose and Rhamnose Promoter Fusions in Studies of the *Escherichia coli* Phosphate Regulon", Journal of Bacteriology, vol. 180, No. 5, Mar. 1998, pp. 1277-1286.
Hay et al., "Protein Engineering of Cytochrome b562 for Quinone Binding and Light-Induced Electron Transfer", PNAS, vol. 101, No. 51, Dec. 2004, pp. 17675-17680.
Henikoff et al., "Amino Acid Substitution Matrices from Protein Blocks", PNAS,vol. 89, No. 22, Nov. 1992, pp. 10915-10919.
Higgins et al., "CLUSTAL: A Package for Performing Multiple Sequence Alignment on a Microcomputer". Gene, vol. 73, No. 1, Dec. 1988, pp. 237-244.
Higgins et al., "Fast and Sensitive Multiple Sequence Alignments on a Microcomputer". Computer Applications in the Biosciences, vol. 5, No. 1, Feb. 1989, pp. 151-153.
Huang et al., "Parallelization of a Local Similarity Algorithm", Computer Applications in the Biosciences. vol. 8, No. 1, Feb. 1992, pp. 155-165.
Kyte et al., "A Simple Method for Displaying the Hydropathic Character of a Protein", Journal of Molecular Biology, vol. 157, No. 1, May 1982, pp. 105-132.
Leang et al., "Alignment of the c-Type Cytochrome OmcS Along Pili of *Geobacter sulfurreducens*", Appl Environ Microbiol., vol. 76, No. 12, Jun. 2010, pp. 4080-4084.
Leang et al., "Genome-Wde Analysis of the RpoN Regulon in *Geobacter sulfurreducens*", BMG Genomics, vol. 10, Jul. 2009, pp. 1-19.
Li et al., "Fed-Batch Fermentor Synthesis of 3-Dehydroshikimic Acid using Recombinant *Escherichia coli*" Biotechnology and Bioengineering, vol. 64, No. 1, Jul. 1999, pp. 61-73.

SEQUENCE LISTING

<160> NUMBER OF SEQ ID NOS: 41

<210> SEQ ID NO 1
<211> LENGTH: 71
<212> TYPE: PRT
<213> ORGANISM: Geobacter sulfurreducens

<400> SEQUENCE: 1

Met Leu Gln Lys Leu Arg Asn Arg Lys Gly Phe Thr Leu Ile Glu Leu
1               5                   10                  15

Leu Ile Val Val Ala Ile Ile Gly Ile Leu Ala Ala Ile Ala Ile Pro
            20                  25                  30

Gln Phe Ser Ala Tyr Arg Val Lys Ala Tyr Asn Ser Ala Ala Ser Ser
        35                  40                  45

Asp Leu Arg Asn Leu Lys Thr Ala Leu Glu Ser Ala Phe Ala Asp Asp
    50                  55                  60

Gln Thr Tyr Pro Pro Glu Ser
65                  70

<210> SEQ ID NO 2
<211> LENGTH: 71
<212> TYPE: PRT
<213> ORGANISM: Geobacter sulfurreducens KN

<400> SEQUENCE: 2

Met Leu Gln Lys Leu Arg Asn Arg Lys Gly Phe Thr Leu Ile Glu Leu
1               5                   10                  15

Leu Ile Val Val Ala Ile Ile Gly Ile Leu Ala Ala Ile Ala Ile Pro
            20                  25                  30

```
Gln Phe Ser Ala Tyr Arg Val Lys Ala Tyr Asn Ser Ala Ser Ser
            35                  40                  45

Asp Leu Arg Asn Leu Lys Thr Ala Leu Glu Ser Ala Phe Ala Asp Asp
 50                  55                  60

Gln Thr Tyr Pro Pro Glu Ser
 65                  70

<210> SEQ ID NO 3
<211> LENGTH: 70
<212> TYPE: PRT
<213> ORGANISM: Geobacter lovleyi SZ

<400> SEQUENCE: 3

Met Leu Asn Lys Ile Arg Asn Arg Lys Gly Phe Thr Leu Ile Glu Leu
 1               5                  10                  15

Leu Ile Val Val Ala Ile Ile Gly Ile Leu Ala Ala Val Ala Ile Pro
                20                  25                  30

Gln Phe Thr Thr Tyr Arg Ile Lys Gly Tyr Asn Ser Asn Ala Thr Ser
            35                  40                  45

Asp Leu Arg Asn Leu Lys Thr Val Leu Glu Ser Val Phe Ala Asp Arg
 50                  55                  60

Gln Gly Tyr Pro Gly Ser
 65                  70

<210> SEQ ID NO 4
<211> LENGTH: 74
<212> TYPE: PRT
<213> ORGANISM: Pelobacter propionicus

<400> SEQUENCE: 4

Met Leu Asn Lys Leu Arg Asn Arg Lys Gly Phe Thr Leu Ile Glu Leu
 1               5                  10                  15

Leu Ile Val Val Ala Ile Ile Gly Ile Leu Ala Ala Ile Ala Ile Pro
                20                  25                  30

Gln Phe Ser Ala Tyr Arg Ala Lys Ala Tyr Asn Ser Ala Ala Asn Ser
            35                  40                  45

Asp Leu Lys Asn Ile Lys Thr Gly Met Glu Ala Phe Met Ala Asp Asn
 50                  55                  60

Gln Gln Tyr Pro Gly Asp Val Asp Tyr Arg
 65                  70

<210> SEQ ID NO 5
<211> LENGTH: 69
<212> TYPE: PRT
<213> ORGANISM: Geobacter metallireducens

<400> SEQUENCE: 5

Met Leu Gln Lys Leu Arg Asn Lys Lys Gly Phe Thr Leu Ile Glu Leu
 1               5                  10                  15

Leu Ile Val Val Ala Ile Ile Gly Ile Leu Ala Ala Ile Ala Ile Pro
                20                  25                  30

Gln Phe Ala Ala Tyr Arg Gln Lys Ala Phe Asn Ser Ala Ala Glu Ser
            35                  40                  45

Asp Leu Lys Asn Thr Lys Thr Asn Leu Glu Ser Tyr Tyr Ser Glu His
 50                  55                  60

Gln Phe Tyr Pro Asn
 65
```

-continued

```
<210> SEQ ID NO 6
<211> LENGTH: 74
<212> TYPE: PRT
<213> ORGANISM: Geobacter

<400> SEQUENCE: 6

Met Leu Asn Lys Leu Arg Ser Asn Lys Gly Phe Thr Leu Ile Glu Leu
1               5                   10                  15

Leu Ile Val Val Ala Ile Ile Gly Ile Leu Ala Ala Ile Ala Ile Pro
            20                  25                  30

Gln Phe Ser Ala Tyr Arg Ala Lys Ala Tyr Asn Ser Ala Ala Asn Ser
        35                  40                  45

Asp Leu Lys Asn Met Lys Thr Gly Met Glu Ala Tyr Met Ala Asp Arg
    50                  55                  60

Gln Ala Tyr Pro Ala Leu Leu Asp Gln Arg
65                  70

<210> SEQ ID NO 7
<211> LENGTH: 76
<212> TYPE: PRT
<213> ORGANISM: Geobacter bemidjiensis

<400> SEQUENCE: 7

Met Leu Asn Lys Leu Arg Ser Asn Lys Gly Phe Thr Leu Ile Glu Leu
1               5                   10                  15

Leu Ile Val Val Ala Ile Ile Gly Ile Leu Ala Ala Ile Ala Ile Pro
            20                  25                  30

Gln Phe Ser Ala Tyr Arg Glu Lys Ala Tyr Asn Ala Ala Ser Asn Ser
        35                  40                  45

Asp Leu Lys Asn Phe Lys Thr Gly Leu Glu Ala Phe Asn Ala Asp Phe
    50                  55                  60

Gln Thr Tyr Pro Ala Ala Tyr Val Ala Ser Thr Asn
65                  70                  75

<210> SEQ ID NO 8
<211> LENGTH: 74
<212> TYPE: PRT
<213> ORGANISM: Geobacter sp

<400> SEQUENCE: 8

Met Leu Asn Lys Ile Arg Ser Asn Lys Gly Phe Thr Leu Ile Glu Leu
1               5                   10                  15

Leu Ile Val Val Ala Ile Ile Gly Ile Leu Ala Ala Ile Ala Ile Pro
            20                  25                  30

Gln Phe Ser Ala Tyr Arg Ala Lys Ala Tyr Asn Ala Ala Ala Asn Ser
        35                  40                  45

Asp Leu Lys Asn Ile Lys Thr Gly Met Glu Ala Tyr Met Ala Asp Arg
    50                  55                  60

Gln Ala Tyr Pro Val Ser Leu Asp Glu Arg
65                  70

<210> SEQ ID NO 9
<211> LENGTH: 61
<212> TYPE: PRT
<213> ORGANISM: Geobacter sulfurreducens

<400> SEQUENCE: 9

Phe Thr Leu Ile Glu Leu Leu Ile Val Val Ala Ile Ile Gly Ile Leu
1               5                   10                  15
```

```
Ala Ala Ile Ala Ile Pro Gln Phe Ser Ala Tyr Arg Val Lys Ala Tyr
            20                  25                  30

Asn Ser Ala Ala Ser Ser Asp Leu Arg Asn Leu Lys Thr Ala Leu Glu
        35                  40                  45

Ser Ala Phe Ala Asp Asp Gln Thr Tyr Pro Pro Glu Ser
    50                  55                  60

<210> SEQ ID NO 10
<211> LENGTH: 71
<212> TYPE: PRT
<213> ORGANISM: Geobacter sulfurreducens

<400> SEQUENCE: 10

Met Leu Gln Lys Leu Arg Asn Arg Lys Gly Phe Thr Leu Ile Glu Leu
1               5                   10                  15

Leu Ile Val Val Ala Ile Ile Gly Ile Leu Ala Ala Ile Ala Ile Pro
            20                  25                  30

Gln Phe Ser Ala Tyr Arg Val Lys Ala Tyr Asn Ser Ala Ala Ser Ser
        35                  40                  45

Asp Leu Arg Asn Leu Lys Thr Ala Leu Glu Ser Ala Phe Ala Asp Asp
    50                  55                  60

Gln Thr Tyr Pro Pro Glu Ser
65                  70

<210> SEQ ID NO 11
<211> LENGTH: 216
<212> TYPE: DNA
<213> ORGANISM: Geobacter sulfurreducens

<400> SEQUENCE: 11
atgcttcaga aactcagaaa caggaaaggt ttcacccctta tcgagctgct gatcgtcgtt    60
gcgatcatcg gtattctcgc tgcaattgcg attccgcagt tctcggcgta cgtgtcaag     120 gcgtacaaca gcgcggcgtc aagcgacttg agaaacctga agactgctct tgagtccgca    180
tttgctgatg atcaaaccta tccgcccgaa agttaa                              216

<210> SEQ ID NO 12
<211> LENGTH: 36
<212> TYPE: DNA
<213> ORGANISM: Artificial Sequence
<220> FEATURE:
<223> OTHER INFORMATION: A synthetic Primer

<400> SEQUENCE: 12
cgcatttgct gatgatcaaa cctttccgcc cgaaag                               36

<210> SEQ ID NO 13
<211> LENGTH: 27
<212> TYPE: DNA
<213> ORGANISM: Artificial Sequence
<220> FEATURE:
<223> OTHER INFORMATION: A synthetic primer

<400> SEQUENCE: 13
cgtgtcaagg cgttcaacag cgcggcg                                         27

<210> SEQ ID NO 14
<211> LENGTH: 29
<212> TYPE: DNA
<213> ORGANISM: Artificial Sequence
<220> FEATURE:
<223> OTHER INFORMATION: A synthetic primer
```

<400> SEQUENCE: 14
ccgcagttct cggcgtttcg tgtcaaggc                                29

<210> SEQ ID NO 15
<211> LENGTH: 30
<212> TYPE: DNA
<213> ORGANISM: Artificial Sequence
<220> FEATURE:
<223> OTHER INFORMATION: A synthetic primer

<400> SEQUENCE: 15
gatgatcaaa cctatccgcc cgcaagttaa                               30

<210> SEQ ID NO 16
<211> LENGTH: 36
<212> TYPE: DNA
<213> ORGANISM: Artificial Sequence
<220> FEATURE:
<223> OTHER INFORMATION: A synthetic primer

<400> SEQUENCE: 16
gagtccgcat tgctgctgc tcaaacctat ccgccc                         36

<210> SEQ ID NO 17
<211> LENGTH: 45
<212> TYPE: DNA
<213> ORGANISM: Artificial Sequence
<220> FEATURE:
<223> OTHER INFORMATION: A synthetic primer

<400> SEQUENCE: 17
gagtccgcat tgctgctgc tcaaacctat ccgcccgcaa gttaa               45

<210> SEQ ID NO 18
<211> LENGTH: 30
<212> TYPE: DNA
<213> ORGANISM: Artificial Sequence
<220> FEATURE:
<223> OTHER INFORMATION: A synthetic primer

<400> SEQUENCE: 18
gatgatcaaa cctatccgcc cgaagcttaa                               30

<210> SEQ ID NO 19
<211> LENGTH: 61
<212> TYPE: PRT
<213> ORGANISM: Artificial Sequence
<220> FEATURE:
<223> OTHER INFORMATION: A synthetic polypeptide

<400> SEQUENCE: 19

Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Tyr
            20                  25                  30

Asn Ser Ala Ala Ser Ser Asp Leu Arg Asn Leu Lys Thr Ala Leu Glu
        35                  40                  45

Ser Ala Phe Ala Asp Asp Gln Thr Phe Pro Pro Glu Ser
    50                  55                  60

<210> SEQ ID NO 20
<211> LENGTH: 61
<212> TYPE: PRT

<213> ORGANISM: Artificial Sequence
<220> FEATURE:
<223> OTHER INFORMATION: A synthetic polypeptide

<400> SEQUENCE: 20

```
Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Phe
            20                  25                  30

Asn Ser Ala Ala Ser Ser Asp Leu Arg Asn Leu Lys Thr Ala Leu Glu
        35                  40                  45

Ser Ala Phe Ala Asp Asp Gln Thr Tyr Pro Pro Glu Ser
    50                  55                  60
```

<210> SEQ ID NO 21
<211> LENGTH: 61
<212> TYPE: PRT
<213> ORGANISM: Artificial Sequence
<220> FEATURE:
<223> OTHER INFORMATION: A synthetic polypeptide

<400> SEQUENCE: 21

```
Phe Thr Leu Ile Glu Leu Leu Ile Val Val Ala Ile Ile Gly Ile Leu
1               5                   10                  15

Ala Ala Ile Ala Ile Pro Gln Phe Ser Ala Phe Arg Val Lys Ala Tyr
            20                  25                  30

Asn Ser Ala Ala Ser Ser Asp Leu Arg Asn Leu Lys Thr Ala Leu Glu
        35                  40                  45

Ser Ala Phe Ala Asp Asp Gln Thr Tyr Pro Pro Glu Ser
    50                  55                  60
```

<210> SEQ ID NO 22
<211> LENGTH: 61
<212> TYPE: PRT
<213> ORGANISM: Artificial Sequence
<220> FEATURE:
<223> OTHER INFORMATION: A synthetic polypeptide

<400> SEQUENCE: 22

```
Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Tyr
            20                  25                  30

Asn Ser Ala Ala Ser Ser Asp Leu Arg Asn Leu Lys Thr Ala Leu Glu
        35                  40                  45

Ser Ala Phe Ala Asp Asp Gln Thr Tyr Pro Pro Ala Ser
    50                  55                  60
```

<210> SEQ ID NO 23
<211> LENGTH: 61
<212> TYPE: PRT
<213> ORGANISM: Artificial Sequence
<220> FEATURE:
<223> OTHER INFORMATION: A synthetic polypeptide

<400> SEQUENCE: 23

```
Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Tyr
            20                  25                  30

Asn Ser Ala Ala Ser Ser Asp Leu Arg Asn Leu Lys Thr Ala Leu Glu
```

```
                  35                  40                  45

Ser Ala Phe Ala Ala Ala Gln Thr Tyr Pro Pro Glu Ser
    50                  55                  60

<210> SEQ ID NO 24
<211> LENGTH: 61
<212> TYPE: PRT
<213> ORGANISM: Artificial Sequence
<220> FEATURE:
<223> OTHER INFORMATION: A synthetic polypeptide

<400> SEQUENCE: 24

Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Tyr
            20                  25                  30

Asn Ser Ala Ala Ser Ser Asp Leu Arg Asn Leu Lys Thr Ala Leu Glu
        35                  40                  45

Ser Ala Phe Ala Ala Ala Gln Thr Tyr Pro Pro Ala Ser
    50                  55                  60

<210> SEQ ID NO 25
<211> LENGTH: 61
<212> TYPE: PRT
<213> ORGANISM: Artificial Sequence
<220> FEATURE:
<223> OTHER INFORMATION: A synthetic polypeptide

<400> SEQUENCE: 25

Phe Thr Leu Ile Glu Leu Leu Ile Val Val Ala Ile Ile Gly Ile Leu
1               5                   10                  15

Ala Ala Ile Ala Ile Pro Gln Phe Ser Ala Tyr Arg Val Lys Ala Tyr
            20                  25                  30

Asn Ser Ala Ala Ser Ser Asp Leu Arg Asn Leu Lys Thr Ala Leu Glu
        35                  40                  45

Ser Ala Phe Ala Asp Asp Gln Thr Tyr Pro Pro Glu Ala
    50                  55                  60

<210> SEQ ID NO 26
<211> LENGTH: 51
<212> TYPE: PRT
<213> ORGANISM: Geobacter sulfurreducens

<400> SEQUENCE: 26

Ala Ile Ile Gly Ile Leu Ala Ala Ile Ala Ile Pro Gln Phe Ser Ala
1               5                   10                  15

Tyr Arg Val Lys Ala Tyr Asn Ser Ala Ala Ser Ser Asp Leu Arg Asn
            20                  25                  30

Leu Lys Thr Ala Leu Glu Ser Ala Phe Ala Asp Asp Gln Thr Tyr Pro
        35                  40                  45

Pro Glu Ser
    50

<210> SEQ ID NO 27
<211> LENGTH: 42
<212> TYPE: PRT
<213> ORGANISM: Geobacter sulfurreducens

<400> SEQUENCE: 27

Ala Ile Pro Gln Phe Ser Ala Tyr Arg Val Lys Ala Tyr Asn Ser Ala
1               5                   10                  15
```

```
Ala Ser Ser Asp Leu Arg Asn Leu Lys Thr Ala Leu Glu Ser Ala Phe
            20                  25                  30

Ala Asp Asp Gln Thr Tyr Pro Pro Glu Ser
            35                  40
```

<210> SEQ ID NO 28
<211> LENGTH: 41
<212> TYPE: PRT
<213> ORGANISM: Geobacter sulfurreducens

<400> SEQUENCE: 28

```
Ile Pro Gln Phe Ser Ala Tyr Arg Val Lys Ala Tyr Asn Ser Ala Ala
 1               5                  10                  15

Ser Ser Asp Leu Arg Asn Leu Lys Thr Ala Leu Glu Ser Ala Phe Ala
            20                  25                  30

Asp Asp Gln Thr Tyr Pro Pro Glu Ser
            35                  40
```

<210> SEQ ID NO 29
<211> LENGTH: 39
<212> TYPE: PRT
<213> ORGANISM: Geobacter sulfurreducens

<400> SEQUENCE: 29

```
Gln Phe Ser Ala Tyr Arg Val Lys Ala Tyr Asn Ser Ala Ala Ser Ser
 1               5                  10                  15

Asp Leu Arg Asn Leu Lys Thr Ala Leu Glu Ser Ala Phe Ala Asp Asp
            20                  25                  30

Gln Thr Tyr Pro Pro Glu Ser
            35
```

<210> SEQ ID NO 30
<211> LENGTH: 82
<212> TYPE: PRT
<213> ORGANISM: Kluyveromyces lactis

<400> SEQUENCE: 30

```
Asp Ser Trp Ala Val Thr Arg Ala Lys Glu Leu Asn Glu Gln Phe Val
 1               5                  10                  15

Lys Gly Glu Leu Asn Gly Lys Asp Ser Cys Ser Asp Gly Glu Ile Ser
            20                  25                  30

Cys Thr Ala Asp Gly Lys Ile Ala Ile Cys Asn Tyr Gly Ala Trp Val
            35                  40                  45

Tyr Thr Glu Cys Ala Ala Gly Thr Thr Cys Phe Ala Tyr Asp Ser Gly
        50                  55                  60

Asp Ser Val Tyr Thr Ser Cys Asn Phe Thr Tyr Leu Lys Pro Asp Val
65                  70                  75                  80

Val Phe
```

<210> SEQ ID NO 31
<211> LENGTH: 75
<212> TYPE: PRT
<213> ORGANISM: Kluyveromyces lactis

<400> SEQUENCE: 31

```
Asp Ser Trp Ala Val Thr Arg Ala Lys Glu Leu Asn Glu Gln Phe Val
 1               5                  10                  15

Lys Gly Glu Leu Asn Gly Lys Asp Ser Cys Ser Asp Gly Glu Ile Ser
            20                  25                  30
```

-continued

```
Cys Thr Ala Asp Gly Lys Ile Ala Ile Cys Asn Tyr Gly Ala Trp Val
         35                  40                  45

Tyr Thr Glu Cys Ala Ala Ser Thr Thr Cys Phe Ala Tyr Asp Ser Gly
 50                  55                  60

Asp Ser Val Tyr Thr Ser Cys Asn Leu Leu Ile
 65                  70                  75

<210> SEQ ID NO 32
<211> LENGTH: 20
<212> TYPE: DNA
<213> ORGANISM: Artificial Sequence
<220> FEATURE:
<223> OTHER INFORMATION: A synthetic primer

<400> SEQUENCE: 32
tggataggcg ggctttcaat                                             20

<210> SEQ ID NO 33
<211> LENGTH: 21
<212> TYPE: DNA
<213> ORGANISM: Artificial Sequence
<220> FEATURE:
<223> OTHER INFORMATION: A synthetic primer

<400> SEQUENCE: 33
attccgcagt tctcggcgta t                                           21

<210> SEQ ID NO 34
<211> LENGTH: 30
<212> TYPE: DNA
<213> ORGANISM: Artificial Sequence
<220> FEATURE:
<223> OTHER INFORMATION: A synthetic primer

<400> SEQUENCE: 34
cccaagcttt taactttcgg gcggataggt                                  30

<210> SEQ ID NO 35
<211> LENGTH: 20
<212> TYPE: DNA
<213> ORGANISM: Artificial Sequence
<220> FEATURE:
<223> OTHER INFORMATION: A synthetic primer

<400> SEQUENCE: 35
attccgcagt tctcggcgta                                             20

<210> SEQ ID NO 36
<211> LENGTH: 36
<212> TYPE: DNA
<213> ORGANISM: Artificial Sequence
<220> FEATURE:
<223> OTHER INFORMATION: A synthetic primer

<400> SEQUENCE: 36
ggtggtctgc agtcattaac tttcgggcgg ataggt                           36

<210> SEQ ID NO 37
<211> LENGTH: 38
<212> TYPE: DNA
<213> ORGANISM: Artificial Sequence
<220> FEATURE:
<223> OTHER INFORMATION: A synthetic primer

<400> SEQUENCE: 37
```

```
ggtggttgct cttccaactt caccottatc gagctgct                              38
```

<210> SEQ ID NO 38
<211> LENGTH: 38
<212> TYPE: DNA
<213> ORGANISM: Artificial Sequence
<220> FEATURE:
<223> OTHER INFORMATION: A synthetic primer

<400> SEQUENCE: 38

```
ggtggttgct cttccaacgc gatcatcggt attctcgc                              38
```

<210> SEQ ID NO 39
<211> LENGTH: 38
<212> TYPE: DNA
<213> ORGANISM: Artificial Sequence
<220> FEATURE:
<223> OTHER INFORMATION: A synthetic primer

<400> SEQUENCE: 39

```
ggtggttgct cttccaacgc gattccgcag ttctcggc                              38
```

<210> SEQ ID NO 40
<211> LENGTH: 38
<212> TYPE: DNA
<213> ORGANISM: Artificial Sequence
<220> FEATURE:
<223> OTHER INFORMATION: A synthetic primer

<400> SEQUENCE: 40

```
ggtggttgct cttccaacat tccgcagttc tcggcgta                              38
```

<210> SEQ ID NO 41
<211> LENGTH: 38
<212> TYPE: DNA
<213> ORGANISM: Artificial Sequence
<220> FEATURE:
<223> OTHER INFORMATION: A synthetic primer

<400> SEQUENCE: 41

```
ggtggttgct cttccaacca gttctcggcg tatcgtgt                              38
```

MICROBIAL NANOWIRES AND METHODS OF MAKING AND USING

RELATED APPLICATIONS

This application is a continuation-in-part under 35 U.S.C. 111(a) of International Application No. PCT/US2012/053221, which application was filed on Aug. 30, 2012 and published in English as WO 2013/033456 on Mar. 7, 2013, which application claims the benefit under 35 U.S.C. 119 (e) of U.S. Provisional Application Ser. No. 61/530,708, filed on Sep. 2, 2011 and U.S. Provisional Application Ser. No. 61/558,091, filed on Nov. 10, 2011, which applications and publications are hereby incorporated by reference in their entireties.

STATEMENT OF GOVERNMENT RIGHTS

This invention was made with government support under R01 ES017052-03 awarded by the National Institutes of Health, DE-SC0000795 awarded by the U.S. Department of Energy, and MCB1021948 awarded by the National Science Foundation. The government has certain rights in this invention.

BACKGROUND

The world needs new energy sources or and new materials for use in fuel cells, nanoelectronic devices or in pollution clean-up. Protein nanowires from *Geobacter* bacteria exhibit conductive properties and may be adapted for a variety of uses. However, growth of *Geobacter* needs to proceed under anaerobic conditions, because oxygen poisons the bacteria and inhibits grow. The native *Geobacter* bacteria also produce a limited number of nanowires per cell, which limits the nanowire yield during purification.

SUMMARY

Microbes have the potential to address the problems of pollution, the need for clean affordable energy and the need for new nanoelectronic materials. The embodiments of the invention disclosed herein relates to microbial nanowires that conduct electricity. Such nanowires or pili are made from microbial pilins. The invention also relates to expression cassettes, expression vectors and host cells (e.g., bacteria) that produce such pilins and nanowires. In some embodiments, the nucleic acids encoding the nanowire peptides are recombinantly modified so that nanowire peptides and polypeptides with modified conductive properties can be produced.

One aspect of the invention is a nanowire polypeptide comprising an amino acid sequence selected from SEQ ID NO:1-10, 26-29. In some embodiments, the amino acid sequence of the disclosed nanowire polypeptides are genetically or chemically modified so the nanowire polypeptide has electrical conductivity or other desirable activity. In other embodiments, the modified nanowire polypeptides have modified adhesive or coupling properties relative to wild-type nanowire polypeptides Another aspect of the invention is a pilus or pili that includes such a modified nanowire polypeptide. Further aspects of the invention use the disclosed nanowire peptides in devices and for soluble metal remediation.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 8B showing the structure of recombinant 19 amino acid truncation $PilA_{19}$ protein; and FIG. 8C showing the structure of recombinant cysteine-modified 19 amino acid truncation $PilA_{19}$-A20C protein (with added cysteine colored turquoise, and the tyrosines colored light blue in each structure shown in FIGS. 8A-8C); and FIG. 8D showing the sequence alignment of wild type and recombinant pilins of *Geobacter sulfurreducens*.

As shown in FIG. 16A, the coulombic efficiencies, which depend on the cell's ability to metabolize the electron donor and convert it into electricity, were undisturbed. However, FIG. 16B shows that the amino acid replacements resulted in nanowires with reduced conductivity, as indicated by the observed defects in the electron transfer rates to electrodes in microbial fuel cells.

FIG. 30C showing an image of a heme-stained SDS-PAGE of protein extracted from the exopolysaccharide (EPS) matrix of 48 h biofilms of the WT (lane 1), PilA− (lane 2), and pRG5::pilA (lane 3) strains. Numbers at the right are relative molecular weights of protein markers in kDa. The arrow points at the migration of the small, processed form of the OmcZ c-cytochrome (OmcZ$_S$).

FIG. 36A shows the magnitude of Fourier transform spectra (symbols) and model (line). The spectra are offset for clarity in descending order PilA− and WT. The inset shows the U(IV) moiety consistent with the measured EXAFS spectra for both WT and PilA− biofilms (grey) oxygen (red) and carbon (black). The real part of Fourier transform of WT is shown in FIG. 36B and the PilA− is shown in FIG. 36C. The components of the model are shown offset beneath the total model and measured spectrum.

DETAILED DESCRIPTION OF THE EMBODIMENTS

Figure 1:
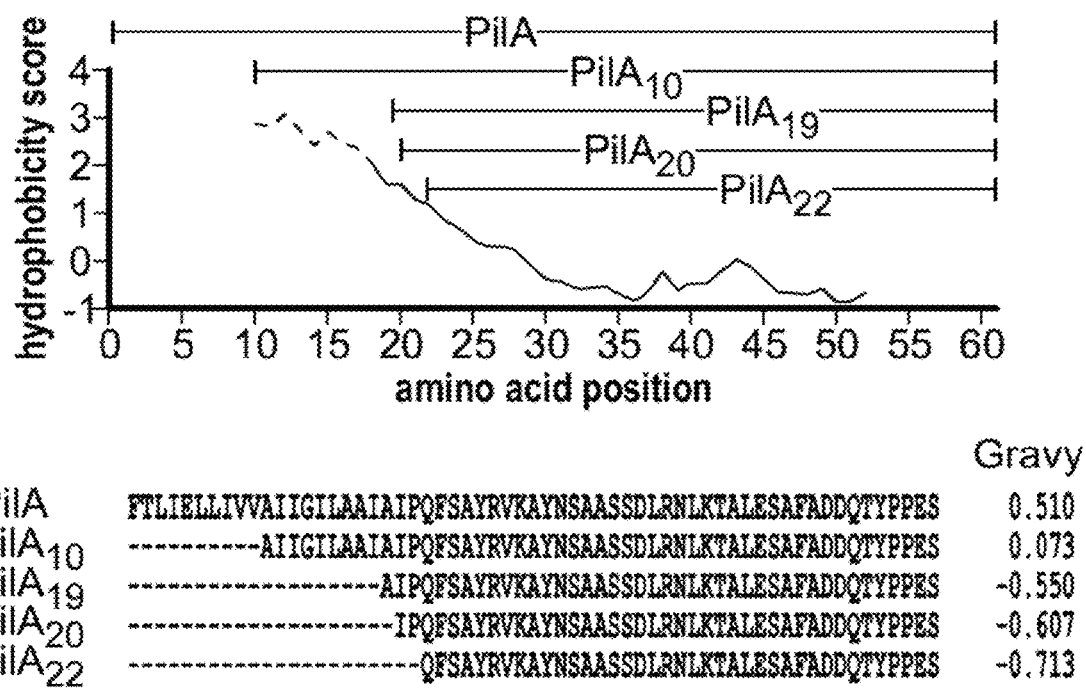
FIG. 1 is a Kyte & Doolittle hydrophobicity plot of the *G. sulfurreducens* nanowire pilin PilA and PilA truncated peptides, where the graph at the top is a plot of amino acid position along the x-axis and, a measure of the hydrophobicity of the peptides along the y-axis, i.e., the grand average of hydropathicity (GRAVY) index (see, Kyte & Doolittle, *Journal of Molecular Biology* 157, 105-132 (1982)). The amino acid sequences of the PilA peptide (SEQ ID NO: 9), the $PilA_{10}$ peptide (SEQ ID NO: 34) and the $PilA_{19}$ peptide (SEQ ID NO:35), the $PilA_{20}$ (SEQ ID NO:36) and the $PilA_{22}$ peptide (SEQ ID NO:37) are shown at the bottom.

In the following detailed description, embodiments are described in sufficient detail to enable those skilled in the art to practice them, and it is to be understood that other embodiments may be utilized and that chemical and procedural changes may be made without departing from the spirit and scope of the present subject matter. The following detailed description is, therefore, not to be taken in a limiting sense, and the scope of embodiments is defined only by the appended claims.

The terms "acidic amino acid" or "negatively charged amino acid" refer to a hydrophilic amino acid having a side chain pK value of less than 7. Acidic amino acids typically have negatively charged side chains at physiological pH due to loss of a proton. Examples of genetically encoded acidic amino acids include, but are not limited to, aspartic acid (aspartate) and glutamic acid (glutamate).

The term "aliphatic amino acid" refers to an apolar amino acid having a saturated or unsaturated straight chain, branched or cyclic hydrocarbon side chain. Examples of genetically encoded aliphatic amino acids include, but are not limited to, Alanine (Ala), Leucine (Leu), Valine (Val) and Isoleucine. Examples of non-encoded aliphatic amino acids include, but are not limited to, Norleucine.

The term "apolar amino acid" refers to a hydrophobic amino acid having a side chain that is generally uncharged at physiological pH and that is not polar. Examples of genetically encoded apolar amino acids include, but are not limited to, proline and methionine. Examples of non-encoded apolar amino acids include, but are not limited to, β-cyclohexylalanine.

The term "aromatic amino acid" refers to a hydrophobic or hydrophilic amino acid having a side chain containing at least one ring having a conjugated π-electron system (aromatic group). The aromatic group may be further substituted with substituent groups such as alkyl, alkenyl, alkynyl, hydroxyl, sulfonyl, nitro and amino groups, and the like. Examples of genetically encoded aromatic amino acids include, but are not limited to, phenylalanine, tyrosine and tryptophan. Commonly encountered non-genetically encoded aromatic amino acids include phenylglycine, 2-naphthylalanine, β-2-thienylalanine, 1,2,3,4-tetrahydroisoquinoline-3-carboxylic acid, 4-chlorophenylalanine, 2-fluorophenylalanine, 3-fluorophenylalanine and 4-fluorophenylalanine.

The term "asymmetric conductor" refers to differential forward versus reverse conductivity of the nanoscale assembled nanowire polypeptides. Thus, when the nanowire peptides described herein assemble into polypeptide pili they exhibit asymmetric axial electronic conductance.

The term "basic amino acid" refers to a hydrophilic amino acid having a side chain pK value of greater than 7. Basic amino acids typically have positively charged side chains at physiological pH due to association with hydronium ion. Examples of genetically encoded basic amino acids include, but are not limited to, arginine, lysine and histidine. Examples of non-genetically encoded basic amino acids include, but are not limited to, the non-cyclic amino acids ornithine, 2,3-diaminopropionic acid, 2,4-diaminobutyric acid and homoarginine.

The term "biofilm" refers to a community of microbes particularly bacteria attached to a surface with the community members being contained or protected by a self-generated extracellular polymeric matrix or EPS.

The term "comparison window" refers to a contiguous and specified segment of a nucleic acid or an amino acid sequence, wherein the nucleic acid/amino acid sequence may be compared to a reference sequence and wherein the portion of the nucleic acid/amino acid sequence in the comparison window may comprise additions or deletions (i.e., gaps) compared to the reference sequence (which does not comprise additions or deletions) for optimal alignment of the two sequences. The comparison window can vary for nucleic acid or peptide sequences.

The term "conductance" refers to a material property whereby electrons migrate through the material in response to an applied voltage (difference in electrical potential) across the material. The rate of electron migration (charge/time) is the electrical current passing through the material. Materials that exhibit conductance are referred to as conductors.

The term "cysteine-like amino acid" refers to an amino acid having a side chain capable of forming a covalent linkage with a side chain of another amino acid residue, such as a disulfide linkage. Typically, cysteine-like amino acids generally have a side chain containing at least one thiol (SH) group. An example of a genetically encoded cysteine-like amino acid is cysteine. Examples of non-genetically encoded cysteine-like amino acids include, but are not limited to, homocysteine and penicillamine.

The term "devices" refers to a component or a contrivance containing or associated with one or more pilin subunits that provides the component or contrivance with a combination of the pilin subunit's properties. The pilin subunit properties include electrical properties (e.g. conductivity or rectification), dimensional properties, (e.g. diameter or aspect ratio), or physicochemical properties (e.g. nontoxicity, rigidity, charge, ability to self-assemble from monomer peptides or functional groups that facilitate binding or chemical reactions).

The term "expression control sequence" refers to a nucleic acid sequence sufficient to direct the transcription of another nucleic acid sequence that is operably linked to the expression control sequence to produce an RNA transcript.

The term "expression vector" refers to a nucleic acid molecule capable of transporting and/or allowing for the expression of another nucleic acid to which it has been linked.

The term "heavy metal" refers to a metal which is a member of a loosely-defined subset of elements that exhibit metallic properties. It mainly includes the transition metals, some metalloids, lanthanides, and actinides (e.g., uranium). A heavy metal can further be considered to include any metallic chemical element that has a relatively high density and is toxic or poisonous at low concentrations. Examples include, but are not limited to, mercury, lead, and radioactive elements such as uranium, thorium, and the like.

The term "hydrophilic amino acid" refers to an amino acid having a side chain that is attracted by aqueous solution. Examples of genetically encoded hydrophilic amino acids include, but are not limited to, Serine (Ser) and Lysine (Lys). Examples of non-encoded hydrophilic amino acids include, but are not limited to, Citruline (Cit) and homocysteine (hCys).

The term "hydrophobic amino acid" refers to an amino acid having a side chain that is uncharged at physiological pH and that is repelled by aqueous solution. Examples of genetically encoded hydrophobic amino acids include, but are not limited to, Ala, Ile, Leu and Val. Examples of non-genetically encoded hydrophobic amino acids include, but are not limited to, t-Butylalanine (t-BuA).

The terms "interface" "interfacing" or "interfaced" refers bringing or binding two or more components in close proximity.

The terms "nanowire", "protein nanowire", "nanowire protein", and "nanowire polypeptide" are also used interchangeably with "pilin."

The term "operably linked" refers to a nucleic acid and an expression control sequence positioned in such a way that the expression control sequence directs expression of the nucleic acid under appropriate culture conditions and when the appropriate molecules such as RNA transcriptional proteins are bound to the expression control sequence.

The terms "peptide" or a "polypeptide" refer to at least two amino acid residues connected as a chain via covalent peptide bonds, and can be recombinant peptides/polypeptides, native peptides/polypeptides or synthetic peptides/polypeptides. The terms "peptide", "polypeptide", and "protein" are all used herein to describe polymers of amino acid monomers. The terms "peptide" and "pilin subunit" are used interchangeably.

The term "polar amino acid" refers to a hydrophilic amino acid having a side chain that is uncharged at physiological pH, but where a bond in the side chain has a pair of electrons that are held more closely by one of the atoms involved in the bond. Examples of genetically encoded polar amino acids include, but are not limited to, asparagine and glutamine. Examples of non-genetically encoded polar amino acids include, but are not limited to, citrulline, N-acetyl lysine and methionine sulfoxide.

The term "reference sequence" refers to a defined sequence used as a basis for sequence comparison. The reference sequence can be a nucleic acid sequence or amino acid sequence.

The term "signal sequence" or "signal peptide" refers to a peptide that can be used to secrete the heterologous polypeptide into the bacterial periplasm. The signal for the heterologous polypeptide may be homologous to the bacteria, or they may be heterologous, including signals native to the polypeptide being produced in the bacteria.

The term "soluble metal" refers to a metal which is soluble in oxidized form and which precipitates in reduced form. Examples include, but are not limited to, uranium, vanadium, chromium, cadmium and technetium. The term "metal" is intended to include any type of "metalloid" which refers to elements with intermediate or mixed properties and can further include soluble lanthanides, transition metals and actinides.

The terms "stringent conditions" or "stringent hybridization conditions" refer to conditions under which a probe will hybridize to its target sequence to a detectably greater degree than other sequences (e.g., at least 2-fold over background).

The term "substantial identity" refers to a peptide, protein or nucleic acid comprises a sequence with between 55-100% sequence identity to a reference sequence.

The term "substrate" refers to a substance to which another substance binds or connects.

There are currently no effective technologies to remove soluble or heavy metal contaminants from the environment, such as uranium contaminants. Uranium is particularly problematic, at least in part, because it is often present as hexavalent uranium (U(VI)), which is soluble in water, and therefore mobile. This results in vast volumes of contaminated waters and groundwaters. Uranium VI is also reactive, thus facilitating its adsorption to sediments and soils. Its radioactivity also decays very slowly (billions of years). For these reasons, traditional clean-up methods such as pump-and-treat approaches cannot be applied. These challenges highlight the need to find treatment options that are both efficient and cost-effective, and that cause minimum environmental disruption.

Conventional attempts include in situ stimulation of native or added metal-reducing microorganisms which transfer electrons to electron acceptors in the environment and, concomitantly, reduce the contaminants. These microorganisms immobilize and, in some cases, reduce the heavy metal, such as uranium, inside their cell envelope. However, this process is not sustainable because, once the heavy metal precipitates in the cell's periplasm, the cell envelope's integrity and functioning and the cell's viability is compromised. In particular, when the heavy metal penetrates the cell envelope of some bacterial strains, it is reductively precipitated and kills the cell, in some cases after only a few hours of heavy metal exposure.

Some metal-reducing bacteria naturally produce protein filaments known as pili that are electrically conductive and generally referred to as microbial or pilus nanowires. The pilus nanowires are protein filaments assembled on the cell envelope through the polymerization via hydrophobic interactions of a single peptide subunit, the pilin or PilA. The purified pili are electrically conductive.

The peptide subunit (or pilin) in the electrically conductive pili is encoded by a pilA gene (e.g., by Geobacteraceae bacteria). The product of the pilA gene generates a peptide or PilA or pilin that polymerizes via hydrophobic interactions to form the pilus fiber or nanowire. The pilus nanowire electrically connects the cell with electron acceptors in its environment. This electronic connection enables the cell to gain energy for growth through the transfer of metabolically-generated electrons across electron transport proteins, such as c-cytochromes and other metalloproteins of the cell envelope, and through the pilus. The pilus serves as the main electrical connection between the cell and extracellular acceptors such as Fe(III) oxides.

Some metal-reducing bacteria (e.g., *Geobacter sulfurreducens*) are naturally found in underground sediment where anaerobic conditions may require that an electron acceptor other than oxygen be employed and where minerals or other electron acceptors are commonly available. Thus, although metal-reducing bacteria can utilize oxygen as an electron acceptor, these bacteria can also transfer electrons from their pili to extracellular electron acceptors such as Fe(III) oxides, resulting in insoluble Fe(III) in the environment to be reduced to soluble Fe(II) and the magnetic mineral magnetite.

The pilus nanowires are dynamic filaments that protrude and retract by polymerizing and depolymerizing the pilin subunits at the cell envelope. Thus, several pilin peptides are assembled to make a pilus that can function as a nanowire. Extension and retraction events are powered, respectively, by the PilB (pilin polymerase) and PilT (pilin depolymerase) proteins, which belong to the secretion NTPase superfamily. The pilus nanowires are predominantly helical in structure. The nanowire pilin subunit is also predominantly helical, being composed of an α-helical core spanning the hydrophobic N-terminus region that promotes pilin polymerization, and a short random-coiled segment in the C-terminal region. Thus, they lack the long αβ-loop and extensive C-terminal globular head that other bacterial pili possess.

Pilin assembly occurs via hydrophobic interactions proceeding in a helical fashion that may help position electroactive amino acids by merging or bonding their atomic orbitals optimally so as to favor charge transport along and across the nanowire Different bacterial species, including bacteria from the family Geobacteraceae, can be used to produce nanowire protein filaments. Many members of the Geobacteraceae family naturally produce pilin subunits (or PilA subunits) that self-assemble into conductive pili. The different Geobacteraceae species can express PilA subunits with somewhat different amino acid sequences, and pilin subunits are selected that assemble into protein filaments and are capable of establishing an electrical connection with an insoluble electron acceptor.

In one embodiment, the pilin subunit can be from *Geobacter sulfurreducens*. Amino acids 20-90 of the *Geobacter sulfurreducens* PCA pilA nanowire with sequence accession number NP_952547.1 (gi: 39996596) has the following sequence (SEQ ID NO:1).

```
20    MLQKLRNRKG FTLIELLIVV AIIGILAAIA IPQFSAYRVK

60    AYNSAASSDL RNLKTALESA FADDQTYPPE S
```

Other pilins can also be employed. The Type IV pilin PilA from *Geobacter sulfurreducens* KN400 having sequence accession number ADI84335.1 (gi:298505612) can be used and has the following sequence (SEQ ID NO:2).

```
1     MLQKLRNRKG FTLIELLIVV AIIGILAAIA IPQFSAYRVK

41    AYNSAASSDL RNLKTALESA FADDQTYPPE S
```

The pilin domain-containing protein *Geobacter lovleyi* SZ having sequence accession number YP_001952332.1 (gi:189425155) has the following sequence (SEQ ID NO:3).

```
1    MLNKIRNRKG FTLIELLIVV AIIGILAAVA IPQFTTYRIK
41   GYNSNATSDL RNLKTVLESV FADRQGYPGS
```

The pilin domain-containing protein of *Pelobacter propionicus* DSM 2379 having sequence accession number YP_901328.1 (gi:118580078) has the following sequence (SEQ ID NO:4).

```
1    MLNKLRNRKG FTLIELLIVV AIIGILAAIA IPQFSAYRAK
41   AYNSAANSDL KNIKTGMEAF MADNQQYPGD VDYR
```

The domain from *Geobacter metallireducens* GS-15 having sequence homology to *Geobacter* pilins and having accession number YP_384358.1 (gi:78222611) has the following sequence (SEQ ID NO:5).

```
1    MLQKLRNKKG FTLIELLIVV AIIGILAAIA IPQFAAYRQK
41   AFNSAAESDL KNTKTNLESY YSEHQFYPN
```

The pilin from *Geobacter* sp. M21 having accession number YP_003021449.1 (gi:253700260) has the following sequence (SEQ ID NO:6).

```
1    MLNKLRSNKG FTLIELLIVV AIIGILAAIA IPQFSAYRAK
41   AYNSAANSDL KNMKTGMEAY MADRQAYPAL LDQR
```

The pilin from *Geobacter bemidjiensis* Bem having accession number YP_002139394.1 (gi:197118967) has the following sequence (SEQ ID NO:7).

```
1    MLNKLRSNKG FTLIELLIVV AIIGILAAIA IPQFSAYREK
41   AYNAASNSDL KNFKTGLEAF NADFQTYPAA YVASTN
```

The pilin domain-containing protein from *Geobacter* sp. M18 having accession number ZP_05310612.1 (gi: 255058444) has the following sequence (SEQ ID NO:8).

```
1    MLNKIRSNKG FTLIELLIVV AIIGILAAIA IPQFSAYRAK
41   AYNAAANSDL KNIKTGMEAY MADRQAYPVS LDER
```

The pilin subunit of *Geobacter sulfurreducens* can also have the SEQ ID NO:9 sequence, which is reproduced below.

```
1    FTLIELLIVV AIIGILAAIA IPQFSAYRVK AYNSAASSDL
41   RNLKTALESA FADDQTYPPE S
```

The amino acid sequence of the PilA peptide from *Geobacter sulfurreducens* is shown below as SEQ ID NO:10.

```
1    MLQKLRNRKG FTLIELLIVV AIIGILAAIA IPQFSAYRVK
41   AYNSAASSDL RNLKTALESA FADDQTYPPE S
```

The SEQ ID NO:10 pilA peptide has a signal peptide. The processing site for the SEQ ID NO:10 signal peptide is between the glycine at position 10 and the phenylalanine at position 11. Removal of this signal peptide yields the SEQ ID NO:1 nanowire pilin sequence. The N-terminal phenylalanine of the SEQ ID NO:1 peptide can also be methylated during processing of the signal peptide.

The SEQ ID NO:1 and 10 pilin peptides are encoded by the following pilA nucleic acid sequence (SEQ ID NO:11).

```
     ATG CTT CAG AAA CTC AGA AAC AGG AAA GGT
31   TTC ACC CTT ATC GAG CTG CTG ATC GTC GTT
61   GCG ATC ATC GGT ATT CTC GCT GCA ATT GCG
91   ATT CCG CAG TTC TCG GCG TAT CGT GTC AAG
121  GCG TAC AAC AGC GCG GCG TCA AGC GAC TTG
151  AGA AAC CTG AAG ACT GCT CTT GAG TCC GCA
181  TTT GCT GAT GAT CAA ACC TAT CCG CCC GAA
211  AGT TAA
```

In other embodiments, the conductive pili can have pilin peptides with at least 40%, at least 45%, at least 50%, at least 55%, at least 60%, at least 65%, or at least 70%, or at least 75%, or at least 80%, or at least 85%, or at least 90%, or at least 95%, or at least 97% sequence identity to a nanowire pilin having an amino acid sequence comprising any of the SEQ ID NO:1-10.

In further embodiments, the nanowire pilin with at least 60% sequence identity of any of the SEQ ID NO:1-10 can also have a truncation at the N-terminus or at the C-terminus of about 30 amino acids, or of about 1-28 amino acids, or of about 1-25 amino acids, or of about 1-22 amino acids, or of about 1-20 amino acids, or of about 1-19 amino acids, or of about 1-17 amino acids, or of about 1-15 amino acids, or of about 1-13 amino acids, or of about 1-12 amino acids, or of about 1-10 amino acids, or of about 1-9 amino acids, or of about 1-8 amino acids, or of about 1-7 amino acids, or of about 1-6 amino acids, or of about 1-5 amino acids, or of about 1-4 amino acids, or of about 1-3 amino acids, or of about 1-2 amino acids.

For additional details and sequence listings, see U.S. Provisional Application Ser. No. 61/378,188, filed on Aug. 30, 2010 and entitled, "Microbial Nanowires and Methods of Making and Using Same." See also U.S. application Ser. No. 13/221,459, filed on Aug. 30, 2011 and entitled, "Microbial Nanowires and Methods of Making and Using Same," both of which are hereby incorporated by reference herein in their entireties.

Chemical modification (e.g., which may include chemical stripping) or genetic engineering, can be used to manipulate the protein composition, structure and binding properties of microbial nanowires to selectively modify conductance properties. Microbial nanowires can also be manipulated via genetic engineering to bind specific ligands for sensor design, controlled and specific deposition during device manufacturing, and the like. In one embodiment, genetic engineering or chemical modification is used to produce nanowires with various functionalities. In one embodiment, *Geobacter sulfurreducens*, is used. For additional details and sequence listings, see U.S. Provisional Application Ser. No. 61/378,240, filed on Aug. 30, 2010 and entitled, "Microbial Nanowires." See also U.S. application Ser. No. 13/221,495, filed on Aug. 30, 2011 and entitled, "Microbial Nanowires," both of which are hereby incorporated by reference herein in their entireties.

In some embodiments, the nanowire peptides or polypeptides are chemically modified. Chemically modified nanowire peptides and polypeptides can be generated from nanowire peptides/polypeptides with a natural (non-recombinantly engineered) sequence that is chemically modified. In other embodiments, the chemically modified nanowire polypeptides can be generated with a mutant nanowire peptide that contains substitutions, deletions or additions of amino acids that are not normally found in naturally occurring pilus nanowires. Thus, for example, before chemical modification, the nanowire peptides can have any of SEQ ID NO:1-10, 26-29, or a variant or modification thereof. The nanowire peptides can therefore have a genetically modified sequence made by any of the procedures described herein.

In some embodiments, the nanowire peptides or polypeptides can be chemically modified to modulate their conductive, adhesive, coupling or other properties. Such chemical modification can be performed by procedures available in the art using a variety of reagents. For example, reagents such as performic acid, peroxides, iodoacetamide, iodoacetic acid, bissulfosuccinimidyl suberate, 1-ethyl-3-(3-dimethylaminopropyl) carbodiimide, N-ethylmaleimide, methyl methanethiosulfonate and S-(2,2,5,5-tetramethyl-2, 5-dihydro-1H-pyrrol-3-yl)methyl methanesulfonothioate (MTSL) can be used to modify the conductive, adhesive, coupling or other properties of the nanowire polypeptides. In other embodiments, the nanowire peptides or polypeptides can be glycosylated, acylated or conjugated to an alkylene glycol (e.g., polyethylene glycol or PEG). Such modifications can be performed by procedures available in the art. See, e.g., John M. Walker, THE PROTEIN PROTOCOLS HANDBOOK (2002); Means, G. E. and Feeney, R. E. CHEMICAL MODIFICATIONS OF PROTEINS. Holden-Day, San Francisco (1971).

In one embodiment, the nanowires can be mass produced, such as by the following steps:

1) Genetic engineering of DNA encoding full or truncated nanowire subunit forms. The truncations consist of stepwise codon reductions of the amino-terminus of the nanowire, to reduce the subunit hydrophobicity and improve its expression in a heterologous host. The truncations generally do not affect amino acids shown to be involved in electron transfer and metal binding and are optimized to preserve the subunit ability to assemble via hydrophobic interactions;

2) Application of recombinant techniques to fuse the truncated forms of the subunit to soluble carrier proteins to facilitate its expression in heterologous hosts such as *Escherichia coli* and subsequent recovery and purification of the subunit (so that it is substantially free of the carrier); and 3) In vitro assembly of the truncated subunit to produce filaments analogous to the native ones that have customizable structural and functional properties. Genetic engineering can also be used to add functional groups to the nanowire subunit, (e.g., for enhancing manufacture, folding, assembly, binding and other useful properties (e.g., including allowing synthesis of functionalized nanowires in nanostructured interfaces). This strategy enables versatile, customized development of nanowire-based products and processes for various applications.

In some embodiments, amino acids from the pilin subunits can be removed. For example, amino acids can be removed from a nanowire peptide to reduce the hydrophobicity of the peptide. Reducing the hydrophobicity of the nanowire peptides can, for example, facilitate manufacture or purification of the peptides.

Amino acids can be removed from the N-terminus or the C-terminus. In general, the N-terminus of nanowire peptides is more hydrophobic than the C-terminus, and the amino acids that participate in intramolecular and intermelocular electron transfer processes across and along the pilus nanowires are located closer to the C-terminus.

For example, in some embodiments, one or more amino acids are removed from the pilin subunit. In other embodiments, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty one or more, or twenty two or more amino acids are removed from a nanowire peptide.

A string of amino acids can also be removed from nanowire peptides. For example, a sequential segment of about 1 to about 4 amino acids can be removed, or a sequential segment of about 1 to about 5 amino acids can be removed, or a sequential segment of about 1 to about 7 amino acids can be removed, or a sequential segment of about 1 to about 10 amino acids can be removed, or a sequential segment of about 1 to about 12 amino acids can be removed, or a sequential segment of about 1 to about 14 amino acids can be removed, or a sequential segment of about 1 to about 15 amino acids can be removed, or a sequential segment of about 1 to about 16 amino acids can be removed, or a sequential segment of about 1 to about 17 amino acids can be removed, or a sequential segment of about 1 to about 18 amino acids can be removed, or a sequential segment of about 1 to about 19 amino acids can be removed, or a sequential segment of about 1 to about 20 amino acids can be removed, or a sequential segment of about 1 to about 21 amino acids can be removed, or a sequential segment of about 1 to about 22 amino acids can be removed, or a sequential segment of about 1 to about 23 amino acids can be removed, or a sequential segment of about 1 to about 24 amino acids can be removed, or a sequential segment of about 1 to about 25 amino acids can be removed.

Examples of nanowire peptides with amino acids removed from the N-terminus include, but are not limited to, those with ten or more amino acids removed. For example, a SEQ ID NO:26 peptide has about ten amino acids removed from the N-terminus (relative to the SEQ ID NO:9 nanowire peptide), and has the following sequence.

```
1    AIIGILAAIA IPQFSAYRVK AYNSAASSDL RNLKTALESA
41   FADDQTYPPE S
```

In another example, a SEQ ID NO:27 peptide has about nineteen amino acids removed from the N-terminus (relative to the SEQ ID NO:9 nanowire peptide), and has the following sequence.

```
1    AIPQFSAYRV KAYNSAASSD LRNLKTALES AFADDQTYPP
41   ES
```

In another example, a SEQ ID NO:28 peptide has about twenty amino acids removed from the N-terminus (relative to the SEQ ID NO:9 nanowire peptide), and has the following sequence.

```
1 IPQFSAYRVK AYNSAASSDL RNLKTALESA FADDQTYPPE S
```

In another example, a SEQ ID NO:29 peptide has about twenty two amino acids removed from the N-terminus (relative to the SEQ ID NO:9 nanowire peptide), and has the following sequence.

```
1   QFSAYRVKAY NSAASSDLRN LKTALESAFA DDQTYPPES
```

Therefore, in some embodiments, the pilin subunits are structurally modified. For example, hydrophobic amino acids can be removed as described herein to improve the solubility of the nanowire peptides, to minimize random aggregation of the nanowire peptides during or after recombinant production of the peptides, to facilitate production of the nanowire peptides, to facilitate the purification of the nanowire peptides, to improve the electrical conductivity of the nanowire peptides, to facilitate manufacture of nanowires from the nanowire peptides, to facilitate manufacture of fuel cells from the nanowire polypeptides, to facilitate manufacture of nanowire circuits, and the like. In other embodiments, the pili subunits are modified to alter the nanowires' surface chemical or functional properties.

For example, nanowire pilin subunits can be modified by genetic engineering. In one embodiment, the genetically engineered nanowire peptide is a modified nanowire peptide from *G. sulfurreducens*. In other embodiments, the genetically engineered microbial nanowire peptide is a modification of any of the SEQ ID NO: 1-10, 26-29 amino acid sequences. Such nanowire peptides can be modified using available recombinant technology procedures to generate mutant nanowire polypeptides with modified conductive, adhesive, coupling, solubility, folding or other properties.

The nanowires can include one or more peptide subunits with various molecular weights (MW). The subunits can have a variety of molecular weights ranging from, for example, at least about 3-kDa, or higher, or between about 3-kDa and about 25-kDa or between about 3-kDa and 20-kDa or between about 3-kDa and about 10-kDa or between about 4-kDa and about 9-kDa, or between about 5.5-kDa and about 7.5-kDa, including any range there between. In one embodiment, the subunit molecular weight is about 6.5-kDa or at least about 6.5-kDa. In one embodiment, nanowires formed by such peptide subunits do not contain metals, ions, contaminants, metalloenzymes, flavins or quinones.

As illustrated herein, the tyrosine and charged amino acids can contribute to the conductive function of the nanowires. In some embodiments, tryptophan may also contribute to the conductive function of the nanowires. Thus, to modulate the conductive function of the nanowires, the disclosed pilin subunits' amino acid sequences can be modified to include a greater or lesser proportion of the tyrosine, tryptophan or charged amino acids. In other embodiments, the position of the charged amino acids may be altered or varied.

Amino acid residues of the nanowires can be genetically encoded L-amino acids, naturally occurring non-genetically encoded L-amino acids, synthetic L-amino acids, D-enantiomers of any of the above and combinations of any of these amino acids. The amino acid notations used herein for the twenty genetically encoded L-amino acids and common non-encoded amino acids are conventional and are as shown in Table 1.

TABLE 1

| Amino Acid | One-Letter Symbol | Abbreviation |
|---|---|---|
| Alanine | A | Ala |
| Arginine | R | Arg |

TABLE 1-continued

| Amino Acid | One-Letter Symbol | Abbreviation |
|---|---|---|
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-Alanine | | bAla |
| 2,3-Diaminopropionic acid | | Dpr |
| α-Aminoisobutyric acid | | Aib |
| N-Methylglycine (sarcosine) | | MeGly |
| Ornithine | | Orn |
| Citrulline | | Cit |
| t-Butylalanine | | t-BuA |
| t-Butylglycine | | t-BuG |
| N-methylisoleucine | | MeIle |
| Phenylglycine | | Phg |
| Cyclohexylalanine | | Cha |
| Norleucine | | Nle |
| Naphthylalanine | | Nal |
| Pyridylalanine | | |
| 3-Benzothienyl alanine | | |
| 4-Chlorophenylalanine | | Phe(4-Cl) |
| 2-Fluorophenylalanine | | Phe(2-F) |
| 3-Fluorophenylalanine | | Phe(3-F) |
| 4-Fluorophenylalanine | | Phe(4-F) |
| Penicillamine | | Pen |
| 1,2,3,4-Tetrahydro-isoquinoline-3-carboxylic acid | | Tic |
| β-2-thienylalanine | | Thi |
| Methionine sulfoxide | | MSO |
| Homoarginine | | hArg |
| N-acetyl lysine | | AcLys |
| 2,4-Diamino butyric acid | | Dbu |
| P-Aminophenylalanine | | Phe(pNH$_2$) |
| N-methylvaline | | MeVal |
| Homocysteine | | hCys |
| Homoserine | | hSer |
| E-Amino hexanoic acid | | Aha |
| δ-Amino valeric acid | | Ava |
| 2,3-Diaminobutyric acid | | Dab |

The disclosed nanowire peptides and polypeptides include any of these amino acids and include mutant nanowire peptides having one or more of the amino acids within the SEQ ID NO:1-10, 26-29 sequences substituted with other, different amino acids.

While the substituted or replaced amino acid may have similar physical and chemical characteristics, it may also have different physical or chemical characteristics. For example, an amino acid from any of the SEQ ID NO:1-10, 26-29 nanowire sequences that has no direct role in electrical conductivity may be replaced by an amino acid that has a direct role in electrically conducting electrons along the pilus nanowire (e.g., a tyrosine or a charged amino acid). Alternatively, by way of example, an amino acid from any of the SEQ ID NO:1-10, 26-29 nanowire sequences that has a direct role in electrical conductivity may be replaced by an amino acid that has an indirect role in electrically conducting electrons along the pilus nanowires, or some other role such as adhesion, secondary or tertiary structure formation, and the like.

In general, amino acids can be placed into three main classes: hydrophilic amino acids, hydrophobic amino acids and cysteine-like amino acids, depending primarily on the characteristics of the amino acid side chain. These main classes may be further divided into subclasses. For example, some types of hydrophobic amino acids have aromatic side chains while other types of hydrophobic amino acids do not have aromatic side chains. Moreover, aromatic amino acids can have functional groups that provide a more hydrophilic character and that permit acceptance and transport of electrons (e.g., tyrosine). In general, the hydrophilic or aromatic amino acids have a more direct role in the electrical conductivity functions of the pilus nanowires.

Hydrophilic amino acids include amino acids having acidic, basic or uncharged polar side chains and hydrophobic amino acids include amino acids having apolar side chains. Apolar amino acids may be further subdivided to include, among others, aliphatic amino acids. As will be appreciated by those having skill in the art, the above classifications are not absolute. Several amino acids exhibit more than one characteristic property, and can therefore be included in more than one category. For example, tyrosine has both an aromatic ring and a polar hydroxyl group. Thus, tyrosine has dual properties and can be included in both the aromatic and polar categories. Similarly, in addition to being able to form disulfide linkages, cysteine also has an apolar character. Thus, while not strictly classified as a hydrophobic or an apolar amino acid, in many instances cysteine can be used to confer hydrophobicity to a peptide.

Certain commonly encountered amino acids that are not genetically encoded and that can be present, or substituted for an amino acid, in the disclosed peptides, peptide variants and peptide derivatives thereof include, but are not limited to, β-alanine (b-Ala) and other omega-amino acids such as 3-aminopropionic acid (Dap), 2,3-diaminopropionic acid (Dpr), 4-aminobutyric acid and so forth; α-aminoisobutyric acid (Aib); ∈-aminohexanoic acid (Aha); δ-aminovaleric acid (Ava); N-methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (MeVal); homocysteine (hCys) and homoserine (hSer). These amino acids also fall into the categories defined above.

The classifications of the above-described genetically encoded and non-encoded amino acids are summarized in Table 2, below. It is to be understood that Table 2 is for illustrative purposes only and does not purport to be an exhaustive list of amino acid residues that may comprise the peptides, variants and derivatives described herein. Other amino acid residues that are useful for making the peptides, peptide variants and peptide derivatives described herein can be found, e.g., in Fasman, 1989, *CRC Practical Handbook of Biochemistry and Molecular Biology*, CRC Press, Inc., and the references cited therein. Amino acids not specifically mentioned herein can be conveniently classified into the above-described categories on the basis of known behavior or their characteristic chemical or physical properties as compared with amino acids specifically identified.

TABLE 2

| Classification | Genetically Encoded | Genetically Non-Encoded |
|---|---|---|
| Hydrophobic | | |
| Aromatic | F, Y, W | Phg, Nal, Thi, Tic, Phe(4-Cl), Phe(2-F), Phe(3-F), Phe(4-F), Pyridyl Ala, Benzothienyl Ala |
| Apolar | M, G, P | Cha |
| Aliphatic | A, V, L, I | t-BuA, t-BuG, MeIle, Nle, MeVal, Cha, bAla, MeGly, Aib |
| Hydrophilic | | |
| Acidic | D, E | |
| Basic | H, K, R | Dpr, Orn, hArg, Phe(p-NH$_2$), DBU, A$_2$ BU |
| Polar | Q, N, S, T, Y | Cit, AcLys, MSO, hSer |
| Cysteine-Like | C | Pen, hCys, β-methyl-Cys |

Disclosed nanowire peptides that are modified to alter the nanowire's conductive properties can have any amino acid replaced by tyrosine, tryptophan, or a charged amino acid. In some embodiments, the disclosed nanowire peptides that are modified to alter the nanowire's conductive properties can have any tyrosine, tryptophan, or a charged amino acid within the nanowire peptide replaced by another amino acid.

Amino acid modifications that can diminish or abolish conductivity include single, double and triple replacements in tyrosines (e.g., replaced with alanine or the structurally-similar phenylalanine as shown herein) or positively and negatively charged amino acids.

Amino acid modifications that can increase conductivity include replacements that introduce additional tyrosines in optimum positions within the nanowire to promote electron transfer. Furthermore, replacements that result in structural changes that permit a more optimal electronic coupling between the electroactive amino acids (e.g., by bringing them closer together) can also be used because they may increase the rates of electron hopping. These amino acids can be those directly involved in the electron transfer, such as tyrosines, those serving as protonating or proton-accepting residues, or those that preserve the optimal nanowire structure and mechanical properties to promote electron transfer.

In addition, amino acids carrying post-translational modifications such as glycosylation, acylation or phosphorylation can be also introduced or replaced to manipulate the binding and adhesive properties of the nanowires, the charge of the nanowires and the electronic behavior of the nanowires. Amino acids that are post-translationally modified can be replaced, added, or used instead of an existing amino acid within any of the SEQ ID NOS:1-10, 26-29 peptides. For example, an amino acid subject to posttranslational modification, such as phosphorylation, glycosylation or acylation, can be used instead of an existing amino acid within any of SEQ ID NO:1-10, 26-29.

In some embodiments, an amino acid that is not post-translationally modified can be replaced with another amino acid that is post-translationally modified. In some embodiments, the amino acid is replaced with a similarly classified amino acid to minimize changes in the secondary or tertiary structure of the nanowire peptide.

In some embodiments, a cysteine or cysteine-like amino acid is added to a nanowire peptide having a sequence like any of SEQ ID NO:1-10, 26-29. In other embodiments, the cysteine or cysteine-like amino acid is used instead of an amino acid present in a nanowire peptide having a sequence like any of SEQ ID NO:1-10, 26-29. Such a cysteine or cysteine-like amino acid is useful for enhancing the binding or adhesion properties of the nanowire peptide. In one embodiment, placement or addition of cysteine in nanowire peptides is used to facilitate electrical coupling of the nanowire peptide to substrates (such as gold or carbon or a suitable support). In some embodiments, the cysteine or cysteine-like amino acid is placed within or near the N-terminal region of the nanowire sequence.

In some embodiments, the disclosed nanowire peptides have a signal sequence; in other embodiments, the nanowire peptides do not have a signal sequence.

In some embodiments, the nanowire peptides are selected from the following group: (1) a peptide having an amino acid sequence as shown in any of SEQ ID NO:1-10, 26-29; or (2) a peptide having an amino acid sequence with at least 70% identity to that of any of SEQ ID NO:1-10, 26-29, assembling into a polypeptide having conductive function or activity comparable to a polypeptide formed with peptides of (1); or (3) a functional fragment, variant, analog or derivative of the peptide of (1) or (2), assembling into a polypeptide having substantially the same biological function or activity compared to that of the polypeptide formed with peptides (1) or (2). In some embodiments, the nanowire peptides contain an amino acid sequence with identity of at least 75%, or at least 80%, preferably at least 85%, preferably at least 90%, preferably at least 95%, more preferably at least 96%, at least 97%, at least 98% or at least 99% relative to any of SEQ ID NO:1-10, 26-29.

The pilus nanowires are described further in the Examples. As described herein, the nanowire peptides and polypeptides disclosed herein, can self-assemble and are electrically conductive.

Nucleic acids encoding nanowire peptides are useful for recombinant expression of large amounts of unmodified and modified nanowire peptides and polypeptides. Nucleic acids encoding modified nanowire peptides can be generated from nucleic acids encoding the naturally-occurring nanowire peptides (e.g., from pilA nucleic acids) using methods known to those of skilled in the art.

Any available nanowire nucleic acid can form the basis for generating mutant nucleic acids that encode nanowires with modified properties. For example, Geobacteraceae bacteria naturally produce nanowire protein filaments that are electrically conductive. Hence, Geobacteraceae bacteria are one source of nanowire nucleic acids. Natural nucleic acid sequences, such those encoding the SEQ ID NO:1-10, 26-29 nanowire peptides, can act as a basis for generating modified nanowire peptides. Naturally-occurring nanowire nucleic acid and amino acid sequences are also available in public sequence databases such as those provided by the National Center for Biotechnology Information (NCBI) database (see, e.g., www.ncbi.nlm.nih.gov).

For example, the SEQ ID NO:9, 10, 26-29 nanowire peptides are encoded by the following pilA nucleic acid sequence (SEQ ID NO:11), which can be used to generate mutant nanowire nucleic acids.

In some of the embodiments, the nucleic acids that encode nanowire peptides have sequence identity with the SEQ ID NO:11 nucleic acid sequence of at least 70%, at least 75%, at least 80%, at least 85%, at least 90%, at least 95%, at least 96%, at least 97%, at least 98% or at least 99% sequence identity.

For example, nucleic acids can readily be generated that encode mutant nanowire peptides, where in some embodiments, the mutant nucleic acids encode nanowire peptides that include less than the three tyrosine amino acids at positions 27, 32 and 57 of the SEQ ID NO:9 nanowire peptide. Such "tyrosine-deficient" nanowire peptides have reduced conductivity, as illustrated herein. In other embodiments, the mutant nucleic acids encode nanowire peptides that include more than the three tyrosine amino acid residues at amino acid positions 27, 32 or 57. Such "tyrosine-rich'" nanowire peptides can have increased conductivity. In some embodiments, the mutant nanowire peptides have 2, 3, 4, 5, 6, 7, 8, 9, 10, 11, 12, 13 or 14 tyrosine residues.

In some embodiments, the mutant nucleic acids encode nanowire peptides that include fewer negatively charged amino acids than are typically present at positions 5, 39, 48, 53, 54 and 60 of the SEQ ID NO:9 nanowire peptide. In other embodiments, the mutant nucleic acids encode nanowire peptides that include more negatively charged amino acids than are typically present at positions 5, 39, 48, 53, 54 and 60 of the SEQ ID NO:9 nanowire peptide. Thus, the mutant nanowire peptides can, for example, have 3, 4, 5, 6, 7, 8, 9, 10, 11, 12, 13 or 14 negatively charged amino acids (e.g., aspartic acid or glutamic acid).

In some embodiments, the mutant nucleic acids encode nanowire peptides that include fewer positively charged amino acids than are typically present at positions 28, 30, 41 and 44 of the SEQ ID NO:9 nanowire peptide. In other embodiments, the mutant nucleic acids encode nanowire peptides that include more positively charged amino acids than are typically present at positions 28, 30, 41 and 44 of the SEQ ID NO:9 nanowire peptide. Thus, the mutant nanowire peptides can, for example, have 2, 3, 4, 5, 6, 7, 8, 9, 10, 11, 12, 13 or 14 positively charged amino acids (e.g., aspartic acid or glutamic acid).

In many embodiments, the modified nanowire peptides recombinantly generated from the mutant nucleic acids have substantially the same secondary or tertiary structure(s) as naturally occurring nanowire peptides (e.g., the SEQ ID NO:1-10 peptides).

Methods for isolating nucleic acids encoding the naturally-occurring nanowires, as well as technologies for generation of nucleic acids encoding modified nanowire peptides are available in the art. See, for example, CURRENT PROTOCOLS IN MOLECULAR BIOLOGY, Ausubel et al. eds. (John Wiley & Sons, Inc., 1999), or MOLECULAR CLONING: A LABORATORY MANUAL, Sambrook et al. (Cold Spring Harbor Laboratory Press, New York, 1989), or MOLECULAR CLONING: A LABORATORY MANUAL, Sambrook et al. (Cold Spring Harbor Laboratory Press, New York, 2001). Nucleic acids encoding mutant nanowire peptides containing various amino acid substitutions can be produced by site-specific mutagenesis and polymerase chain reaction (PCR) amplification from the nucleic acids encoding the naturally-occurring pilin. Stratagene provides a QuikChange mutagenesis kit that can be used for such mutagenesis. Complementary primers containing mutagenic nucleotides can be employed such as those described in the Examples provided herein. Mutant nucleic acids that encode such modified nanowires can be produced, for example, by polymerase chain reaction (PCR) using primers that encode the desired sequence.

In some embodiments, the disclosed nucleic acid encodes a nanowire peptide selected from the following group: (1) a peptide having an amino acid sequence as shown in any of SEQ ID NO:1-10, 26-29; or (2) a peptide having an amino acid sequence with at least 40% sequence identity to that of any of SEQ ID NO:1-10, 26-29 that forms a polypeptide having conductive function or activity comparable to that of the polypeptide formed from the peptides of (1); or (3) a functional fragment, variant, analog or derivative of the peptide of (1) or (2), that produces nanowire polypeptides having substantially the same biological function or activity as polypeptides formed with the peptide of (1) or (2). Thus, the nucleic acids include: (a) polynucleotides that code the PilA polypeptides of (1), (2) or (3) above; (b) polynucleotides that are hybridized with, under low, medium or high stringent conditions, and have at least 40% of sequence identity compared to the polynucleotides of (a); and (c) polynucleotide fragments that contain polynucleotides as described in (a) and (b).

Stringent conditions are somewhat sequence-dependent and can vary in different circumstances. By controlling the stringency of the hybridization or washing conditions, target sequences can be identified which can be up to 100% complementarity to the probe (homologous probing). Alternatively, stringency conditions can be adjusted to allow some mismatching in sequences so that lower degrees of similarity are detected (heterologous probing). The probe can be approximately 20-500 nucleotides in length, but can vary greatly in length from about 18 nucleotides to equal to the entire length of the target sequence. In some embodiments, the probe is about 10-50 nucleotides in length, or about 18-25 nucleotides in length, or about 18-50 nucleotides in length, or about 18-100 nucleotides in length. In some embodiments, the probe is a full length nucleic acid with SEQ ID NO:11 (which has 216 nucleotides), or a fragment thereof.

Typically, stringent conditions will be those where the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1M NaCl, 1% SDS (sodium dodecyl sulfate) at 37° C., and a wash in 1× Saline Sodium Citrate (SSC) to 2×SSC (where 20×SSC is 3.0 M NaCl, 0.3 M trisodium citrate) at 50 to 55° C. Exemplary moderate stringency conditions include hybridization in 40 to 45% formamide, 1M NaCl, 1% SDS at 37° C., and a wash in 0.5×SSC to 1×SSC at 55 to 60° C. Exemplary high stringency conditions include hybridization in 50% formamide, 1M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl (*Anal. Biochem.* 138:267-84 (1984)) as follows:

$$T_m=81.5° C.+16.6(\log M)+0.41(\% GC)-0.61(\% \text{formamide})-500/L$$

where M is the molarity of monovalent cations; % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. The $T_m$ is reduced by about 1° C. for each 1% of mismatching. Thus, the thermal melting point ($T_m$), hybridization or wash conditions can be adjusted to hybridize to sequences of the desired identity. For example, if sequences with greater than or equal to 90% sequence identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization or wash at 1, 2, 3 or 4° C. lower than the thermal melting point ($T_m$). Moderately stringent conditions can utilize a hybridization or a wash at 6, 7, 8, 9 or 10° C. lower than the thermal melting point ($T_m$). Low stringency conditions can utilize a hybridization or wash at 11, 12, 13, 14, 15 or 20° C. lower than the thermal melting point ($T_m$). Using the equation, hybridization and wash compositions, and desired $T_m$, those of ordinary skill can identify and isolate nucleic acids with sequences related to SEQ ID NO:1-10, 26-29. Those of skill in the art also understand how to vary the hybridization or wash solutions. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, LABORATORY TECHNIQUES IN BIOCHEMISTRY AND MOLECULAR BIOLOGY—HYBRIDIZATION WITH NUCLEIC ACID PROBES, part 1, chapter 2, "Overview of principles of hybridization and the strategy of nucleic acid probe assays," Elsevier, N.Y. (1993); and CURRENT PROTOCOLS IN MOLECULAR BIOLOGY, chapter 2, Ausubel, et al., eds, Greene Publishing and Wiley-Interscience, New York (1995). Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

The reference sequence can be a nucleic acid sequence (e.g., SEQ ID NO:11) or an amino acid sequence (e.g., any of SEQ ID NO:1-10, 26-29). A reference sequence may be a subset or the entirety of a specified sequence; for example, as a segment of a full-length cDNA or genomic DNA sequence, or the complete cDNA or genomic DNA sequence, or a domain of a peptide or protein sequence.

Exemplary comparison window for nucleic acids is at least 20 contiguous nucleotides in length, and optionally can be 30, 40, 50, 100 or more nucleotides. For amino acid sequences, the comparison window is at least about 15 amino acids, and can optionally be 20, 30, 40, 50, 100 or more amino acids. Those of skill in the art understand that to avoid a high similarity to a reference sequence due to inclusion of gaps in the nucleic acid or amino acid sequence a gap penalty is typically introduced and is subtracted from the number of matches.

Exemplary alignment of nucleotide and amino acid sequence methods for comparison include the local homology algorithm (BESTFIT) of Smith and Waterman, (1981) *Adv. Appl. Math* 2:482, may conduct optimal alignment of sequences for comparison; by the homology alignment algorithm (GAP) of Needleman and Wunsch, (1970) *J. Mol. Biol.* 48:443-53; by the search for similarity method (Tfasta and Fasta) of Pearson and Lipman, (1988) *Proc. Natl. Acad. Sci. USA* 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package, Version 8 (available from Genetics Computer Group (GCG™ programs (Accelrys, Inc., San Diego, Calif.)). The CLUSTAL program is well described by Higgins and Sharp, (1988) *Gene* 73:237-44; Higgins and Sharp, (1989) CABIOS 5:151-3; Corpet, et al., (1988) *Nucleic Acids Res.* 16:10881-90; Huang, et al., (1992) Computer Applications in the Biosciences 8:155-65 and Pearson, et al., (1994) *Meth. Mol. Biol.* 24:307-31. The preferred program to use for optimal global alignment of multiple sequences is PileUp (Feng and Doolittle, (1987) *J. Mol. Evol.,* 25:351-60 which is similar to the method described by Higgins and Sharp, (1989) CABIOS 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology,* Chapter 19, Ausubel, et al., eds., Greene Publishing and Wiley-Interscience, New York (1995).

GAP uses the algorithm of Needleman and Wunsch, (1970) *J. Mol. Biol.* 48:443-53, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) *Proc. Natl. Acad. Sci. USA* 89:10915).

Unless otherwise stated, sequence identity/similarity values provided herein refer to the value obtained using the BLAST 2.0 suite of programs using default parameters (Altschul, et al., (1997) *Nucleic Acids Res.* 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen (1993) *Comput. Chem.* 17:149-63) and XNU (C.sub.1-ayerie and States, (1993) *Comput. Chem.* 17:191-201) low-complexity filters can be employed alone or in combination.

A peptide, protein or nucleic acid may have a sequence with between 55-100% sequence identity to a reference sequence, at least 55% sequence identity, 60%, 70%, 80%, at least 90% or 95% sequence identity to the reference sequence over a specified comparison window. The reference sequence can, for example, be any of the SEQ ID NO:1-10, 26-29 nanowire peptides or the SEQ ID NO:11 nanowire nucleic acid. Optimal alignment may be ascertained or conducted using the homology alignment algorithm of Needleman and Wunsch, supra.

Nucleic acids encoding nanowire peptides can be used for recombinant expression of the nanowire peptides, for example, by operably-linking the nanowire nucleic acid to an expression control sequence within an expression vector, which can be introduced into a host cell for expression of the encoded peptide. The nucleic acids that encode nanowire peptides can also encode a fusion partner fused in-frame with the nanowire peptide, for example, to facilitate expression or purification of the nanowire peptide.

Expression vectors contain appropriate expression control sequences that direct expression of a nucleic acid that is operably linked to the expression control sequence to produce a transcript. The product of that expression is referred to as a messenger ribose nucleic acid (mRNA) transcript. The expression vector may also include other sequences such as enhancer sequences, synthetic introns, and polyadenylation and transcriptional termination sequences to improve or optimize expression of the nucleic acid encoding the nanowire peptide.

The nanowire nucleic acid(s) can be optimized for expression in a selected prokaryotic (e.g., bacterial) or eukaryotic cell. As is known to one of skill in the art, a particular type of bacterial or animal species may have a different set of preferred codons than another type of species. Use of codons that are preferred by a host cell can facilitate expression of the nanowire peptides. Optimized sequences include sequences that are codon optimized to include codons that are employed more frequently in one organism relative to another organism, as well as modifications to add or modify Kozak sequences, to add or remove introns, or to remove undesirable sequences, for instance, potential transcription factor binding sites.

In one embodiment, a nucleic acid sequence encoding a nanowire peptide is optimized by replacing codons in a nanowire nucleic acid with codons that encode the same (or similar) amino acid but are preferentially employed in a particular (selected) cell. Preferred codons have a relatively high codon usage frequency in a selected cell (e.g., a bacterial, yeast or animal cell) and are translated more efficiently. Introduction of preferred codons can also result in the introduction of only selected transcription factor binding sites for transcription factors present in the selected host cell, and relatively few other undesirable structural attributes. Thus, the optimized nucleic acid product has an improved level of expression due to improved codon usage frequency, and a reduced risk of inappropriate transcriptional behavior due to a reduced number of undesirable transcription regulatory sequences.

In one embodiment, the optimized nucleic acid no longer hybridizes to the corresponding non-optimized sequence, e.g., does not hybridize to the non-optimized sequence under medium or high stringency conditions. However, in most embodiments, the optimized nucleic acid does hybridize to the corresponding non-optimized sequence under medium or high stringency conditions. In another embodiment, the nucleic acid has less than 90%, e.g., less than 80%, nucleic acid sequence identity to the corresponding non-optimized sequence and optionally encodes a peptide having at least 80%, e.g., at least 85%, 90%, 91%, 92%, 93%, 94%, 95%, 96%, 97%, 98% or more, amino acid sequence identity with the peptide encoded by the non-optimized sequence.

An isolated and optimized nucleic acid molecule of the disclosed sequences may have a codon composition that differs from that of the corresponding wild type nucleic acid sequence at more than 30%, 35%, 40% or more than 45%, e.g., 50%, 55%, 60% or more of the codons. For example, when a non-bacterial host cell is used, the preferred codons are those that are employed more frequently in a selected non-bacterial host cell species than, for example, in the genome of a *Geobacter* species. In general, preferred codons do not include codons that are infrequently used in the selected organism or cell type. Preferred codons for different organisms are known to the art, e.g., see www.kazusa.or.jp./codon/. In one embodiment, the majority of the codons that differ are ones that are preferred codons in a desired host cell.

A nucleic acid molecule encoding a nanowire peptide can optionally be optimized for expression in a particular host cell and then operably linked to one or more transcription regulatory sequences, e.g., a promoter, one or more enhancers, a transcription termination sequence or a combination thereof, to form an expression cassette.

The nanowire peptides can also be expressed as fusion proteins. To express the nanowire peptide(s) as a fusion protein, the nucleic acids that encode the nanowire peptide can also encode a fusion partner fused in-frame with the nanowire peptide. For example, fusion expression systems that have been include use of fusion partner peptides such as a His tag (allowing purification on a Nickel column; Clontech Laboratories, Inc., Qiagen, Life Technologies Corp.); a MalE maltose binding protein, (New England Biolabs, allowing purification on an amylose column); a thioredoxin (allowing purification with a phenyl arsine oxide resin); a glutathione-S-transferase (GST, allowing purification with glutathione) and a chitin binding domain (allowing purification with chitin columns, New England Biolabs). By also encoding a signal peptide in-frame with the fusion protein some of these systems (e.g., MalE, His Tag™ (Roche)) can be adapted for periplasmic expression. Cytoplasmic expression can be achieved with these systems when no signal peptide is incorporated. The expressed fusion protein can contain a specific protease cleavage site for cleavage and removal of the fusion partner peptide.

As illustrated herein, the type of fusion partner peptide can influence the ease or extent of expression and purification. For example, some types of fusion partner peptides may interfere with, or promote folding, aggregation, degradation, or solubility of the fusion protein. In general, a fusion partner peptide is selected that facilitates fusion protein expression, folding, solubility, purification or any combination thereof. In some embodiments, the fusion partner peptide can protect the fusion protein from proteolytic digestion, or inhibit proteolytic degradation.

One example of a fusion partner peptide that is useful for expression and production of a nanowire peptide is the chitin binding domain (CBD). The small size (about 5-7 kDa), substrate binding specificity and high avidity of CBDs for chitin has led to their utilization as affinity tags for immobilization of proteins to chitin surfaces (Bernard, M. P., et al. *Anal. Biochem.* 327:278-283 (2004); Ferrandon, S., et al. *Biochim. Biophys. Acta.* 1621: 31-40 (2003)). For example, the *B. circulans* chitinase A1 type 3 CBD has been used to immobilize fusion proteins expressed in bacteria on chitin beads to provide a platform for intein-mediated protein splicing (Ferrandon, S., et al., *Biochim. Biophys. Acta.* 1621: 31-40 (2003)) and to chitin-coated microtiter dishes (Bernard, M. P., et al., *Anal. Biochem.* 327:278-283 (2004)).

CBD as a component of chitinase can be obtained from many different sources, for example, fungi, bacteria, plants and insects. Any CBD originating from a chitinase may be used herein although CBDs separated from chitinase catalytic activity are preferred.

A sequence for amino acids to 470-551 from the wild-type chitin binding domain of *Kluyveromyces lactis* has the following sequence (SEQ ID NO:16).

```
 1    DSWAVTRAKE LNEQFVKGEL NGKDSCSDGE ISCTADGKIA
41    ICNYGAWVYT ECAAGTTCFA YDSGDSVYTS CNFTYLKPDV
81    VF
```

A mutant *Kluyveromyces lactis* chitin binding domain with good chitin binding and release properties has the following sequence (SEQ ID NO:17).

```
 1    DSWAVTRAKE LNEQFVKGEL NGKDSCSDGE ISCTADGKIA
41    ICNYGAWVYT ECAASTTCFA YDSGDSVYTS CNLLI
```

The fusion protein is generated by ligating a nucleic acid encoding the fusion partner peptide in-frame with a nucleic acid encoding the nanowire peptide. Methods available in the art can be used for such ligation. For example, construction of fusion proteins and use of fusion partner peptides is described in more detail in U.S. Pat. Nos. 7,732,565; 6,897,285; 6,987,007; 7,060,465; 6,984,505; 7,001,745; 7,271,256; 7,517,671; 5,834,247; and in published patent applications US20060035333; US20030216550; US20050196841; US20060030008; US20050196804; US20060199225; US20110071280; US20070099234; US20070065880; US20110097737; US20100167942; WO/2003/074660A2; WO/2001/057183A2; WO/2006/041849A2; and WO/2009/026089A1, all of which are specifically incorporated herein by reference in their entireties.

Nucleic acids encoding nanowire peptides (or fusion proteins) can be incorporated into bacterial, viral, insect, yeast or mammalian expression vectors so that they are operably-linked to expression control sequences such as bacterial, viral, insect, yeast or mammalian promoters (or enhancers).

Nucleic acid molecules or expression cassette that encode nanowire peptides (or fusion proteins) may be introduced to a vector, e.g., a plasmid or viral vector, which optionally includes a selectable marker gene, and the vector introduced to a cell of interest, for example, a bacterial, yeast or mammalian host cell.

Examples of host cells useful for manufacture nanowire peptides and polypeptides include, but are not limited to, *E. coli, Salmonella* species, *Bacillus* species, *Streptomyces* species, and the like), plant cells (e.g., *Arabidopsis* species, *Taxus* species, *Catharanthus* species, *Nicotiana* species,

*Oryza* species, soybeans, alfalfa, tomatoes, and the like), fungal cells (e.g., *Kluyveromyces* species, *Saccharomyces* species, *Pichia* species, *Hansenula* species, *Yarrowia* species, *Neurospora* species, *Aspergillus* species, *Penicillium* species, *Candida* species, *Schizosaccharomyces* species, *Cryptococcus* species, *Coprinus* species, *Ustilago* species, *Magnaporth* species, *Trichoderma* species, and the like), insect cells (e.g., Sf9 cells, Sf12 cells, *Trichoplusia* ni cells, *Drosophila* species and the like), or mammalian cells (e.g., primary cell lines, HeLa cells, NSO cells, BHK cells, HEK-293 cells, PER-C6 cells, and the like). These cells may be grown in cultures ranging from microliter volumes to multiliter volumes.

In some embodiments, the vector may be maintained, manipulated, expanded or replicated in a prokaryotic cell such as a cell from the family Geobacteraceae or a cell from the genus *Geobacter*. In other embodiments, the vector may be maintained, manipulated, expanded or replicated in a prokaryotic cell such as an *E. coli, Streptomyces* spp., *Bacillus* spp., *Staphylococcus* spp. and the like. In further embodiments, the vector may be maintained, manipulated, expanded or replicated in a eukaryotic cell such as a yeast or mammalian cell.

Expression cassettes or vectors containing nucleic acids encoding nanowire peptides can be introduced into bacterial, insect, yeast or mammalian host cells for expression using conventional methods including, without limitation, transformation, transduction and transfection. In some embodiments, the host cell also has genes encoding components of the pilus secretory apparatus or a pilB or pilT gene, which may facilitate, respectively, assembly of the nanowire peptides or extension of the nanowire polypeptide or retraction of the nanowire polypeptide(s). In other embodiments, the host cell has no pilT gene, or carries a deletion in the pilT gene, to inhibit retraction of the nanowire polypeptide(s) and facilitate assembly of the nanowire filament.

The expression of the encoded nanowire protein may be controlled by any promoter capable of expression in prokaryotic cells or eukaryotic cells. Examples of prokaryotic promoters that can be used include, but are not limited to, SP6, T7, T5, tac, bla, trp, gal, lac or maltose promoters. Examples of eukaryotic promoters that can be used include, but are not limited to, constitutive promoters, e.g., viral promoters such as cytomegalovirus (CMV), SV40 and RSV promoters, as well as regulatable promoters, e.g., an inducible or repressible promoter such as the tet promoter, the hsp70 promoter and a synthetic promoter regulated by CRE. Vectors for bacterial expression include pGEX-5X-3, and for eukaryotic expression include pCIneo-CMV. In some embodiments, the expression vector is the pRG5 vector (Coppi et al., *Appl. Environ. Microbiol.* 67: 3180-87 (2001)); Leang et al., *BMC Genomics* 10, 331 (2009).

In many embodiments, the nanowire peptides are expressed in a bacterial host cell. Plasmid vectors containing bacterial replicon and control sequences are typically used for expression in a bacterial host cell. The vector ordinarily carries a replication site, as well as marking sequences that are capable of providing phenotypic selection in transformed cells. For example, *E. coli* is typically transformed using pBR322, a plasmid derived from an *E. coli* species. See, e.g., Bolivar et al., *Gene* 2: 95 (1977). pBR322 contains genes conferring ampicillin and tetracycline resistance and thus provides an easy means for identifying transformed cells. The pBR322 plasmid, or other microbial plasmid or phage, also generally contains, or is modified to contain, promoters that can be used by the bacterial organism for expression of the selectable marker genes.

Bacterial expression vectors for producing nanowire peptides can also contain an inducible promoter that is recognized by the host bacterial organism and is operably linked to the nucleic acid encoding the peptide(s) of interest. It can also contain a separate promoter, which may be inducible or of low basal expression, operably linked to the nucleic acid encoding the phage lysozyme. Inducible promoters suitable for use with bacterial hosts include the β-lactamase and lactose promoter systems (Chang et al., *Nature* 275: 615 (1978); Goeddel et al., *Nature* 281: 544 (1979)), the arabinose promoter system, including the araBAD promoter (Guzman et al., *J. Bacteriol.* 174: 7716-7728 (1992); Guzman et al., *J. Bacteriol.* 177: 4121-4130 (1995); Siegele and Hu, *Proc. Natl. Acad. Sci. USA,* 94: 8168-8172 (1997)), the rhamnose promoter (Haldimann et al., *J. Bacteriol.,* 180: 1277-1286 (1998)), the alkaline phosphatase promoter, a tryptophan (trp) promoter system (Goeddel, *Nucleic Acids Res.,* 8: 4057 (1980) and EP 36,776), the $P_{LtetO-1}$ and $P_{lac/ara-1}$ promoters (Lutz and Bujard, *Nucleic Acids Res.,* 25: 1203-1210 (1997)), and hybrid promoters such as the tac promoter (deBoer et al., *Proc. Natl. Acad. Sci. USA,* 80: 21-25 (1983)). However, other bacterial inducible and low-basal-expression promoters are suitable, including promoter nucleotide sequences that have been published, thereby enabling a skilled worker operably to ligate them to DNA encoding the peptide of interest using linkers or adaptors to supply any required restriction sites. For example, a strong and highly leaky promoter, such as the trp promoter, can be employed. The phage lambda $P_L$ promoter or the alkaline phosphatase promoter can also be used.

Promoters for use in bacterial systems also generally contain a Shine-Dalgarno (S.D.) sequence operably linked to the DNA encoding the peptide of interest. The promoter can be removed from the bacterial source DNA by restriction enzyme digestion and inserted into the vector containing the desired DNA. The phoA promoter can be removed from the bacterial-source DNA by restriction enzyme digestion and inserted into the vector containing the desired DNA.

The nucleic acid encoding the nanowire peptide may contain a signal sequence, such as one at the N-terminus of the mature peptide. The signal sequence may be a component of the vector, or it may be a part of the peptide nucleic acid that is inserted into the vector. If a heterologous signal sequence is selected it should be one that is recognized and processed (i.e., cleaved by a signal peptidase) by the host cell.

Expression vectors contain a nucleic acid sequence that enables the vector to replicate in one or more selected host cells. Such sequences are well known for a variety of bacteria. The origin of replication from the plasmid pBR322 is suitable for most Gram-negative bacteria.

Expression vectors can also contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for bacilli. One example of a selection scheme utilizes a drug to arrest growth of a host cell. Those cells that are successfully transformed with a heterologous gene produce a protein conferring drug resistance and thus survive the selection regimen.

Construction of suitable vectors containing one or more of the above-listed components employs standard ligation techniques. Isolated plasmids or DNA fragments are cleaved, tailored, and re-ligated in the form desired to generate the plasmids required. For analysis to confirm correct sequences in plasmids constructed, the ligation mixtures can be transformed into *Geobacter, E. coli* K12 strain 294 (e.g., ATCC 31,446), or other strains, and successful transformants are selected. Plasmids from the transformants can be prepared, analyzed by restriction endonuclease digestion, or sequenced by available procedures.

The nanowire nucleic acid molecule, expression cassette or vector of the can be introduced into a cell by any method including, but not limited to, calcium-mediated transformation, electroporation, microinjection, lipofection, particle bombardment and the like.

Suitable bacteria for expression of the nanowire peptides include host cells that also have or are modified to include a pilT gene. Such host cells include, for example, archeabacteria and bacteria, especially Gram-negative bacteria. For example, Gram-negative bacteria such as Geobacteraceae or Enterobacteriaceae can be utilized as host cells. Examples of useful bacteria include, but are not limited to, *Geobacter, Escherichia, Enterobacter, Azotobacter, Erwinia, Bacillus, Pseudomonas, Klebsiella, Proteus, Salmonella, Serratia, Shigella, Rhizobia, Vitreoscilla*, and *Paracoccus*. Suitable *E. coli* hosts include *E. coli* W3110 (ATCC 27,325), *E. coli* 294 (ATCC 31,446), *E. coli* B, and *E. coli* X1776 (ATCC 31,537). These examples are illustrative rather than limiting. Mutant cells of any of the above-mentioned bacteria may also be employed. It is, of course, necessary to select the appropriate bacteria taking into consideration replicability of the replicon in the cells of a bacterium. For example, *Geobacter, E. coli, Serratia*, or *Salmonella* species can be suitably used as the host cells when well-known plasmids such as pBR322, pBR325, pACYC 177, or pKN410 are used to supply the replicon.

The host cells containing the nanowire nucleic acid(s) can be grown and multiplied in culture using available procedures and cell culture conditions. In some embodiments, pilus nanowires are produced by Geobacteraceae bacteria that have the pilB gene and the pilT gene (or, alternatively, a deletion of an endogenous pilT gene). The culture medium can be a Fresh Water (FW) medium with acetate and fumarate, which is described by Reguera et al. (NATURE 435: 1098-1101 (2005); Reguera et al., J. BACTERIOL. 189: 2125-27 (2007); U.S. Pat. No. 7,498,155, which are herein incorporated by reference in their entireties). The host cells can be cultured at different temperatures, for example, at 20-30° C. (e.g., 25° C.).

The nanowires can be purified by any available method. In one embodiment, the method includes lysis of cells expressing the nanowires, followed by selective removal of contaminating cell macromolecules, and then selective separation of pure nanowires from other proteins. In one embodiment, a single step purification method is used which may have yields in excess of 50%, such as up to 55% or up to 60% or higher, including any and all ranges there between. In one embodiment, the yield is at least about 63%. Higher yields, in excess of 63% may also be possible, such as up to about 95%, including any and all ranges there between. The protocol is flexible, in the sense that it can be adapted for use with substantially any sample of pili-expressing cells, substantially any method to remove contaminating cell macromolecules that do not affect the integrity of the nanowires, and substantially any method to selectively separate the nanowires from other contaminating proteins based on the nanowires' unique attributes.

For example, when the nanowire peptides are expressed as fusion proteins, they can be purified from culture media or lysate by binding to ligand or binding entity that specifically binds to the fusion partner peptide. In one embodiment, the host cells are used to express the nanowires which are then purified to obtain intact nanowires. In other embodiments, the host cells are used to mass-produce the pilin peptide and then purified for self-assembly of the nanowires or pili. In some embodiments, the fusion partner peptide is a chitin binding domain. When the fusion partner peptide is a chitin binding domain, a matrix or solid substrate containing a carbohydrate can be used, where the carbohydrate is bound by the chitin binding domain. For example, the chitin binding domain(s) can bind chitin. Chitin can be linked, adsorbed or covalently bound to a solid substrate such as a bead, column matrix or a coated surface. The solid substrate may, for example, magnetic chitin beads, colloidal chitin or environmental chitin. The chitin may also be immobilized in a column or coated on a solid surface. In one example, sterile chitin beads are added directly to culture medium so that protein production and harvesting can occur simultaneously during the fermentation process (see, e.g., U.S. Pat. No. 7,732,565 or U.S. Patent Application Publication. No. 2006/041849, both of which are hereby incorporated by reference herein in their entireties).

Once the solid substrate (e.g., beads, matrix or a column) has been washed to remove contaminating molecules, the nanowire peptide can be obtained by cleaving a bond linking the nanowire peptide to the fusion partner peptide, then washing the nanowire peptide from the solid substrate, leaving the fusion partner peptide attached to the solid substrate. It is desirable to elute the nanowire peptide from the matrix under non-denaturing conditions.

In some embodiments, an IMPACT-CN™ Protein Fusion and Purification System from New England Biolabs Inc. can be used. This system contains four expression vectors (pTYB vectors) that allow fusion of a bifunctional tag, consisting of the intein and the chitin binding domain, to either the C-terminus (pTYB1,2) or N-terminus (pTYB11, 12) of the nanowire peptide (see website at neb.com/nebecomm/products/productE6900.asp). In the presence of thiols such as dithiothreitol (DTT), β-mercaptoethanol or cysteine, the intein undergoes specific self-cleavage which releases the target protein from the chitin-bound intein tag. A nucleic acid encoding the nanowire peptide can be inserted into the IMPACT-CN™ pTYB1 and pTYB11 expression vectors that contain a SapI cloning site, which allows the nanowire peptide to be cloned immediately adjacent to the cleavage site of the intein tag. This results in the purification of the nanowire peptide without any extra non-native residues attached to its terminus after cleavage. In contrast, use of pTYB2 or pTYB12 yields a nanowire peptide with extra residue(s) added to its C-terminus or N-terminus, respectively. Addition of extra residues may help the cleavage reaction for some proteins. pTYB2 and pTYB12 contain the same or compatible restriction sites in the multiple cloning region. This allows cloning the nanowire peptide nucleic acid into both vectors. pTYB1 and pTYB2 use the ATG of the NdeI site in the multiple cloning region for translation initiation.

After construction of an expression vector, it can be incorporated into a host cell and expressed using available procedures. For example, any of the procedures described herein can be used for introducing the expression vector into a host cell and expressing the fusion protein. When a desired amount or level of fusion protein is expressed, the host cells can be lysed. The host cell lysate, including the fusion protein, can be subjected to a purification procedure, for example, an affinity purification procedure.

For example, a fusion protein that includes a fusion partner peptide that binds to a binding entity can be affinity purified by contacting the fusion protein with a solid substrate to which the binding entity is absorbed or bound. After binding to the fusion protein to a solid substrate, the fusion partner peptide can be cleaved and the nanowire peptide can be washed from the solid substrate. The fusion partner peptide can be retained by the solid substrate. For example, the nanowire peptide can be cleaved from a CBD fusion partner peptide by washing the solid substrate with a reducing agent such as β-mercaptoethanol or dithiothreitol.

The nanowire polypeptides resulting from assembly of nanowire peptides are essentially pure, as they are stripped of contaminants, metals, ions, metalloenzymes, flavins, quinones and other redox cofactors. In one embodiment, the purified nanowires are composed of a single peptide subunit (pilin or PilA) which polymerizes via hydrophobic interactions to form the pilus, i.e., nanowire filament. These nanowires can be stored dry substantially indefinitely and can be resuspended in appropriate solvents, as needed, for downstream applications. As noted herein, these novel purified nanowires have conductive (e.g., rectifying) behavior due, in part, to the polarized nature of proteins, containing an N-terminus (positively charged) and a C-terminus (negatively charged) end. Particular rectifying behavior is also due to the protein composition (i.e., amino acid make-up) and structure of the nanowire (i.e., due to the alignment of dipoles of peptide bonds in the pilin's α-helix).

The nanowire polypeptides described herein have asymmetrical conducting properties due to the protein composition (i.e., amino acid make-up) and structure of the nanowire. Such conducting activity is also a characteristic of the disclosed nanowire peptides and polypeptides in pure form, for example, in absence of metals and cellular contaminants that could mask the natural rectifying properties of the nanowire.

By combining more than one asymmetric conductor together, a device can be made with a variety of conductive properties. Moreover, the conductive properties of such a device can be altered by employing genetically or chemically modified nanowire peptides and or by incorporating other materials available to those of skill in the art.

Devices that include microbial nanowires are desirable because the nanowire peptides can be mass-produced and purified from recombinant hosts that are genetically engineered to produce the nanowire subunit. The nanowire peptide subunits can then be assembled in vitro or in vivo to form pili. This will enable the mass-production of nanowire-containing devices at a low cost.

The disclosed peptides may be used in various device applications such as antenna, attenuator, battery, brush, capacitor, condenser, conductor, circuit, electrode, fuel cell, generator, filter circuit breaker (fuse), inductor, coil, nanowire array, particle collector, precipitator, reactor, rectifier, relay, resistor, solar energy collector, spark generator, suppressor, terminal, and the like.

The nanowire polypeptides can also be used, for example, for construction of active devices such as transistors. With regard to nano-electronics, the conductive behavior of nanowires means that protein-based diodes (one-way conductors) can be constructed from these nanowires. In conventional microelectronics, diodes are the basic building blocks for transistors and more complex active components, including the microprocessors that run our computers. Hence, the conducting behavior of the nanowires opens the door to the construction of protein-based nano-electronics transistors and more complex devices.

In one embodiment, nano-electronics include, for example, radio demodulation (rectification of AM radio frequency signals to make audio signals), low voltage AC-DC power conversion, current steering, power switches and over-voltage protection. Other embodiments include, but are not limited to, the logic circuitry in electronic devices such as laptop computers, cellular phones and similar devices, further including computer chips, such as those used in the transportation industry, such as in aircraft and automobiles.

In some embodiments, the nanowire polypeptides can be configured to include branches, for example, by chemically linking two or more nanowire peptides or polypeptides together. Thus, the nanowire polypeptides can be assembled into a main pilus that is elongated and has a selected or desirable length. A plurality of branch pili may emanate from the main nanowire pilus at one or more substantially fixed distances along the length of the main pilus. The main pilus may also include one or more junctions with one or more secondary main pili, where the junctions are substantially perpendicular to the length of the main pilus. In some embodiments, junctions may be developed by growing or expressing nanowire peptides between two regions that may be electrically connected.

In another embodiment, the nanowire peptides can be configured to form part of an apparatus. For example, the apparatus may contain at least one pilus having nanowires peptides. In other embodiments, the apparatus may contain at least one junction between pili. For example, the apparatus may include a plurality of junctions. Each junction may include a branch pilus and an elongate main pilus. For example, each junction may be situated at an interface between a branch pilus and the elongate main pilus.

In one embodiment, the disclosed pili are used in the design and fabrication of biobased devices. Such devices may include biosensors, biocatalytic systems, biofuel cells, and heavy-metal transformation systems and the like. In some embodiments the pilin monomers or pili may be interfaced with a suitable substrate such as gold or carbon. Substrates suitable for fabricating bioelectronic interfaces include substrates that allow nanowires to self-assemble and be conductive.

Nanowire polypeptides can also be expressed in the absence of electron acceptors (e.g., Fe(III) oxides) or when grown under suboptimal growth conditions. Pili production may not be specifically associated with the presence of metal oxides in their culture environment, but rather may be due to the physiological state(s) associated with suboptimal growth, which occurs at lower temperatures, during growth transitions, and when Geobacteraceae have to use insoluble electron acceptors.

In some embodiments, the nanowires are expressed by free-floating cells and used to bind and reductively precipitate toxic contaminants such as uranium along the nanowires. This also shields the cell from the toxic metal and prevents its permeation and precipitation inside the cell envelope. As a result, the cell's catalytic activity is not comprised and the immobilization of the toxic contaminant is sustained for longer periods of time.

Nanowire expression in electron-acceptor limiting conditions or at suboptimal growth temperatures can cause the cells to aggregate or agglutinate forming biofilms. In experiments using Fe(III) oxide-coated surfaces and electrodes it has been demonstrated that *G. sulfurreducens* forms biofilms and generates energy for growth by transferring electrons across the biofilm cell layers. Nanowires are shown to be expressed during the biofilm process. Pilus nanowires can permit electronic communication between the biofilm cells and can maintain the electronic efficiency per cell constant as the biofilm grows. The pili have a structural and electronic role in the biofilms and help maintain adequate cell spacing to provide optimum electronic communication and electron flow across the biofilm. The expression of conductive pili by *Geobacter* also leads to cell aggregation and the biofilm formation.

Biofilm development is often assumed in the subsurface, particularly at the matrix-well screen interface and rock fractures. Field-scale addition of acetate to groundwater also stimulated the growth of *Geobacter* spp. in the sediment particles. Furthermore, their growth shifted from the groundwater to the solid phases during the field-scale acetate addition, where they out-competed other organisms. *Geobacter* cells can transition from planktonic to biofilm physiologies during the metal absorption and reduction following the addition of an electron donor. Biofilms may be at different developmental stages from cell monolayers, immature microcolonies and mature biofilms. In some embodiments, the biofilm is a Geobacteraceae biofilm. In other embodiments the biofilms may be immature, developing or mature biofilms.

The disclosed biofilms may be used to transform heavy metals such as uranium. In some embodiments the biofilms are used to immobilize and reduce heavy metals. In other embodiments, the biofilms express nanowire peptides from any of the disclosed SEQ ID NOS: 1-10, 26-29 or variants or combinations thereof. In other embodiments, the biofilm expressed nanowires of any of the disclosed sequences may be used for heavy-metal transformation. In still other embodiments, the disclosed devices may be adapted for heavy-metal transformation.

Some additional non-limiting embodiments are provided below to further exemplify the present invention.

1. An isolated Geobacteraceae nanowire peptide with at least about 10 to 18 amino acids deleted from its N-terminus.
2. A nanowire peptide having at least 70% amino acid sequence identity to SEQ ID NO:9 with at least about 10 amino acids deleted from its N-terminus.
3. A nanowire peptide having at least 70% amino acid sequence identity to any of SEQ ID NO:1-10, 26-29.
4. The nanowire peptide of any of statements 1-3, which is genetically or chemically modified and does not have a sequence that is identical to an unmodified sequence selected from the group consisting of SEQ ID NO: 26-29.
5. The nanowire peptide of any of statements 1-4, which has at least one amino acid replaced with a hydrophilic or aromatic amino acid.
6. The nanowire peptide of any of statements 1-5, which has at least one amino acid replaced with a charged amino acid residue.
7. The nanowire peptide of any of statements 1-6, which has at least one amino acid replaced with a tyrosine or tryptophan residue.
8. The nanowire peptide of any of statements 1-6, which has at least one amino acid replaced with an aspartic acid, glutamic acid, lysine or arginine residue.
9. The nanowire peptide of any of statements 1-8, fused to fusion partner peptide.
10. The nanowire peptide of any of statements 1-9, fused to fusion partner peptide adapted to be cleavable and/or removable from the nanowire peptide.
11. The nanowire peptide of any of statements 1-10, fused to fusion partner peptide that can be cleaved by a reducing agent.
12. The nanowire peptide of any of statements 1-11, fused to fusion partner peptide comprising chitin-binding domain (CBD).
13. The nanowire peptide of any of statements 1-11, fused to fusion partner peptide consisting essentially of chitin-binding domain (CBD).
14. The nanowire peptide of any of statements 1-11, fused to fusion partner peptide consisting of chitin-binding domain (CBD).
15. The nanowire peptide of any of statements 1-14, wherein the nanowire peptide secondary structure is substantially helical.
16. The nanowire peptide of any of statements 1-15, wherein at least 50% of the nanowire peptide's secondary structure is $\alpha$-helical.
17. The nanowire peptide of any of statements 1-16, wherein at least 60% of the nanowire peptide's secondary structure is $\alpha$-helical.
18. The nanowire peptide of any of statements 1-17, wherein at least 70% of the nanowire peptide's secondary structure is $\alpha$-helical.
19. The nanowire peptide of any of statements 1-18, wherein the nanowire peptide assembles into a pilus.
20. The nanowire peptide of any of statements 1-19, wherein the pilus is electrically conductive.
21. The nanowire peptide of any of statements 1-20, wherein the nanowire peptide contains no metals.
22. The nanowire peptide of any of statements 1-21, wherein the nanowire peptide has a genetic or chemical modification that modulates the conductive, adhesive or coupling property of a pilus assembled from the nanowire peptide.
23. An isolated nucleic acid encoding the nanowire peptide of any of statements 1-22.
24. The isolated nucleic acid of statement 23, comprising a nucleic acid sequence with at least 50% nucleotide sequence identity to SEQ ID NO:11.
25. The isolated nucleic acid of statement 23 or 24, which is incorporated into an expression cassette.
26. The isolated nucleic acid of any of statements 23-25, which is incorporated into a replication or expression vector.
27. The isolated nucleic acid of any of statements 23-26, which is operably linked to an expression control sequence.
28. The isolated nucleic acid of any of statements 23-27, which is operably linked to a polyadenylation or transcriptional termination sequence.
29. An isolated host cell comprising the isolated nucleic acid of any of statements 1-28.
30. The isolated host cell of statement 29, further comprising a pilT gene and/or a pilB gene from a Geobacteraceae bacterium.
31. The isolated host cell of statement 30, wherein the pilT gene and/or the pilB gene is from a *Geobacter* species.
32. The isolated host cell of any of statements 29-31, wherein the cell is a prokaryotic or eukaryotic cell.
33. The isolated host cell of any of statements 29-32, wherein the cell is a prokaryotic cell.

34. The isolated host cell of any of statements 29-33, wherein the cell is a gram negative bacterium.
35. The isolated host cell of any of statements 29-34, wherein the cell is an Geobacteraceae bacterium.
36. The isolated host cell of any of statements 29-35, wherein the prokaryotic cell is *Geobacter sulfurreducens*.
37. The isolated host cell of any of statements 29-36, wherein the prokaryotic cell is *Geobacter sulfurreducens* strain PCA.
38. The isolated host cell of any of statements 29-37, wherein the host cell does not have a pilT gene.
39. The isolated host cell of any of statements 29-34, wherein the host cell is *Escherichia coli*.
40. The nanowire peptide of any of statements 1-22, which is chemically modified to modulate the conductive, adhesive or coupling properties of the nanowire peptide.
41. The nanowire peptide of statement 22 or 40, which is chemically modified using a reagent selected from the group consisting of performic acid, a peroxide, iodoacetamide, iodoacetic acid, bissulfosuccinimidyl suberate, 1-ethyl-3-(3-dimethylaminopropyl) carbodiimide, N-ethylmaleimide, or methyl methanethiosulfonate and S-(2,2,5,5-tetramethyl-2,5-dihydro-1H-pyrrol-3-yl)methyl methanesulfonothioate (MTSL).
42. A pilus comprising the nanowire peptide of any of statements 1-22, 40, 41 or a combination thereof
43. A nanowire pilus comprising a protein filament isolated from a bacterium, the filament comprising the nanowire peptide of any of statements 1-22, 40, 41 or a combination thereof, as peptide subunits capable of assembling into the protein filament and capable of establishing an electrical connection with an electron acceptor.
44. The nanowire pilus of statement 43, wherein the electron acceptor is an insoluble electron acceptor.
45. A rectifier comprising: one or more of the nanowire peptides of any of statements 1-22, 40, 41 or a combination thereof, in a pilus capable of establishing an electrical connection with an electron acceptor.
46. The rectifier of statement 45, wherein the electron acceptor is an insoluble electron acceptor.
47. The rectifier of statement 45 or 46, wherein the nanowire peptides have substantially the same amino acid sequence.
48. The rectifier of statement 45 or 46, wherein at least one of the nanowire peptides has a different amino acid sequence from other nanowire peptides in the pilus.
49. The rectifier of any of statements 45-48 wherein the insoluble electron acceptor is selected from Fe(III) oxide minerals, an electrode, a second isolated pilus or a combination thereof. 50. The rectifier of any of statements 45-49 adapted for use in radio demodulation, low voltage AC-DC power conversion, current steering, power switches, over voltage protection, logic circuitry in electronic devices or computer chips.
51. The rectifier of any of statements 45-50 capable of functioning as an asymmetric conductor for voltages having a range of ±1.2 V.
52. A method of producing a nanowire peptide comprising:
(a) affinity purifying a fusion protein comprising a fusion partner peptide and the nanowire peptide of any of statements 1-22; and
(b) removing the fusion partner peptide from the fusion protein to thereby produce the nanowire peptide; wherein the fusion protein is expressed by a host cell comprising a nucleic acid that encodes the fusion protein.
53. The method of statement 52, wherein the host cell is a microbial host cell.
54. The method of statement 52 or 53, wherein the host cell is a bacterial host cell.
55. The method of any of statements 52-54, wherein the host cell is *Escherichia coli*.
56. The method of any of statements 52-55, wherein removing the fusion partner peptide comprises contacting the fusion protein with a solid substrate comprising a binding agent adapted to bind the fusion partner peptide.
57. The method of statement 56, further comprising washing the nanowire peptide from the solid support after cleaving a bond linking the fusion partner peptide with the nanowire peptide.
58. The method of any of statements 52-57, wherein the fusion partner peptide is adapted to be cleavable and/or removable from the nanowire peptide.
59. The method of any of statements 52-58, wherein the fusion partner peptide can be cleaved from the fusion protein by a reducing agent.
60. The method of statement 59, wherein the reducing agent is β-mercaptoethanol, dithiothreitol (DTT) or a combination thereof
61. The method of any of statements 52-60, wherein the fusion partner peptide can be cleaved from the fusion protein by a change in pH.
62. The method of statement 61, wherein the change in pH comprises a pH of 5-10.
63. The method of statement 62, wherein the change in pH comprises a pH of 7-9.
64. The method of any of statements 52-63, wherein the fusion partner peptide comprises chitin-binding domain or a mutant chitin-binding domain.
65. The method of any of statements 52-64, wherein the fusion partner peptide consists essentially of chitin-binding domain or a mutant chitin-binding domain.
66. The method of any of statements 52-65, wherein the fusion partner peptide consists of chitin-binding domain or a mutant chitin-binding domain.
67. A method to precipitate a soluble metal comprising: contacting one or more conductive pili with the soluble metal.
68. The method of statement 67, wherein a pilin within each of the one or more conductive pili comprises a polypeptide selected from:
nanowire peptide of any of statements 1-22;
a peptide comprising the amino acid sequence of SEQ ID NOS: 1-10, 26-29 or variants or combinations thereof;
a peptide that is encoded by the nucleotide sequence of SEQ ID NO: 11 or variants;
a peptide comprising an amino acid sequence having at least 40% amino acid sequence identity to any of SEQ ID NOS: 1-10;
a peptide of SEQ ID NOS: 1-10 having one to about 30 amino acid truncation at the N-terminus or at the C-terminus or combinations thereof, wherein the polypeptide assembles into the conductive pilus; or a peptide comprising an amino acid sequence having at least 70% amino acid sequence identity to any of SEQ ID NOS: 26-29 or combinations thereof.
69. The method of statement 67, wherein the soluble metal is a heavy metal.
70. The method of statement 67, wherein the one or more conductive pili comprises a polypeptide of SEQ ID NOS: 1-10 having one to about 30 amino acid truncation at the N-terminus or at the C-terminus or combinations thereof, wherein the polypeptide assembles into the conductive pilus.
71. The method of statement 67, 68 or 70, wherein the pilin forms a biofilm.
72. The method of statement 69, wherein the heavy metal is uranium.
73. The method of statement 67, wherein the soluble metal is chromium, cobalt, vanadium or technetium or combination thereof
74. The method of any of statements 67 to 73, wherein the soluble metal is present in a contaminated site, a water source, in waste water, in soil, in a test sample, in manufacturing waste, or in a nuclear reactor cooling fluid.
75. The method of any of statements 67 or 68, wherein one or more conductive pili are present on a host cell that expresses the pilin.
76. The method of statement 75, wherein the host cell is a prokaryotic host cell.
77. The method of claim 75, wherein the host cell is a Geobacteraceae host cell.
78. The method of claim 75, wherein the host cell is a *Geobacter* host cell.
79. The method of claim 75, wherein the host cell is an *E. coli* host cell.
80. The method of any of statements 67 to 79, wherein the conductive pili or pilin subunit are expressed in biofilms.
81. The method of any of statements 67 or 68, wherein the conductive pili or pilin is a device.
82. The method of any of statements 67 or 68, further comprising contacting the conductive pili or pilins with an electron acceptor.
83. The method of any of statements 67 or 68, further comprising contacting the conductive pili or pilins with an electron donor.
84. A biofilm comprising one or more conductive pili.
85. A biofilm comprising one or more conductive pili adapted for soluble metal removal.
86. A biofilm comprising one or more conductive pili, wherein the one or more conductive pili comprises a polypeptide selected from:
nanowire peptide of any of statements 1-22;
a peptide comprising the amino acid sequence of SEQ ID NOS: 1-10, 26-29 or variants;
a peptide that is encoded by the nucleotide sequence of SEQ ID NO: 11 or variants;
a peptide comprising an amino acid sequence having at least 40% amino acid sequence identity to any of SEQ ID NOS: 1-10;
a peptide of SEQ ID NOS: 1-10 having one to about 30 amino acid truncation at the N-terminus or at the C-terminus, wherein the polypeptide assembles into the conductive pilus; or
a peptide comprising an amino acid sequence having at least 70% amino acid sequence identity to any of SEQ ID NOS: 26-29.
87. The biofilm of any of statements 84 to 86, wherein the soluble metal is a heavy metal.
88. The biofilm of statement 87, wherein the heavy metal is uranium.
89. The biofilm of any of statements 84 to 86, wherein the soluble metal is chromium, cobalt, vanadium or technetium.
90. The biofilm of any of statements 84-89, wherein the soluble metal is suspected of being present in a contaminated site, a water source, in waste water, in soil, in a test sample, in manufacturing waste, in a nuclear reactor cooling fluid, in a lake, in a stream or in an ocean.
91. The biofilm of any of statements 84-86, further comprising a host cell that expresses the pilin.
92. The biofilm of statement 91, wherein the host cell is a prokaryotic host cell.
93. The biofilm of statement 91, wherein the host cell is a Geobacteraceae host cell.
94. The biofilm of statement 91, wherein the host cell is a *Geobacter* host cell.
95. The biofilm of statement 91, wherein the host cell is an *E. coli* host cell.
96. The biofilm of any of statements 84 to 95, further comprising an electron acceptor.
97. The biofilm of any of statements 84 to 95, further comprising an electron donor.
98. A kit for remediation of contaminates, comprising any of statements 1-22 or a biofilm of statement 84 to 86 packaged separately from a container containing an electron acceptor and/or a container containing an electron donor.
99. A device or device component comprising:
one or more conductive pili, wherein each pilin within the one or more conductive pili comprises a polypeptide selected from:
nanowire peptide of any of statements 1-22;
a peptide comprising the amino acid sequence of SEQ ID NOS: 1-10, comprising one or more conductive pili or variants or combinations thereof;
a peptide that is encoded by the nucleotide sequence of SEQ ID NO: 11 or variants;
a peptide comprising an amino acid sequence having at least 40% amino acid sequence identity to any of SEQ ID NOS: 1-10 or combinations thereof;
a peptide of SEQ ID NOS: 1-10 having one to 30 amino acid truncation at the N-terminus or at the C-terminus or combinations thereof, wherein the polypeptide assembles into the conductive pilus;
a peptide comprising an amino acid sequence having at least 70% amino acid identity to any of SEQ ID NOS: 26-29 or combinations thereof;
a peptide comprising a cysteine or cysteine-like amino acid added to any of the amino acid sequence of SEQ ID NOS: 1-10, 26-29 or variants or combinations thereof;
100. The device of statement 99, wherein the device is selected from an antenna, attenuator, battery, brush, capacitor, condenser, conductor, circuit, electrode, fuel cell, generator, filter circuit breaker (fuse), inductor, coil, nanowire array, particle collector, precipitator, reactor, rectifier, relay, resistor, solar energy collector, spark generator, suppressor, terminal.
101. The device of statement 99, wherein the device is adapted for soluble metal removal.
102. The device of statement 99, wherein the pili or pilin are interfaced with a substrate.

103. The device of statement 102, wherein the substrate is gold.

104. The device of statement 98, wherein the device's function or utility relates to the pilin's properties, including (1) electrical properties, such as conductivity and rectification, (2) dimensional properties, such as diameter and aspect ratio, and (3) physicochemical properties, such as nontoxicity, rigidity, charge, ability to self-assemble from monomer amino acids, or functional groups that facilitate binding or chemical reactions.

105. The device of statement 99, wherein the pilin peptide may be modified to have pilin properties.

106. The device of statement 105, wherein the pilin's properties, including (1) electrical properties, such as conductivity and rectification, (2) dimensional properties, such as diameter and aspect ratio, and (3) physicochemical properties, such as hydrophobicity, nontoxicity, rigidity, charge, ability to self-assemble from monomer amino acids, or functional groups that facilitate binding or chemical reactions, have been genetically modified DNA encoding the pilin monomers.

107. A method of producing a conductive pili in-vitro, in which the pilin monomers are produced in a host cell, purified from the host cell, and then self-assembled to form the conductive pili or pilin.

108. The method of statement 107, wherein the pilin monomers comprise fusion partner peptides.

109. The method of statement 106, wherein pilin self assemble after removing the fusion partner peptide.

The following non-limiting examples further illustrate some aspects of the invention.

Example 1

Production of Recombinant Nanowire Peptides

Due to the low solubility of the pilin monomeric subunit (PilA), truncated versions of PilA were engineered to enhance solubility. These truncated peptides were termed PilA$_n$, were n is the number of amino acids removed from the hydrophobic N-terminus of the processed PilA peptide, which has a total of 61 amino acids. A nucleic acid encoding the *Geobacter sulfurreducens* pilA peptide with amino acid sequence SEQ ID NO:9 was used as the basis for truncations. For example, a truncated pilin was designed with 10 amino acids removed from the N-terminus (the PilA$_{10}$ peptide with SEQ ID NO:26); removal of 19 amino acids from the N-terminus yielded a PilA$_{19}$ peptide (SEQ ID NO:27); and removal of 20 amino acids from the N-terminus gave rise to the PilA$_{20}$ peptide (SEQ ID NO:28). A PilA$_{22}$ peptide (SEQ ID NO:29) was generated by removal of 22 amino acids from the N-terminal region. A comparison of the truncated pilin sequences is provided below in Table 3.

Truncated pilin nucleic acids were extracted from the genomic DNA of *G. sulfurreducens* by PCR amplification. PCR amplification (30 cycles, 30 s at 95° C., 20 s at 50.7° C., and 1 min at 72° C.) was performed using 100 ng genomic DNA and Platinum™ PCR SuperMix High Fidelity (Invitrogen™, Life Technologies Corp., Carlsbad, Calif.). DNA was isolated from a 2% agarose gel using Zymoclean™ Gel DNA Recovery Kit (Zymo Research, Irvine, Calif.) and ligated in-frame into the expression vector. Table 3 shows the primers used to amplify the DNA and the restriction sites used to clone the pilA$_n$ gene into the expression vectors. Plasmids were then transformed into DH5α *E. coli* cells for propagation. The recombinant plasmids were confirmed by digestion and sequencing.

TABLE 3 pilA$_n$ expression systems

| Expression systems Cloning Vectors | Restriction enzymes | | Primers (SEQ ID NO) |
|---|---|---|---|
| QIAexpressionist pQE-30 UA (Amp$^R$) | | Rev<br>Fwd | 5'-TGGATAGGCGGGCTTTCAAT -3' (NO: 32)<br>5'-ATTCCGCAGTTCTCGGCGTAT -3' (NO: 33) |
| pMAL | | | |
| c4x (Amp$^R$) | Rev Hind III | Rev | 5'-CCCAAGCTTTTAACTTTCGGGCGGATAGGT-3' (NO: 34) |
| p4x (Amp$^R$) | Fwd Xmn I | Fwd pilA$_{20}$ | 5'-ATTCCGCAGTTCTCGGCGTA-3' (NO: 35) |
| IMPACT | Rev Pst I | Rev | 5'-GGTGGTCTGCAGTCATTAACTTTCGGGCGGATAGGT-3' (NO: 36) |
| PTYB11 (Amp$^R$) | Fwd Sap I | Fwd pilA | 5'-GGTGGTTGCTCTTCCAACTTCACCCTTATCGAGCTGCT-3' (NO: 37) |
| | | pilA$_{10}$ | 5'-GGTGGTTGCTCTTCCAACGCGATCATCGGTATTCTCGC-3' (NO: 38) |
| | | pilA$_{19}$ | 5'-GGTGGTTGCTCTTCCAACGCGATTCCGCAGTTCTCGGC-3' (NO: 39) |
| | | PilA$_{20}$ | 5'-GGTGGTTGCTCTTCCAACATTCCGCAGTTCTCGGCGTA-3' (NO: 40) |
| | | PilA$_{22}$ | 5'-GGTGGTTGCTCTTCCAACCAGTTCTCGGCGTATCGTGT-3' (NO: 41) |

| Name | SEQ ID NO: | Sequence |
|---|---|---|
| PilA | 9 | FTLIELLIVVAIIGILAAIAIPQFSAYRVKAYNSAASSDLRNLKTALESAFADDQTYPPE |
| PilA$_{10}$ | 26 | ----------AIIGILAAIAIPQFSAYRVKAYNSAASSDLRNLKTALESAFADDQTYPPES |
| PilA$_{19}$ | 27 | -------------------AIPQFSAYRVKAYNSAASSDLRNLKTALESAFADDQTYPPES |

TABLE 3-continued pilA$_n$ expression systems

| PilA$_{20}$ | 28 | --------------------IPQFSAYRVKAYNSAASSDLRNLKTALESAFADDQTYPPES |
|---|---|---|
| PilA$_{22}$ | 29 | ---------------------QFSAYRVKAYNSAASSDLRNLKTALESAFADDQTYPEES |

Expression of Recombinant Pilins

Recombinant plasmids were transformed into competent *Escherichia coli* cells (see Table 4) for expression.

TABLE 4

Bacterial strains used to express recombinant pilin subunits.

| Expression system | *E. coli* strain | Characteristics |
|---|---|---|
| QIAexpressionist ™ | M15[pREP4] | Kan$^R$ |
| p-MAL ™ | K12 TB1 | F$^-$ ara Δ(lac-proAB) [Φ80dlac Δ(lacZ)M15] rpsL(Str$^R$) thi hsdR |
| IMPACT ™ | Rosetta 2 (DE3)pLysS$^a$ | F$^-$ ompT hsdS$_B$(r$_B^-$ m$_B^-$) gal dcm (DE3) pLysSRARE2 (Cam$^R$) |

$^a$Novagen, EMD Chemicals, Gibbstown, NJ

To test expression and optimize growth conditions of the recombinant proteins, small-scale experiments (~50 mL cultures) were carried out using LB media. Glucose was added to LB media when using vectors from the p-MAL expression system to repress the maltose genes on the chromosome of the *E. coli* cells. Antibiotics were added where appropriate to the following final concentrations: ampicillin (Amp), 100 μg/mL; chloramphenicol (Cam), 34 μg/mL; kanamycin (Kan), 50 μg/mL. In general cells were grown at 37° C. and 200 rpm and induced with isopropyl-1-thio-D-galactopyranoside (IPTG) when OD$_{600}$ was within 0.4 to 0.6. Temperature after induction was lowered to 30° C. Cells were harvested 6 hours after induction by centrifugation at 5000×g for 20 minutes at 4° C. Pellet was stored at −70° C.

After confirming expression of the pilin peptides, and optimizing conditions, large-scale expression was carried out in a batch reactor. In these experiments, an overnight culture of transformed *E. coli* cells was used to inoculate a batch bioreactor (Bioflow 3000, New Brunswick Scientific, Edison, N.J.) containing 5 L yeast enriched HM media plus ampicillin and chloramphenicol. The HM medium contains 9 g/L potassium phosphate monobasic KH$_2$PO$_4$, 6 g/L potassium phosphate dibasic K$_2$HPO$_4$, 6 g/L sodium phosphate dibasic Na$_2$HPO$_4$, 3 g/L ammonium phosphate dibasic (NH$_4$)$_2$HPO$_4$, 5 g/L yeast, 1 g/L magnesium sulfate MgSO$_4$, 10 g/L glucose, 5 mL/L of trace elements (Menzella et al., *Biotechnology and Bioengineering* 82, 809-817 (2003)). Trace elements solution contains 10 g/L iron (II) sulfate FeSO$_4$, 2.5 g/L zinc sulfate heptahydrate ZnSO$_4$.7H$_2$O, 1 g/L manganese sulfate pentahydrate MnSO$_4$.5H$_2$O, 1 g/L cobalt (II) chloride hexahydrate CoCl$_2$.6H$_2$O, 1 g/L sodium molybdate dihydrate Na$_2$MoO$_4$.2H$_2$O, 0.2 g/L sodium borate decahydrate Na$_2$B$_4$O$_7$.10H$_2$O, 5 g/L calcium chloride dihydrate CaCl$_2$.2H$_2$O, dissolved in 5 M hydrochloric acid HCl. Temperature, pH, glucose feeding, and dissolved oxygen were controlled with a PID (proportional-integral-derivative) controller (Li et al., *Biotechnology and Bioengineering* 64, 61-73 (1999)). Cells were grown overnight (~16 to 20 h) at 37° C., with periodic addition of 50% (w/v) glucose and 20 g/L MgSO$_4$ to replenish depleted glucose. The pH was set to 7.0 and controlled by addition of concentrated ammonium hydroxide NH$_4$OH. Dissolved oxygen (DO) was kept at 10% during the fermentation process by increasing agitation speed from 50 to 1000 rpm, increasing the airflow rate, and through glucose feeding. After overnight growth, expression of the recombinant protein was induced with 0.5 mM IPTG. Temperature was lowered to 30° C. after induction. Six hours after induction, cells were harvested by centrifugation at 5000×g for 20 minutes at 4° C. The pellet was stored at −70° C. Expression of the fusion protein was confirmed by SDS-PAGE and western blot analysis.

Purification of Recombinant Pilins

Purification of recombinant pilins was done by affinity chromatography. The type of resin used varied with the expression system used. For the QIAexpressionist™ system, nickel-nitrilotriacetic acid (Ni-NTA) resin was employed. For the pMAL™ expression system an amylose resin was used. Chitin beads were used for the IMPACT™ system.

For cytoplasmic expression, the harvested cells were resuspended on lysis buffer (10 mL of buffer per gram of cells) and broken using a tip sonicator (Sonifier 250, Branson, Danbury, Conn.). Composition of buffers used during purification can be found in Table 10.

TABLE 5

Affinity resin and composition of buffers and solutions used during affinity chromatography purification of recombinant pilin subunits.

| | QIAexpressionist ™ | p-MAL ™ | IMPACT ™ |
|---|---|---|---|
| Resin | Ni-NTA | Amylose | Chitin |
| Lysis Buffer | 50 mM Na-phosphate pH 7.8, 0.3 mM NaCl, 10 mM βME, 2% CHAPS, 20 mM imidazole, 1 mg/mL lysozyme | 20 mM Tris-HCl pH 7.4, 200 mM NaCl, 1 mM EDTA, 1 mM PMSF | 20 mM Tris-HCl pH 7.4, 100 mM NaCl, 1 mm EDTA, 1 mM PMSF, 2% CHAPS |
| Osmotic Shock | | 30 mM Tris-HCl pH 8.0, 20% sucrose, 1 mM EDTA (incubate 5-10 min, centrifuge at 8000 × g for 20 minutes at 4° C.) Resuspend pellet in 5 mM MgSO$_4$ ice cold (stir for 10 min, centrifuge at 8000 × g for 20 minutes at 4° C.). Supernatant is osmotic shock fluid. | |
| Wash Buffer | 50 mM Na-phosphate pH 7.8, 0.3 mM NaCl, 10 mM βME, 0.2% CHAPS, 20 mM imidazole | 20 mM Tris-HCl pH 7.4, 200 mM NaCl, 1 mM EDTA | 20 mM Tris-HCl pH 7.4, 600 mm and 1M NaCl, 1 mM EDTA |
| Cleavage Buffer | | | 20 mM Tris-HCl pH 9.0, 100 mM NaCl, 1 mM EDTA |
| Elution Buffer | 50 mM Na-phosphate, | 20 mM Tris-HCl pH 7.4, 200 mM | 20 mM Tris-HCl pH 7.4, |

TABLE 5-continued

Affinity resin and composition of buffers and solutions used during affinity chromatography purification of recombinant pilin subunits.

| QIAexpressionist™ | p-MAL™ | IMPACT™ |
|---|---|---|
| pH 7.8, 0.3 mM NaCl, 10 mM βME, 0.2% CHAPS, 300 mM imidazole | NaCl, 1 mM EDTA, 10 mM maltose | 100 mm NaCl, 1 mM EDTA |

Crude extracts were sonicated 7 times on ice, for 10 seconds each time. A clarified cell extract was obtained by centrifugation at 20,000×g for 30 minutes at 4° C. The supernatant was collected and loaded into an affinity column to allow binding of the target protein.

Vector p4x from the pMAL™ system produced periplasmic expression of a MPB-PilA$_n$ fusion protein. To purify the fusion protein, harvested cell pellets were subjected to osmotic shock to release periplasmic proteins. The osmotic shock fluid was loaded into the amylose resin affinity column. After binding, the column was washed to remove all non-specific proteins bound to the column. The subsequent steps varied depending on the purification system used.

For the QIAexpressionist™ system, His-tagged pilin was eluted from the nickel-nitrilotriacetic acid column with buffer containing 300 mM imidazole. For the pMAL™ system, elution of the maltose binding protein (MBP)-PilA$_n$ fusion was with a buffer containing 10 mM maltose. After elution the MBP tag was cleaved from the pilin using Factor Xa protease. Fusion proteins expressed from the IMPACT™ system were cleaved by incubation of the column with buffer containing dithiothreitol (DTT) to release the PilA$_n$ subunit from the chitin-bound intein tag (CBD). Cleavage efficiency was tested at 4° C. or 23° C. for 24 to 72 hours. After cleavage, the pilin subunits were eluted from the column using storage buffer. Production of a pilin subunit was confirmed by SDS-PAGE, and MALDI-TOF mass spectrometry.

Sodium Dodecyl Sulfate-Polyacrylamide Gel Electrophoresis (SDS-PAGE)

Protein expression and cleavage efficiency was evaluated by SDS-PAGE using Tris-glycine polyacrylamide gel (Bio-Rad, Hercules, Calif.), where 12% Tris/glycine polyacrylamide gels were used to assess protein expression and 7.5% Tris/glycine polyacrylamide gels were used to assess cleavage efficiency. For solid samples, a pellet from 100 to 1000 μL of cell culture was dissolved in loading buffer (100 mM Tris pH 6.8, 20% glycerol, 8 M urea, 2% (w/v) sodium dodecyl (SDS), 0.02% bromophenol blue). Liquid samples were dissolved 1:1 using loading buffer. Production of pilin was confirmed using Mini-Protean® Tris-Tricine Precast Gels (Bio-Rad Laboratories, Hercules, Calif.). Samples for Tris/tricine gels were prepared by dilution with same volume of Tricine Sample Buffer ((Bio-Rad Laboratories, Hercules, Calif.). Gels were run in a Mini Trans-Blot® Electrophoretic Transfer Cell System (Bio-Rad Laboratories, Hercules, Calif.). Running buffers used were 25 mM Tris, 192 mM glycine, 0.1% SDS for Tris/glycine gels, and 100 mM Tris, 100 mM Tricine, 0.1% SDS for Tris/tricine gels. Running conditions were as followed: Tris-glycine gels 30 minutes at 200 V, Tris-tricine gels 120 min at 100 V. Gels were stained with Bio-Safe Coomassie Stain (Bio-Rad Laboratories, Hercules, Calif.) for one hour and de-stained in water until bands were clearly visible. Tricine gels required an additional 30 minutes fixing step with a solution of 50% methanol, 10% acetic acid in water prior to being stained.

Western Blot Analysis

Proteins were transferred from acrylamide gel to a polyvinylidene fluoride (PVDF) membrane (Millipore, Billerica, Mass.) using a Trans-Blot® SD Semi-Dry Transfer Cell (Bio-Rad Laboratories, Hercules, Calif.). After transfer, PVDF membrane was blocked with 5% (w/v) non-fat dry milk in TBST buffer (20 mM Tris pH 7.6, 137 mM Nail, 0.1% Tween® 20) for at least 1 hour at 4° C. The membrane was incubated for 1 hour at 23° C. with the primary antibody. After three washes of five minutes each with Tris-Buffered Saline 0.1% Tween® 20 (TBST) buffer, the membrane was incubated with the secondary antibody for 1 hour at 23° C. Washing step with TBST was repeated. Proteins were visualized by chromogenic detection using 3,3',5,5'-tetramethylbenzidine (TMB) (Thermo Scientific Pierce, Rockford, Ill.). Antibodies were dissolved in blocking solution. Primary antibodies anti-MBP, and anti-CBD were used at 1:5000 dilutions (New England Biolabs, Ipswich, Mass.). Secondary antibody, goat anti-mouse IgG-HRP linked was used at 1:5000 dilutions (Sigma-Aldrich, St. Louis, Mo.).

Matrix Assisted Laser Desorption-Ionization-Time of Flight Mass Spectrometry (MALDI-TOF MS)

1 μL of sample was mixed with 1 μL of 50 mM 3,5-dimethoxy-4-hydroxycinnamic acid in 50% acetonitrile $CH_3CN$/0.5% trifluoroacetic acid TFA and dried onto sample plate. Mass spectra were collected on a time-of-flight (TOF) Voyager-DE Pro-MALDI-TOF (Applied Biosystems, Framingham, Mass.).

Circular Dichrosim (CD)

Circular dichrosim (CD) spectra were measured on a Chirascan™ spectrometer (Applied Photophysics Ltd., Leatherhead, United Kingdom). Spectra were recorded from 190 to 260 nm with a 0.5 nm increment and a 5 seconds integration time using a 0.1 cm path length quartz cuvette (Starna Cells Inc., Atascadero, Calif.) with peptide concentrations ranging from 65 μg/mL to 41 μg/mL. Measurements were performed in 10 mM potassium acetate pH 3.8, 50 mM $NaSO_4$ and 10 mM potassium phosphate pH 7.0, 50 mM $NaSO_4$. The effect of detergents, sodium dodecyl sulfate (SDS) and octyl β-D-glucopyranoside (OG), on the secondary structure of the pilin monomers was investigated. Spectra were baseline corrected and smoothed using a third order Savitsky-Golay filter. Spectral data are presented in units of molar ellipticity per residue, [θ]. To convert CD instrument units (θ, millidegrees) into mean residue molar ellipticity [θ] units, the following equation was applied (Wallace & Janes, *Advances in Biomedical Spectroscopy*. Edited by H., P. I. Amsterdam: IOS Press (2009)):

$$[\theta] = \left(\frac{\theta \times 0.1 \times MWR}{c \times l}\right) \tag{9.1}$$

where c is the peptide concentration in mg/mL, l is the path length of the cuvette in cm, and MWR is the mean residue weight of the sample, equals to:

$$MWR = \frac{MW}{n-1} \tag{9.2}$$

where MW is the peptide molecular mass in Daltons, and n is the number of amino acid residues (42 for the PilA$_{19}$ monomer).

The peptide concentration was determined as the difference spectrum of identical concentration of protein dissolved in 6 M guanidine hydrochloride at pH 12.5 versus pH 7.1 (Greenfield, *Nat. Protocols* 1, 2876-2890 (2007). Concentration was determined from the absorbance at 294 using the known amino acid composition of the PilA$_{19}$ subunit and the reported values of the molar extinction coefficients for tyrosine and tryptophan residues (Mihalyi, *Journal of Chemical & Engineering Data* 13, 179-182 (1968)). The following equation was applied:

$$c = \frac{A_{293}}{2,357Y + 830W} \quad (9.3)$$

where Y is the number of tyrosines and W is the number of tryptophans, three and zero respectively for the PilA$_{19}$ subunit.

In-Vitro Assembly of Recombinant Pilins into Pilus Fibers

After purification, recombinant pilin subunits were exchanged from buffer solution to a mixture of acetonitrile and water with 0.1% trifluoroacetic acid using either a C18 reverse phase Sep-Pak preparation column (Waters Corporation, Milford, Mass.) or a C18 separation via high performance liquid chromatography (HPLC). Samples were dried with a SpeedVac concentrator. The dry sample was re-suspended in filtered DI water or 10 mM CHES buffer pH 10.0. The re-suspended sample was imaged by TEM and AFM to confirm the assembly of PilA$_{19}$ subunits into pili fibers.

Transmission Electron Microscopy (TEM)

A 10 µL aliquot of sample was deposited on a Formvar nickel-coated grid, and stained with a solution containing 2% uranyl acetate in water. Images were acquired using a JEOL 1000 CX transmission electron microscope (JEOL, Peabody, Mass.) operated at an accelerated voltage of 100 kV Atomic Force Microscopy (AFM)

Pili fibers assembled with recombinant pilins in vitro were deposited on freshly cleaved mica and imaged with a Nanoscope IV Multimode scanning probe microscope (Veeco, Santa Barbara, Calif.) equipped with a J scanner. Images were collected in tapping mode using commercially available silicon or silicon nitrite cantilevers.

Scanning Tunneling Microscopy (STM)

The conductive properties of the recombinant pili were assessed using a table-top Nanosurf EasyScan STM (see, Veazey, Scanning probe studies of the pilus nanowires in *Geobacter sulfurreducens*, Michigan State University (2011)). Briefly, the sample is firmly attached to a conductive cylinder that rest on a rail system. The tip is held by a conductive clamp that also serves as a tunneling current lead. The sample holder is moved towards the fixed tip via a linear piezo motor. Sample is kept at ground, and the voltage is applied just to the tip. Vibration isolation is implemented by a rubber damping stack that suppresses high frequencies and a single spring suspension stage that suppresses frequencies lower than 50 Hz. The STM is placed inside a plastic glove bag through which a constant flow of dry nitrogen is supplied.

After confirming the assembly of recombinant pili via TEM, a 10 µL drop of the sample was deposited on a freshly cleaved layer of highly oriented pyrolytic graphite (HOPG). The sample was left on the HOPG for at least 30 minutes to allow diffusion and absorption onto the surface. The substrate was then rinsed with deionized (DI) water; excess moisture was removed using filter paper. STM topography measurements of the recombinant pili were done at room temperature (about 23° C.).

Production of Recombinant Pilins

The high hydrophobicity of the nanowire pilin greatly limits its mass-production in a heterologous host. The pilin's hydrophobicity is illustrated in the hydropathicity plot shown in FIG. 1, which was generated by the method of Kyte & Doolittle, *Journal of Molecular Biology* 157, 105-132 (1982). This method calculates the average hydropathicity of a moving segment as it advances through the sequence from the amino to the carboxy terminus, by progressively evaluating 19-residue pilin segments. It uses a hydropathicity scale that assigns a value to each amino acid reflecting its hydrophobicity or hydrophilicity.

The Kyte & Doolittle method shows a hydrophobicity consistent with the trans-membrane nature of the pilin peptide. When the hydropathicity of a given 19-residue segment averages more than 1.6, there is a high probability that this sequence is part of a membrane-bound protein spanning the membrane. The hydropathicity graph shows that up to position 18 of the PilA sequence, the average hydrophobicity score is greater that 1.6 (dashed line in hydropathicity plot of FIG. 1). FIG. 1 also shows the grand average of hydropathicity index (GRAVY) for the PilA truncations investigated. The GRAVY index is the average hydropathicity score for all the amino acids in a protein, where a positive GRAVY index indicates a protein is hydrophobic, while a negative GRAVY index indicates a protein is hydrophilic (Kyte & Doolittle, *Journal of Molecular Biology* 157, 105-132 (1982)). A PilA truncation of 10 amino acids yields a protein having a GRAVY index that is lower that the full length PilA, but is still positive, indicating that some hydrophobicity is still present. Other truncations, PilA$_{19}$, PilA$_{20}$, and PilA$_{22}$, have negative indexes indicating a change from a hydrophobic to a hydrophilic nature.

A 20 amino acids truncation of the PilA subunit (named PilA$_{20}$, SEQ ID NO:36) was selected, and its expression and purification was investigated using the QIAexpressionist (Qiagen, Valencia, Calif.) expression system. A hexa poly-histidine-tag (6×His-Tag) was attached to the N-terminal PilA$_{20}$ subunit that generally does not interfere with the folding and function of its fusion partner. Purification of the 6×His-Tagged-PilA$_{20}$ protein is performed using a Ni-NTA metal-affinity chromatography (Malhotra & Murray, Chapter 16 Tagging for Protein Expression. *Methods in Enzymology*, Vol. Volume 463, pp. 239-258. Academic Press (2009)).

Poor and leaky expression was observed for the 6×His-PilA$_{20}$ fusion protein. The theoretical molecular weight of the 6×His-PilA$_{20}$ is 6,590 kDa yet most of the histidine-tagged protein had a higher molecular weight as detected by SDS-PAGE and western blot. These results indicate that most of the target protein remains in the insoluble fraction of the cell lysate and that the pilins may be forming aggregates.

To improve the solubility of the PilA$_{20}$ peptide, the Intein-mediated purification with an affinity chitin binding tag system (IMPACT™, New England Biolabs Incorporated, Ipswich, Mass.) was used. A chitin-binding domain (CBD) was attached to the N-terminal of the PilA$_{20}$ sequence, which could be removed by a self-splicing mechanism in the presence of reducing agents (Fong & Wood, *Trends in Biotechnology* 28, 272-279 (2010)). This system therefore eliminates the need for protease cleavage.

The expression of various truncations of the pilA gene was investigated using the IMPACT™ expression system to identify a shorter PilA peptide that could readily be expressed and purified as a soluble product. A nucleic acid encoding the chitin-binding domain (CBD) was therefore attached to the N-termini of selected pila$_n$ sequences. Constructs were prepared for the full length pilin (PilA) and for the truncated PilA$_{10}$, PilA$_{19}$, PilA$_{20}$, and PilA$_{22}$ peptides. These constructs were then transformed into Rosetta 2(DE3) pLysS *E. coli* cells, a strain that enhances expression of proteins with codons rarely used in *E. coli*.

As evidenced by SDS-PAGE, expression of the fusion protein was achieved for all truncated constructs (CBD-PilA$_{10}$, CBD-PilA$_{19}$, CBD-PilA$_{20}$, CBD-PilA$_{22}$) but not for the full-length CBD-PilA fusion protein. Growth in the cultures was monitored by measuring their optical density spectrophotometrically (OD values). Cultures containing cells expressing the CBD-PilA fusion did not grow at the same rate as cells expressing truncated pilin fusions, indicating that CBD-PilA may inhibit the growth of *E. coli* cells.

Affinity chromatography was employed to simultaneously cleave and purify the truncated pilins using a chitin bead column and incubation with dithiothreitol (DTT). The pilin peptides were released and eluted from the column while the CBD tag remained bound to the chitin beads. Cleavage efficiency was monitored as a function of incubation time and temperature. Higher temperatures generally improved the cleavage of all fusion proteins. Cleavage of PilA$_{19}$ from CBD was faster when compared to PilA$_{10}$, PilA$_{20}$, and PilA$_{22}$. For example, almost complete cleavage of PilA$_{19}$ was observed at 23° C. after 24 h of incubation, whereas PilA$_{10}$ exhibited only about 50% cleavage at after 24 h at this temperature. Moreover, the PilA$_{10}$ cleavage did not improve significantly with increased incubation time. Approximately 80% of the PilA$_{22}$ fusion was cleaved at 23° C. after 48 h of reaction.

After cleavage and elution from the column with buffer, analysis by SDS-PAGE demonstrated that the PilA$_{19}$ and PilA$_{22}$ monomers were readily expressed and that cleavage was efficient at 23° C. and 4° C. Although some PilA$_{20}$ was generated and cleaved, soluble PilA$_{20}$ was effectively invisible on the SDS-PAGE gels; confirming the low cleavage efficiency of this construct. But PilA$_{20}$ in elution fraction was detected by MALDI-TOF mass spectrometry, a more sensitive technique. Similarly, while significant cleavage of PilA$_{10}$ was observed, this peptide was only slightly visible in SDS-PAGE gels when cleavage was done at 4° C. and no PilA$_{10}$ was seen in SDS-PAGE gels when cleavage was done at 23° C. Furthermore, when the cleavage was performed on-column, the matrix clogged suggesting the PilA$_{10}$ subunit was prone to aggregation. All four of the truncated pilins had a molecular weight consistent with their theoretical molecular weight as confirmed by MALDI-TOF MS.

The chitin-binding domain not only increased the solubility of the pilin but also eliminated the need for proteases during cleavage. Four truncated constructs were expressed using this system. However, while the shortest truncation was expressed as a soluble fusion protein (CBD-PilA$_{10}$), when the PilA$_{10}$ peptide was released from the fusion, it showed signs of aggregation, complicating further purification of larger quantities of this peptide. In contrast, the second shortest PilA$_{19}$ peptide did not exhibit aggregation and was readily purified. The PilA$_{19}$ peptide was selected for use in additional experiments.

Secondary Structure of Pilin Subunits

Figure 2A:
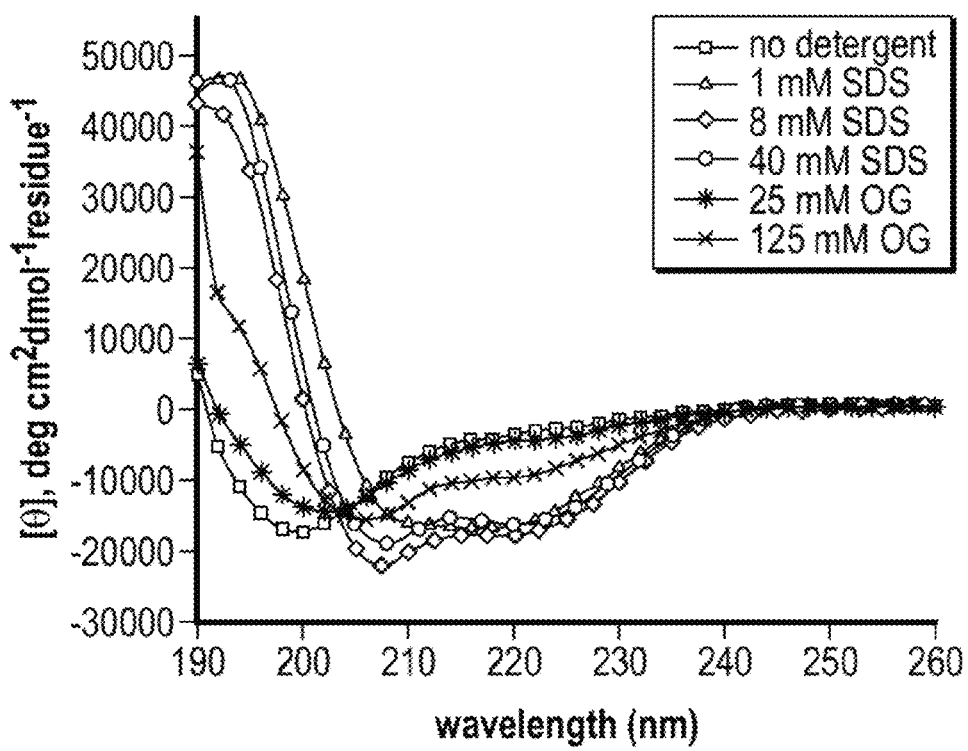
FIGS. 2A and 2B are graphs illustrating the surfactant-dependent folding of the recombinant $PilA_{19}$ peptide (SEQ ID NO:35) at pH 3.8 (FIG. 2A) and at pH 7.0 (FIG. 2B) as detected by circular dichrosim (CD). The $PilA_{19}$ peptides were dissolved in 10 mM potassium acetate pH 3.8, 50 mM $Na_2SO_4$ with and without surfactants to obtain the CD spectrum shown in FIG. 2A. To obtain the CD spectrum in FIG. 2B, the $PilA_{19}$ peptides were dissolved in 10 mM potassium phosphate pH 7.0, 50 mM $Na_2SO_4$ with and without surfactants. The surfactants used were sodium dodecyl sulfate (SDS) and octyl β-D-glucopyrano side (OG).
Figure 2B:
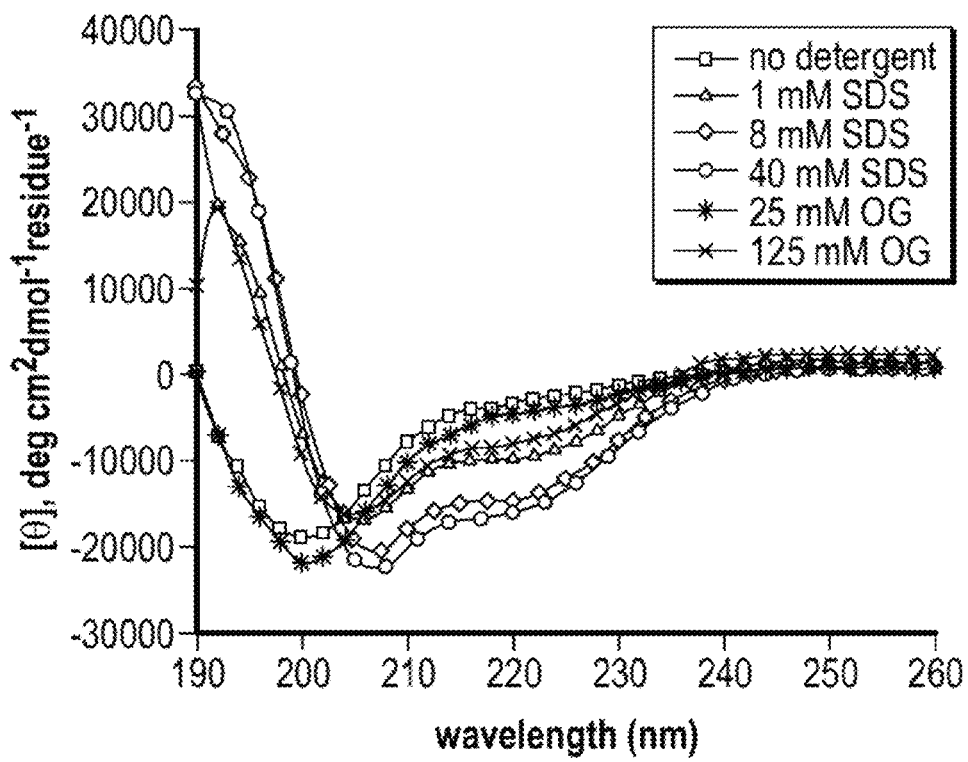

Circular dichrosim spectra of the PilA$_{19}$ peptide were obtained at pH 3.8 and 7.0 with or without the addition of detergents sodium dodecyl sulfate (SDS) and octyl β-D-glucopyranoside (OG). As a reference, the critical micelle concentrations (CMC) of these surfactants are ~8 mM for SDS and ~25 mM for OG. FIGS. 2A and 2B show the CD spectra of PilA$_{19}$ subunits at pH 3.8 and 7.0 respectively. When no detergent is present the PilA$_{19}$ subunit is disordered at both pH 3.8 and pH 7.0, and exhibits very little ellipticity above 210 nm. However, SDS addition at any of the concentrations investigated induced a conformational change in the pilin subunit. A characteristic circular dichrosim signature indicative of an α-helix was observed after SDS addition under both pH conditions.

When OG was added at a concentration close to its critical micelle concentration (25 mM), no significant change in the shape of the PilA$_{19}$ CD spectra was observed at either pH, indicating the PilA$_{19}$ peptide was in a disordered conformation despite the addition of OG. However, the PilA$_{19}$ monomer did exhibit the characteristic α-helical signature when concentrations of OG approximately five times higher than the CMC were employed.

Figure 3A:
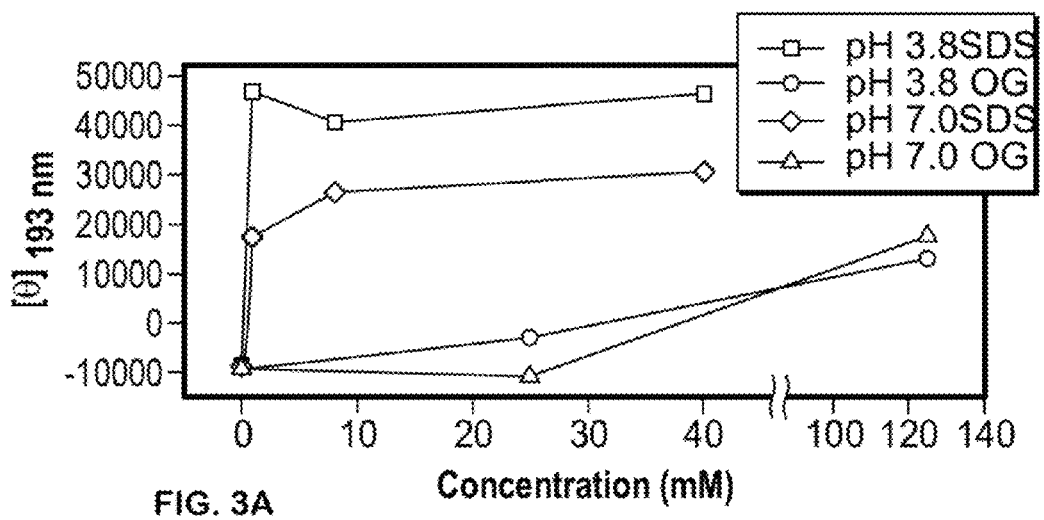
FIGS. 3A-3C are graphs illustrating the effect of surfactants on the conformation of $PilA_{19}$ subunits. Molar ellipticities at pH 3.8 and 7.0 are plotted for three wavelengths: 193 nm (FIG. 3A), 208 nm (FIG. 3B), and 222 nm (FIG. 3C), as a function of surfactant concentration. Lines connecting data points are for visual aid only.
Figure 3B:
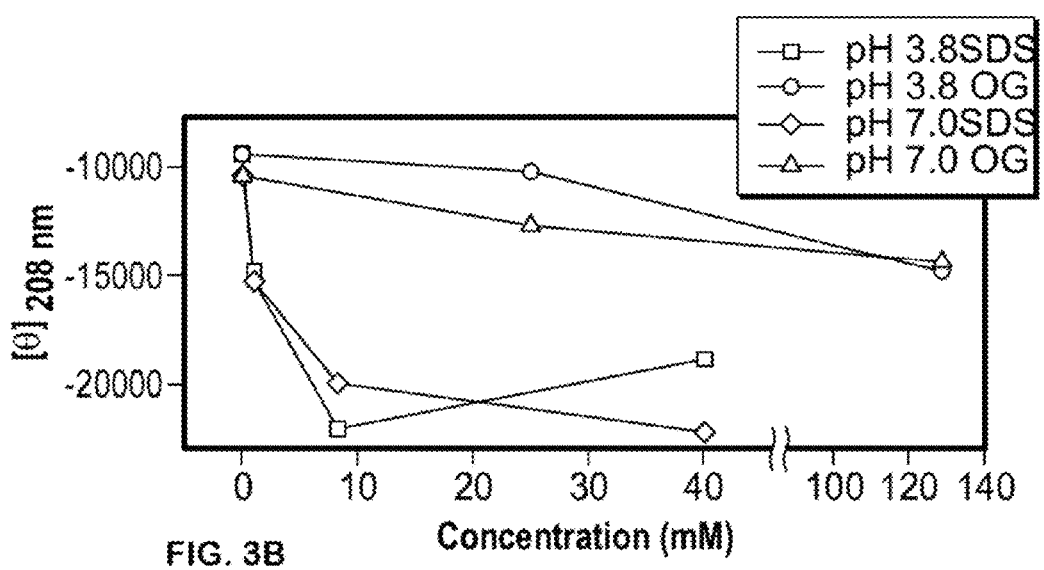
Figure 3C:
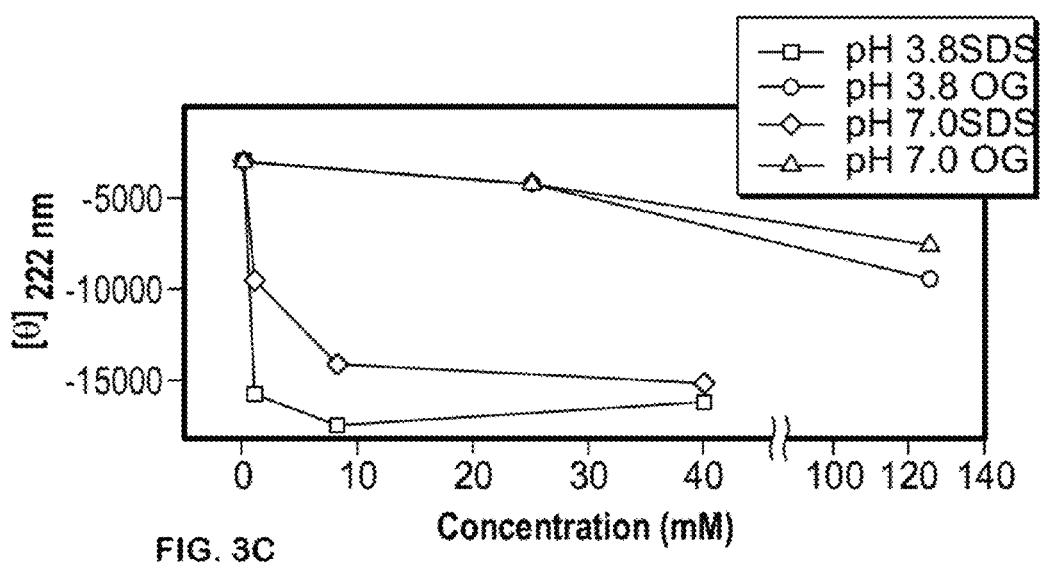

FIG. 3 shows the ellipticity values at wavelengths 193 nm, 208 nm and 222 nm as a function of surfactant concentration. The addition of detergents (either SDS or OG) increased the ellipticity at 193 nm for the PilA$_{19}$ protein under both pH conditions investigated. However, the change was more dramatic when SDS was added. For example, while the mean residue ellipticity values at 208 nm and 222 nm became more negative when either detergent was added, the effect is larger for SDS than for OG. At pH 7.0 there was a trend for the ellipticity values to become more negative as the concentration of SDS was increased. These data indicate that there is an increase in the α-helical content of the PilA$_{19}$ peptide when the SDS concentration increased. The behavior at pH 3.8 was different. In particular, the ellipticity values at 208 nm and 222 nm become more negative at pH 3.8 when 8 mM SDS was present, indicating that the helicity of the PilA$_{19}$ peptide at pH 3.8 increased as follows: 0 SDS<1 mM SDS<40 mM SDS<8 mM SDS.

To further analyze the percent α-helicity from the collected CD data, the CONTINLL software package was used, which is publicly available through the DICROWEB server. See, Whitmore, & Wallace, *Nucleic Acids Research* 32, W668-W673 (2004); Whitmore, & Wallace, *Biopolymers* 89, 392-400 (2008); Provencher & Gloeckner, *Biochemistry* 20, 33-37 (1981); van Stokkum et al. *Analytical Biochemistry* 191, 110-118 (1990). The secondary structure components determined with CONTINLL are α-helix (regular α$_R$ and distorted α$_D$), β-strands (regular β$_R$ and distorted β$_D$), turns, and unordered (Sreerama & Woody, *Analytical Biochemistry* 287, 252-260 (2000)). The program evaluates the goodness of fit parameter NMRSD (normalized mean residue standard deviation), which is defined as:

$$NRMSD = \left[ \frac{\Sigma(\theta_{exp} - \theta_{cal})^2}{\Sigma(\theta_{exp})^2} \right]^{1/2} \quad (9.4)$$

where $\theta_{exp}$ and $\theta_{cal}$ are the experimental and calculated ellipticity values at a specific wavelength. A Normalized Mean Residue Standard Deviation (NRMSD) value of less than 0.1 is considered a good fit (Wallace & Janes, Advances in Biomedical Spectroscopy. Edited by H., P. I. Amsterdam: IOS Press (2009)).

Table 6 shows the calculated percentage of the various secondary structure components for all the conditions considered, where the NRMSD parameter is a measure of the goodness of the fit, and values below 0.1 are considered a good fit. The various secondary structures calculated were: α-helix (regular αR and distorted αD), β-strands (regular βR and distorted βD), turns, and unordered. The focus of the analysis was on the percent of regular α-helicity (αR).

Figure 4:
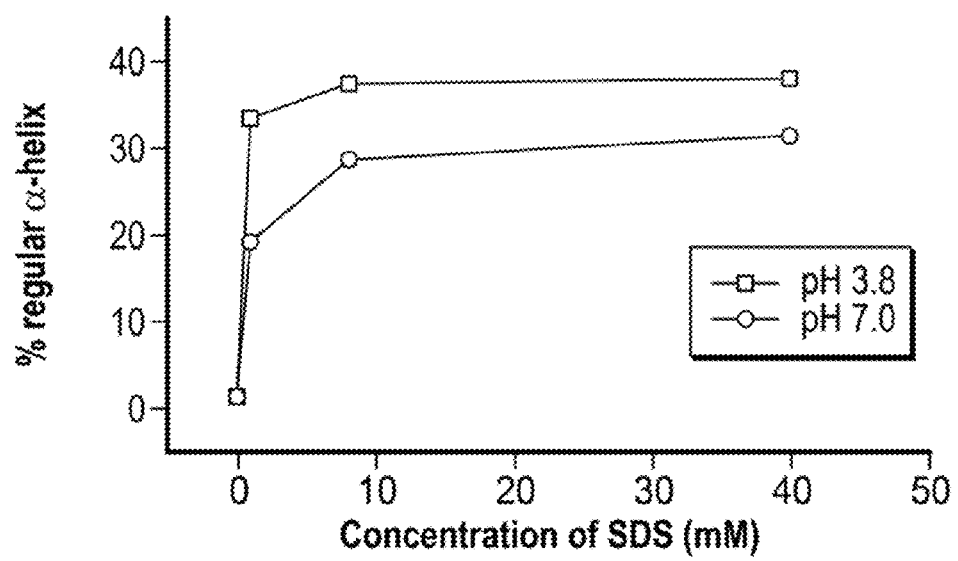
FIG. 4 is a graph illustrating the effect of SDS on the percentage of regular α-helix of $PilA_{19}$ peptides at pH 3.8 (solid squares) and pH 7.0 (open squares). Percentage of regular α-helix was calculated using the CONTINLL algorithm. Lines connecting data points are for visual aid only.

These secondary structure calculations generally indicated that the percentage of α-helix increased with increasing concentrations of SDS, and the effect was observed at both pH 3.8 and 7.0 (see also FIG. 4). Table 6 also indicates that the percent of α-helix is higher at pH 3.8 than at pH 7.0, and that the data fit of the pH 7.0 results is worse than the data fit for the pH 3.8 results. Even though the NRMSD value is higher than 0.1 for some pH 7.0 calculations where SDS was present, an inspection of the fitted data with respect to the experimental data shows that the discrepancies are not that marked. Despite some residual variance, the results support the conclusion that SDS promotes the formation of an α-helical structure in the $PilA_{19}$ peptide.

a 1 mM undecanethiol (Sigma-Aldrich, St. Louis, Mo.) solution in ethanol. Following monolayer formation, gold substrates were washed with ethanol and dried under nitrogen. Formation of undecanethiol monolayer was verified using ellipsometry and cyclic voltammetry.

Monolayer formation was followed by overnight incubation at room temperature with $PilA_{19}$ subunits dissolved in 20 mM sodium phosphate buffer pH 7.0, 100 mM NaCl, with or without 10 mM SDS. To assess the assembly of recombinant pilins into pili, the samples were analyzed using scanning transmission microscopy (SEM).

Expression and Purification of Recombinant $PilA_{19}$-A20C Subunits

The IMPACT expression system (New England Biolabs Incorporated, Ipswich, Mass.) described in Example 1 was

TABLE 6

Analysis of CD data using the CONTINLL algorithm.
% secondary structure

| Type of secondary structure | no detergent | | 1 mM SDS | | 8 mM SDS | | 40 mM SDS | | 25 mM OG | | 125 mM OG | |
|---|---|---|---|---|---|---|---|---|---|---|---|---|
| | pH 3.8 | pH 7.0 | pH 3.8 | pH 7.0 | pH 3.8 | pH 7.0 | pH 3.8 | pH 7.0 | pH 3.8 | pH 7.0 | pH 3.8 | pH 7.0 |
| $α_R$ | 1.2 | 1.7 | 33.7 | 19.2 | 37.2 | 28.6 | 38 | 31.3 | 5.4 | 3.5 | 15.6 | 26.9 |
| $α_D$ | 3.0 | 4.9 | 14.9 | 7.6 | 18.4 | 14.5 | 18.3 | 17.0 | 5.7 | 5.2 | 6 | 14.9 |
| $β_R$ | 13.9 | 9.1 | 18.5 | 13.6 | 1.6 | 5.7 | 5.8 | 0.9 | 11.9 | 7.4 | 19.7 | 21.8 |
| $β_D$ | 6.6 | 5.1 | 10.2 | 4.1 | 2.7 | 2.9 | 4.1 | 2.6 | 6.2 | 4.1 | 6.8 | 12 |
| Turns | 12.0 | 11.9 | 22.7 | 9.6 | 13.6 | 12.7 | 14.8 | 14.3 | 12.7 | 10.4 | 13.5 | 24.5 |
| Un-ordered | 63.2 | 67.2 | 0 | 45.9 | 26.6 | 35.6 | 18.9 | 33.8 | 58.2 | 69.3 | 38.4 | 0 |
| Total | 99.9 | 99.9 | 100 | 100 | 100.1 | 100 | 99.9 | 99.9 | 100.1 | 99.9 | 100 | 100.1 |
| NRMSD | 0.045 | 0.068 | 0.036 | 0.113 | 0.058 | 0.119 | 0.028 | 0.117 | 0.073 | 0.073 | 0.177 | 0.206 |

Note
that the value of the NMRSD parameter is higher than 0.1 for some sets of the data, indicating that the data may not optimally fit the indicated type of secondary structure. Since the highest values for the NRMSD parameter are for the cases with 125 mM OG at pH 3.8 and pH 7.0, these data were not considered during the analysis.

In-vitro Assembly of Recombinant Pilins into Pili Fibers

Figure 5:
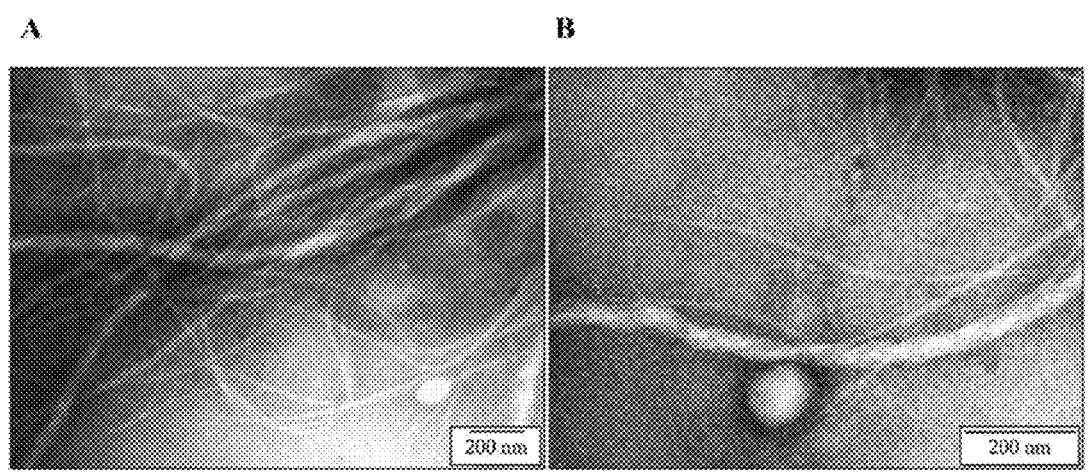
FIGS. 5A-5B are transmission electron microscopy (TEM) images of recombinant pili fibers assembled from $PilA_{19}$ peptide subunits. Samples were stained with uranyl acetate. The transmission electron microscope was a JEOL 2200FS (JEOL Inc., Boston, Mass.) operated at an accelerating voltage of 100 kV.
Figures 6A, 6B, 6C:
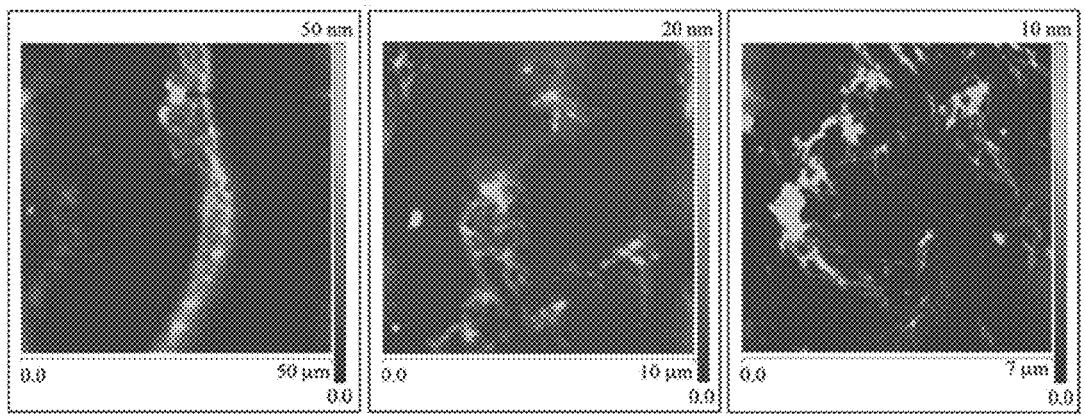
FIGS. 6A-6C are atomic force microscopy images of recombinant pili fibers assembled from $PilA_{19}$ peptide subunits after deposition on mica.

The $PilA_{19}$ peptide was assembled into nanowires after elution from a C18 reverse phase column in a mixture of acetonitrile and pure water, followed by removal of the organic solvent using SpeedVac concentrator. TEM and AFM images showed the formation of hair-like structures (FIGS. 5 and 6). It was observed that pili fibers aggregated forming large clusters. The filaments are less than 10 nm in diameter and are several microns in length.

Conductivity Assessment of Recombinant $PilA_{19}$ Fibers via STM

Figures 7A, 7B:
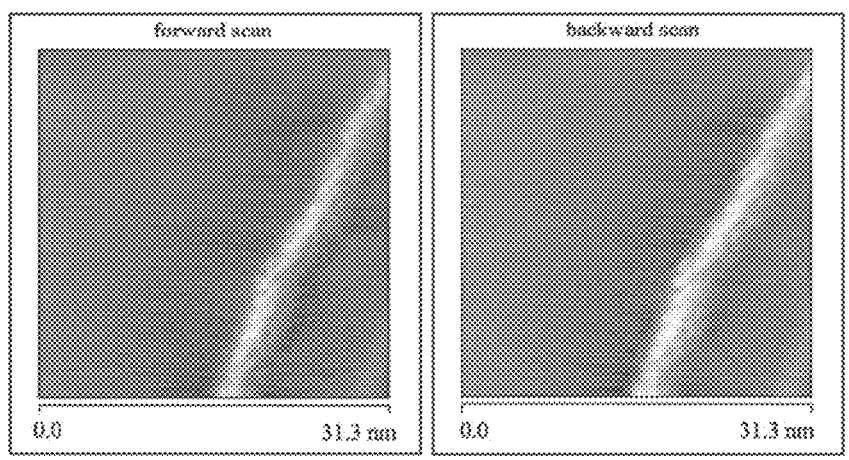
FIGS. 7A and 7B are Scanning Tunneling Microscopy (TSM) images of a recombinant pilus fiber assembled from $PilA_{19}$ peptide subunits. Applied voltage 0.05 V.

PilA nanowires were shown to be conductive. The STM image shown in FIG. 7 supports the conclusion that the recombinant $PilA_{19}$ polypeptide is also conductive. This STM image was collected at 0.05 V and shows a conductive filament similar in size and structure to that of the native pilus nanowires.

Example 2

Pilin Modifications for Electrode Interfacing

Interfacing of Recombinant $PilA_{19}$ Monomer with Gold Electrodes

Gold substrates (LGA Thin Films, Santa Clara, Calif.) were washed with ethanol, dried under nitrogen, and cleaned by a 30 s immersion in piranha solution (7 parts by volume concentrated sulfuric acid to 3 parts by volume 30% aqueous hydrogen peroxide). After piranha cleaning, substrates were washed copiously with DI water and dried under nitrogen. Substrates were incubated for 48 h at room temperature with used to produce the cysteine-modified pilin. The pilin was expressed as a fusion of a chitin binding domain tag (CBD-$PilA_{19}$-A20C). Plasmid was transformed into DH5α E. coli cells for propagation. Sequence of the expression plasmid was confirmed before transforming into competent E. coli strain Rosetta2 DE3 p(LysS). The expression was carried out in a 10 L batch reactor (Bioflo 3000, New Brunswick Scientific, Edison, N.J.).

5 L of yeast-enriched HM (Hagem) media containing trace elements, 100 μg/mL ampicillin, and 34 μg/mL chloramphenicol, was inoculated. Cells were grown overnight at 37° C. with periodic addition of 50% (w/v) glucose and 20 g/L MgSO4. The pH was set to 7.0 and the dissolved oxygen (DO) was kept at 10%. Expression of the recombinant protein was induced with 0.5 mM IPTG and the temperature was lowered to 30° C. Six hours after induction, the cells were harvested by centrifugation at 5000×g for 20 min at 4° C. The cell pellet was stored at −70° C. Expression of the fusion protein was tested by SDS-PAGE, western blot.

Purification of the $PilA_{19}$-A20C monomers was performed by affinity chromatography using chitin beads. All the buffers used during purification are shown in Table 5. Harvested cells were re-suspended in a lysis buffer (10 mL of buffer per gram of cells) and lysed using a tip sonicator (Sonifier 250, Branson, Danbury, Conn.). The crude extract was sonicated on ice 7 times for 10 s, and the cell extract was clarified by centrifugation at 20,000×g for 30 minutes at 4° C. The supernatant was loaded into the chitin affinity column to allow binding of the target protein. Non-specifically bound proteins were removed from the column by washing with buffer with increasing concentrations of sodium chloride. The cleavage of the CBD from the $PilA_{19}$-A20C pilin was achieved by rinsing the column with 3 column volumes of incubation buffer containing 50 mM DTT. The column was then incubated for 40 hours at room temperature. The $PilA_{19}$-A20C monomers were eluted from the column with a storage buffer. The production of pilin subunits was confirmed by SDS-PAGE, and MALDI-TOF mass spectrometry. The SDS-PAGE, western blot, and MALDI-TOF analysis, were performed as described in Example 1.

Interfacing Recombinant $PilA_{19}$-A20C Pilins with Gold Electrodes

Clean gold substrates were incubated overnight with a solution containing $PilA_{19}$-A20C subunits. After incubation, samples were analyzed using ellipsometry, cyclic voltammetry (CV), and scanning electron microscopy (SEM). The deposition of $PilA_{19}$-A20C monomers on the gold electrode was monitored in real time using quartz crystal microbalance (QCM).

Ellipsometry

Film thicknesses were determined using a M-44 rotating analyzer ellipsometer (J. A. Woollam Co., Inc., Lincoln, Nebr.) controlled by WVASE32 software. The incident angle was set at 75° using 44 wavelengths of light between 414.0 and 736.1 nm. The refractive index (n) and extinction coefficient (k) were assumed to be n=1.5 and k=0, respectively, for determination of all thicknesses. Thickness measurements were performed on at least 3 spots on each substrate and then averaged.

Scanning Electron Microscopy (SEM)

To prepare samples for SEM, the gold substrates were gently washed and dried by either critical point drying or freeze-drying. In critical point drying, the water in the sample is first replaced by a dehydration fluid. The samples were dehydrated by incubation in a graded ethanol series (25%, 50%, 75%, 95%) for 20 min at each concentration, followed by three 10 min changes in 100% ethanol. Samples were dried in a Balzers Model 010 critical point dryer (Balzers Union Ltd., Balzers, Liechtenstein) using liquid carbon dioxide as transitional fluid. In freeze-drying, samples were frozen in liquid nitrogen, and water was then sublimated during an 18 h cycle in an EMS 750 freeze dryer (Electron Microscopy Sciences, Hatfield, Pa.). After drying, samples were mounted on SEM stubs and coated with a thin layer (~2 nm) of osmium using a NEOC-AT pure osmium coater (Meiwa Shoji CO. Ltd., Osaka, Japan).

Scanning electron microscopy was performed using the secondary electron imaging (SEI) detector of a JSM 7500F with cold field emission electron emitter SEM (JEOL Ltd., Tokyo, Japan). An accelerating voltage of 5 kV or less was used for imaging. Energy dispersive X-ray (EDS) microanalysis coupled to the SEM was used for elemental analysis. EDS was done using an Oxford Instruments INCA system (Oxford Instruments, High Wycomb, Bucks, England), software version 14.3, using a 30 mm2 detector crystal and an ultrathin window. During EDS, an accelerating voltage of 1 kV was used to avoid excitation of gold characteristic X-ray lines.

Cyclic Voltammetry (CV)

In cyclic voltammetry, the potential of the working electrode is cycled between two values at a specific scan rate, and the current produced by the electron transfer process is measured. The cyclic voltammogram of a clean electrode in the presence of a redox couple will display a characteristic duck shape with well-defined reduction and oxidation peaks. The formation of a SAM on the electrode can be studied using CV. A defect free monolayer acts as an insulating barrier that hinders electron transfer at the electrode surface, so no reduction or oxidation peaks would be observed. The presence of pinholes or defects in the monolayer would allow access of redox species to the electrode surface.

A conventional three-electrode cell consisting of the gold-modified working electrode, a platinum auxiliary electrode, and a silver/silver chloride (Ag/AgCl) reference electrode was used for electrochemical measurements. Cyclic voltammetry (CV) was performed using a CHI660 potentiostat (CH Instruments, Austin, Tex.). Measurements were carried out in 100 mM phosphate buffer pH 7.0 containing 100 mM NaCl and 5 mM potassium ferricyanide ($K_3[Fe(CN)_6]$).

Quartz Crystal Microbalance (QCM)

Quartz crystal microbalance (QCM) is a sensitive technique used to study real time formation of films on surfaces. It takes advantage of the piezoelectric properties of quartz crystals and the relationship between the frequency of oscillation and the mass of deposited material. A research system quartz crystal microbalance RQCM (Inficon, East Syracuse, N.Y.) controlled by a RQCM logging data system was used to monitor crystal frequency (f) changes due to the deposition of $PilA_{19}$-A20C monomers on the gold substrate. Changes in viscoelastic properties of the adsorbed mass are reflected in changes of the dissipated energy (D), which was calculated from the measured resistance (R), using the following equation:110; 111

$$D = \frac{32 f_f^2 Z_q d_q^2 RA}{\pi} \quad (4.1)$$

where ff is the fundamental frequency of the quartz crystal (5×106 Hz), Zq is the acoustic impedance for AT-cut quartz (8.8×106 kg m2 s-1), dq is the piezoelectric strain coefficient for AT-cut quartz (3.1×10-12 m V-1), and A is the electrode area (34.19 mm2). The RQCM was equipped with a 0.1 mL flow cell and an AT-cut polished sensing crystal, 5 MHz, Ti/Au (Inficon, East Syracuse, N.Y.). A PHD standard infusion syringe pump (Harvard Apparatus, Holliston, Mass.) was used to fill the flow cell with buffer (10 mM potassium phosphate buffer pH 7.0 with 50 mM $Na_2SO_4$). After equilibration of the crystal, the $PilA_{19}$-A20C monomers were introduced into the flow cell at a flow rate of 0.2 mL/min and changes on frequency and resistance were monitored.

Interfacing Recombinant $PilA_{19}$ Monomers with Gold Electrodes

Figure 9:
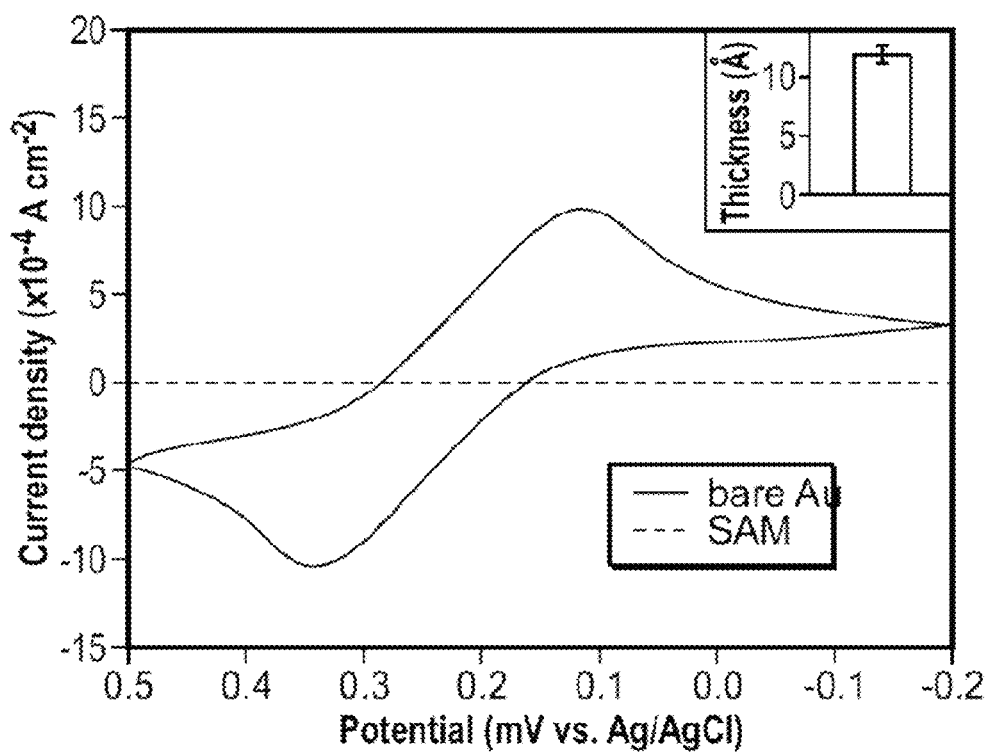
FIG. 9 is a graph showing formation of an undecanethiol self-assembled monolayer on a gold electrode. The cyclic voltammogram of bare gold (solid black line), and undecanethiol SAM (dashed line). Data recorded at room temperature in 100 mM sodium phosphate at pH 7.0 containing 100 mM NaCl, and 5 mM $K_3[Fe(CN)_6]$ at a potential scan rate of 100 mV s$^{-1}$. The inset shows the thickness of the undecanethiol monolayer measured by ellipsometry.

SAM deposited on a gold electrode could trigger assembly of recombinant $PilA_{19}$ subunits into pili. The formation of the undecanethiol monolayer on gold was confirmed by cyclic voltammetry and ellipsometry. FIG. 9 shows the CV curves for bare gold and undecanethiol SAM. The bare gold voltammogram shows the characteristic duck shape with well-defined oxidation and reduction peaks. The SAM curve shows a significant decrease in current with no distinctive peaks, indicating that the monolayer acts as a dielectric barrier that blocks electron transfer between the electroactive species in solution and the electrode. Ellipsometry results showed a monolayer thickness of 11.90±0.720 Å (see inset of FIG. 9), consistent with values reported in literature.

Formation of the undecanethiol SAM on the gold substrate was followed by incubation with $PilA_{19}$ monomers in buffer solution with and without SDS. After incubation with pilin subunits, the substrates were gently washed and the remaining solution was removed by freeze-drying. Samples were analyzed by scanning electron microscopy (SEM) to determine if interaction with the hydrophobic monolayer would trigger assembly of pilin subunits into pili.

Figure 10:
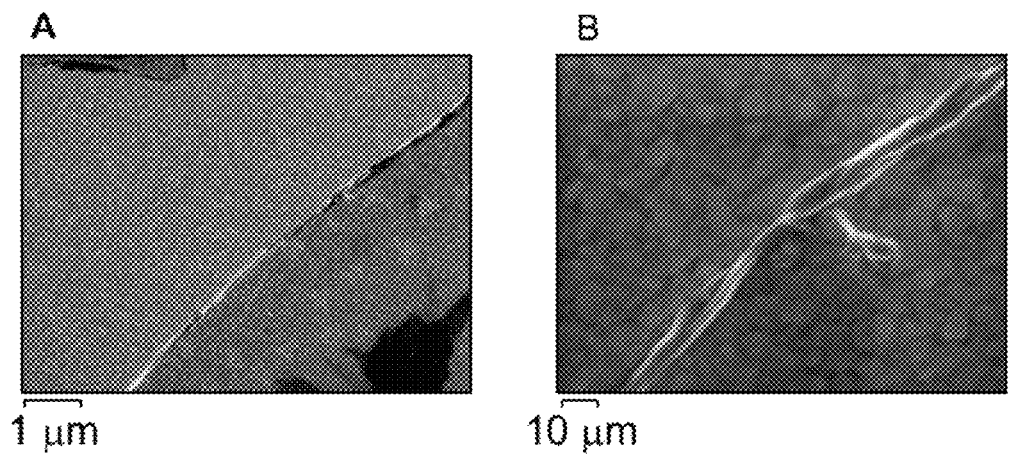
FIGS. 10A and 10B are black and white Scanning Electron Microscopy (SEM) images of gold substrates after deposition of an undecanethiol self-assembled monolayer (SAM) followed by incubation with PilA$_{19}$ monomers in 20 mM sodium phosphate pH 7.0, 100 mM NaCl, 10 mM SDS. Accelerating voltage 5 kV.
Figure 11:
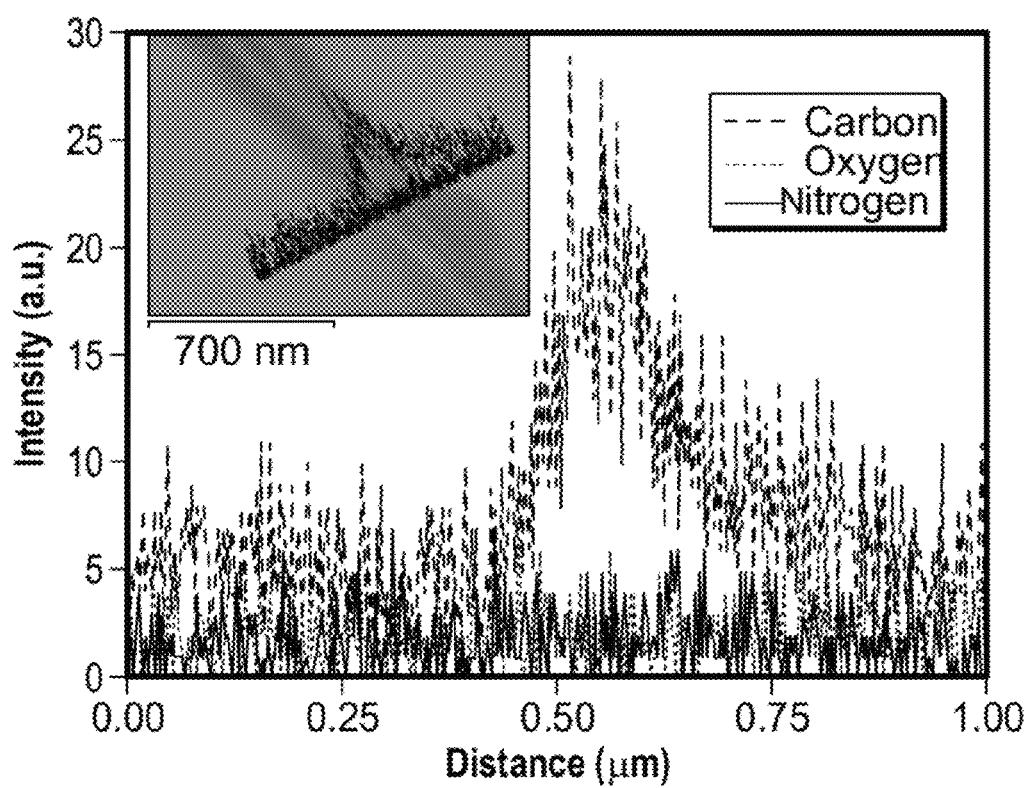
FIG. 11 shows Energy Dispersive X-ray (EDS) microanalysis of fibers present on gold substrates modified by deposition of an undecanethiol SAM, followed by incubation with PilA$_{19}$ monomers in 20 mM sodium phosphate pH 7.0, 100 mM NaCl, 10 mM SDS. Accelerating voltage 1 kV.

SEM analysis of samples incubated with PilA$_{19}$ monomers in buffer without SDS did not show formation of any defined structures. Samples incubated with PilA$_{19}$ subunits in buffer containing 10 mM SDS showed areas where formation of horizontal fiber-like structures on the surface was observed (FIG. 10B). Energy dispersive X-rays spectroscopy (EDS) was used to determine the elements present in these fibers. An accelerating voltage of 1 kV was used to avoid excitation of gold X-rays characteristic lines, which would make it extremely difficult to identify other elements present in the sample. EDS analysis shown in FIG. 11 indicated the carbon content was higher on the fiber than on the gold substrate.

Production of Cysteine Modified Recombinant Pilin: PilA$_{19}$-A20C

Figure 8:
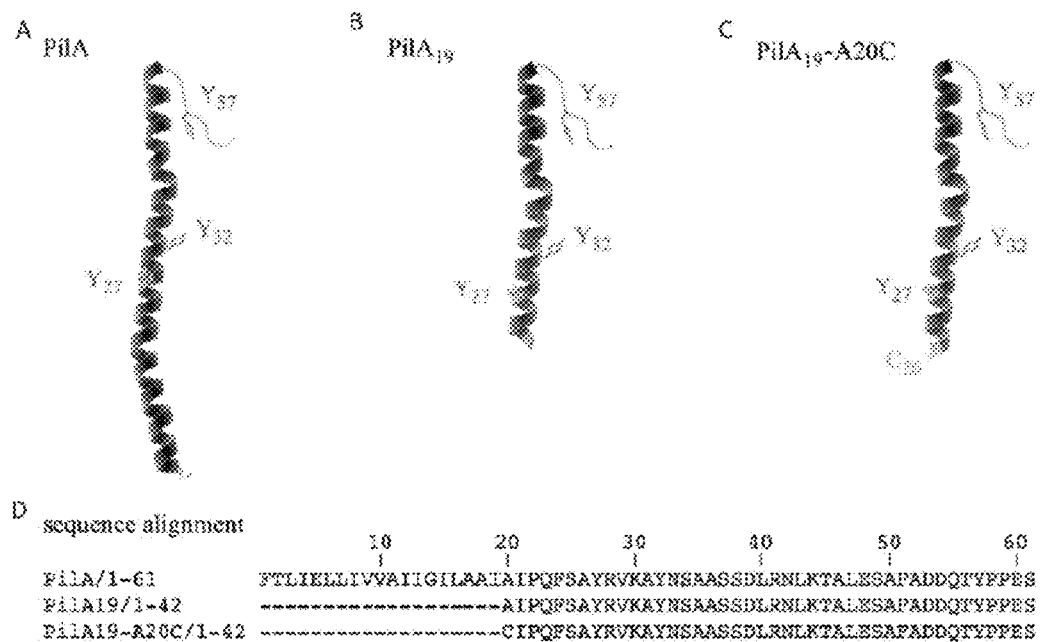
FIGS. 8A-8D show structural comparisons of wild-type and recombinant pilins of *Geobacter sulfurreducens*, and the associated sequence alignment, with FIG. 8A showing the structure wild-type PilA protein.

To facilitate the interfacing of pilin monomers with gold substrates, a cysteine-modified subunit was engineered. The PilA$_{19}$-A20C monomer is a 19 amino acid truncation of the full length pilin of Geobacter sulfurreducens, where the last amino acid at the N-terminal end, alanine, was substituted with a cysteine (FIG. 8C). PilA$_{19}$-A20C subunit was expressed as a fusion protein with a chitin-binding domain (CBD-PilA$_{19}$-A20C). The purification of the recombinant pilin was performed by affinity chromatography using chitin beads.

Figure 12:
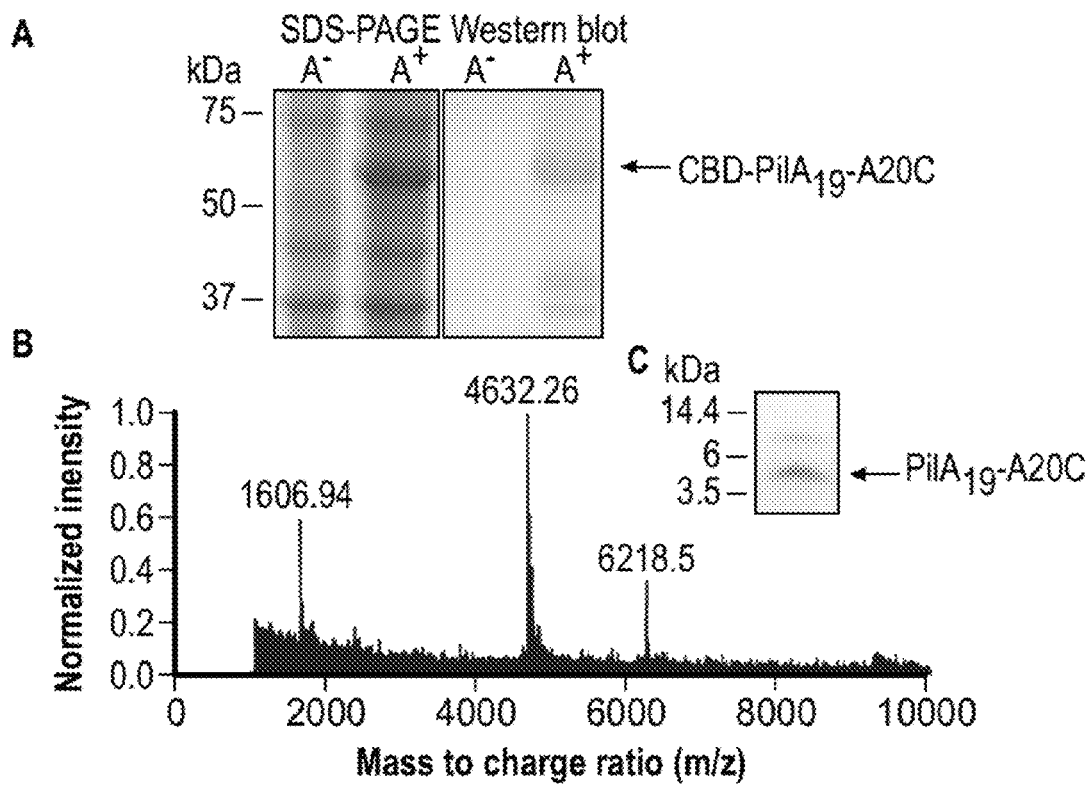
FIGS. 12A-12C show expression and purification of recombinant PilA$_{19}$-A20C subunits: a) 12% sodium dodecyl sulfate polyacrylamide gel electrophoresis (SDS-PAGE) and western blot analysis of cells before (A$^-$) and after (A$^+$) induction (FIG. 12A). Anti-chitin serum was used for western blot. b) MALDI-TOF mass spectrometry (FIG. 12B) and c) 10-20% tricine gel of elution fraction after purification (FIG. 12C).

FIG. 12A shows SDS-PAGE results and FIG. 12B shows MALDI-TOF results, each of which demonstrate the successful production of recombinant cysteine-modified subunit (PilA$_{19}$-A20C). SDS-PAGE results confirmed the expression of the CBD-PilA$_{19}$-A20C fusion, based on the appearance of a strong band at ~65 kDa after induction. Western blot analysis was positive when using an anti-chitin antibody. FIG. 12C corresponds to a tricine gel showing the two bands in the elution fraction after purification. The elution fraction was analyzed by MALDI-TOF mass spectrometry (FIG. 12B). The peak at 4,632.26 kDa confirms the production of PilA$_{19}$-A20C subunits. The theoretical molecular weight of the PilA$_{19}$-A20C monomer is 4,627.08 kDa. The peak at 6,218.5 kDa is likely a non-specifically bound protein in the column that was not removed during the washing step. The peak at 1,606.94 kDa does not show on the tricine gel because of the low molecular weight and corresponds to an additional peptide that is cleaved from the fusion.

Interfacing Recombinant PilA$_{19}$-A20C Pilins with Gold Electrodes

Figure 13:
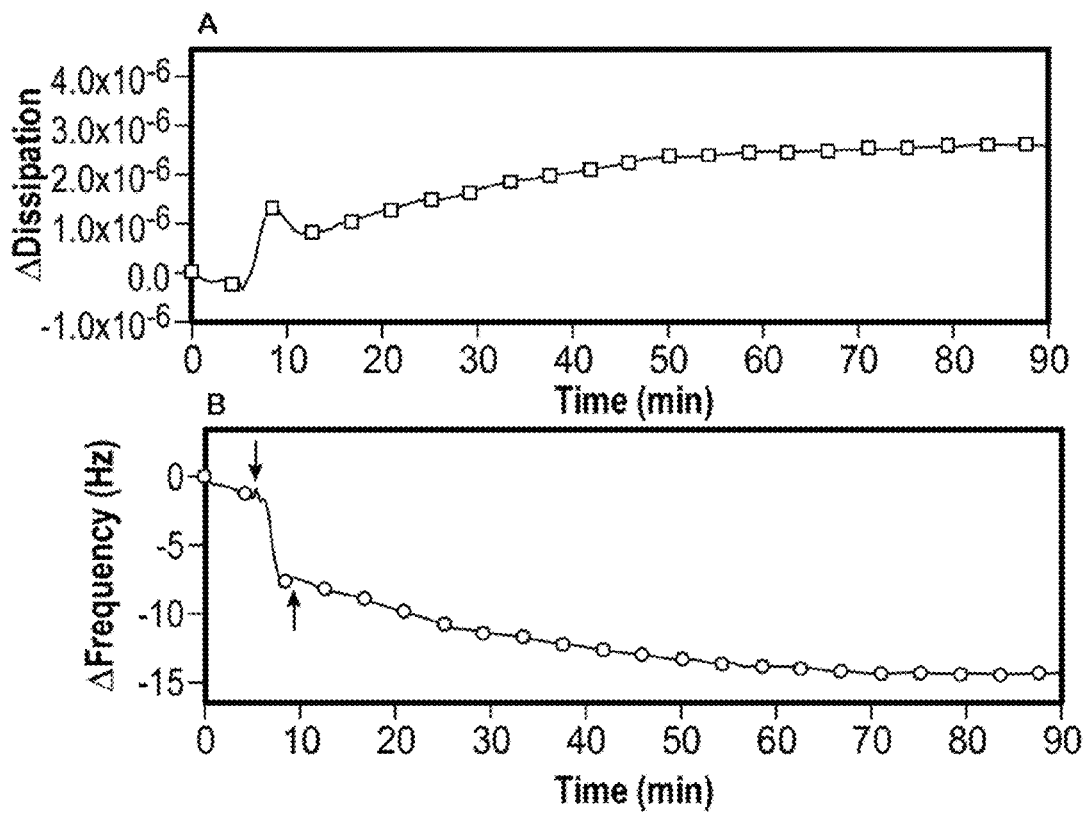
FIGS. 13A and 13B are graphs showing deposition of PilA$_{19}$-A20C monomers on a gold electrode. Quartz crystal microbalance was used to monitor changes in frequency and dissipated energy after the addition of pilin monomers.

The interaction between the cysteine-modified subunits and the gold substrates were tested. The results showed the formation of a monolayer of PilA$_{19}$-A20C subunits on the gold surface. FIGS. 13A and 13B show QCM results obtained during the deposition of cysteine-modified pilins on a gold electrode. The arrow pointing down indicates the time when the protein solution was introduced into the flow cell. The arrow pointing up indicates the time when the syringe pump was stopped. The frequency shift after the introduction of the pilin subunits is associated with a change in mass indicating the absorption of pilin monomers on the gold electrode. The dissipation change is related to the presence of more protein on the QCM crystal that is coupling more strongly to the fluid. A bare QCM crystal will not couple strongly to the fluid surrounding it, but the protein will. As more protein is deposited on the crystal, the sum of the protein-fluid interactions increases and the dissipative contribution to the QCM signal increases as a result.

Figure 14:
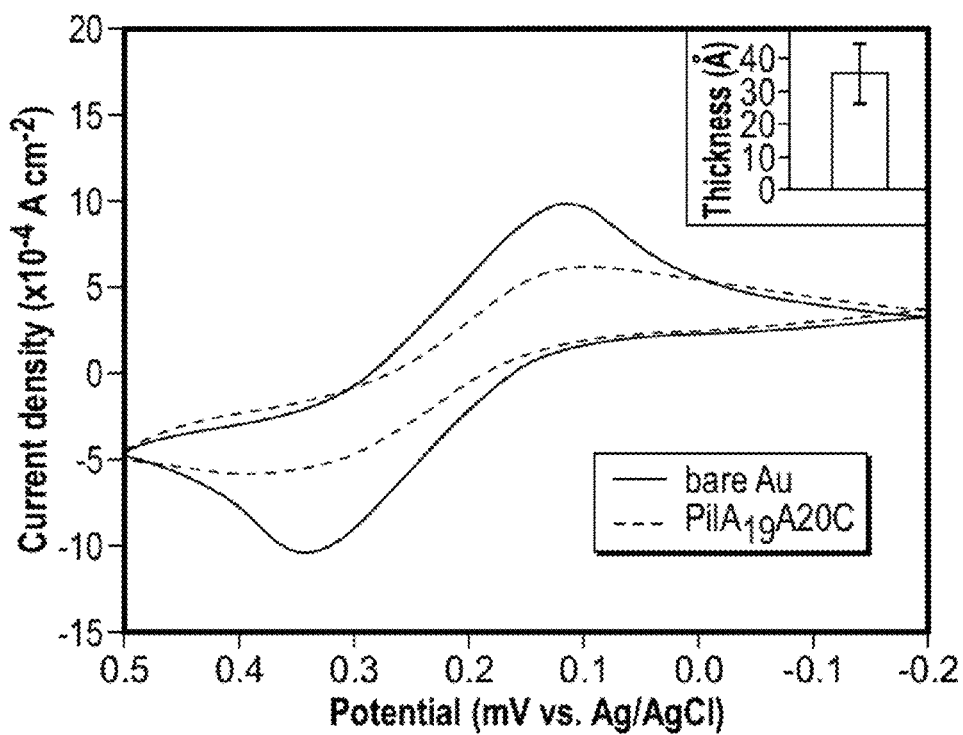
FIG. 14 is a graph showing deposition of PilA$_{19}$-A20C subunits on a gold electrode. Cyclic voltammogram of bare gold (black line), and undecanethiol SAM (dashed line). Data recorded at room temperature in 100 mM sodium phosphate pH 7.0 containing 100 mM NaCl, and 5 mM K$_3$[Fe(CN)$_6$] at a potential scan rate of 100 mV s$^{-1}$. Inset shows the thickness of PilA$_{19}$-A20C monolayer measured by ellipsometry.

Ellipsometry measurements indicated the presence of a film with a thickness of 35.582±9.110 Å (inset of FIG. 14). The dimensions of full length PilA (61 amino acid residues) from G. sulfurreducens are approximately 80 Å in length and 1 Å in diameter. For the cysteine modified truncation (42 amino acid residues) a length of roughly 55 Å would be expected. The thickness obtained by ellipsometry is about 65% of the expected length. As a reference, the tilt angle of alkanethiol SAM is typically around 30 degrees. The film thickness and the lack of any structures under SEM examination indicate that the assembly of pilin monomers into pili did not occur.

Figure 15:
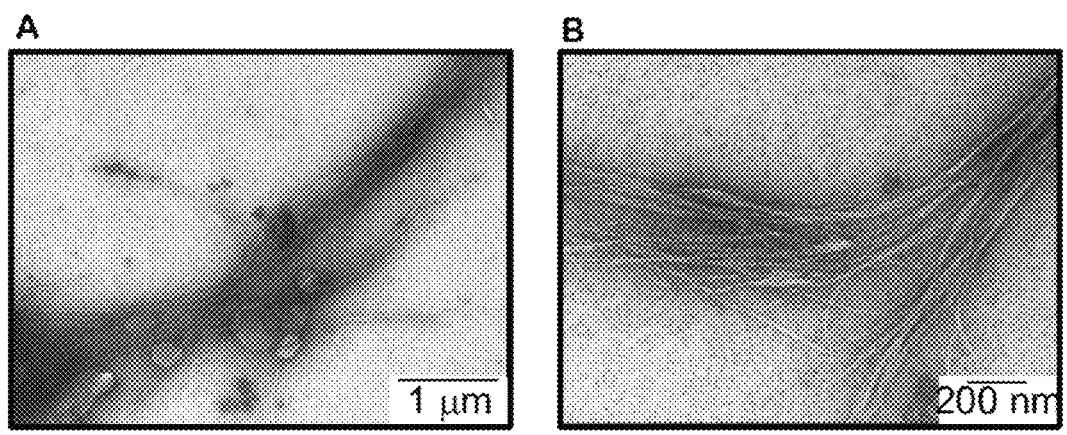
FIGS. 15A and 15B are images showing in-vitro assembly of PilA$_{19}$-A20C fibers. The transmission electron microscopy images were collected at an accelerating voltage of 100 kV.

FIG. 14 shows CV curves of bare gold and gold incubated overnight with pilin subunits. Both curves display the characteristic duck shape with distinctive oxidation and reduction peaks. The current density decreases after the incubation with pilin subunits. This indicates the formation of a pilin monolayer that does not block electron transfer with electrode. This is consistent with the pilins' electronically interfacing the gold electrode. Alternatively, the presence of pinholes in the monolayer or incomplete surface coverage would allow electron transfer between the electrode and the redox species in solution. FIGS. 15A and 15B are images showing in-vitro assembly of PilA$_{19}$-A20C fibers. The transmission electron microscopy images were collected at an accelerating voltage of 100 kV.

Example 3

Genetic Manipulation of Redox-Active Amino Acids in Pilin Nanowires

This Example illustrates that manipulation of redox-active amino acids in the nanowire pilins enables the generation of nanowires with altered conductive properties.

Since the rates of electron hopping are linearly dependent on the distance between relay amino acids, site-directed mutagenesis was used to genetically manipulate the distance between tyrosine residues in the pilus. Tyrosine Y57 was replaced with an alanine (Y57A) or with a phenylalanine (Y57F). The tyrosine at position 57 (Y57) was a good candidate because it is at the C-terminal end of the pilin and exposed to the pilus exterior, so its replacement did not radically affect the pilus structure.

The mutated pilin genes were expressed in trans in a PilA– mutant background using the expression vector pRG5 (Coppi et al., Appi. Environ. Microbiol. 67: 3180-87 (2001)); Leang et al., BMC Genomics 10, 331 (2009). This complementation produced strains that expressed pili with the Y57F substitution.

Using the same approach, the negatively charged amino acids in the tyrosines' vicinities (D53, D54, and E60) were replaced with a non-charged amino acid, alanine (A), which does not affect the structure of the pilin. Single, double and triple mutations were made. Thus, mutant nanowires with the single E60A replacement, double D53A D54A replacement, and triple E60A D53A D54A replacement were generated. A mutant strain of G. sulfurreducens that fails to produce pili nanowires (PilA–) was used as a negative control.

Mutagenesis was performed using the Stratagene QuikChange mutagenesis kit. This mutagenesis tool uses pfu Turbo as a polymerase to replicate template DNA from complementary primers containing mutagenic nucleotides. The mutagenic oligonucleotides used for site-directed mutagenesis are shown below in Table 7.

TABLE 7

Oligonucleotides for Mutagenesis

| Name SEQ ID | Oligonucleotide sequence | Nucleotide replacement position(s) |
|---|---|---|
| Y₅₇F NO: 12 | 5' C GCA TTT GCT GAT GAT CAA ACC TTT CCG CCC GAA AG 3' | 200 |
| Y₃₂F NO: 13 | 5' CGT GTC AAG GCG TTC AAC AGC GCG GCG 3' | 115 |
| Y₂₇F NO: 14 | 5' CCG CAG TTC TCG GCG TTT CGT GTC AAG GC 3' | 100 |
| E₆₀A NO: 15 | 5' GAT GAT CAA ACC TAT CCG CCC GCA AGT TAA 3' | 209 |
| D₅₃A D₅₄A NO: 16 | 5' GAG TCC GCA TTT GCT GCT GCT CAA ACC TAT CCG CCC 3' | 188, 191 |
| D₅₃A D₅₄A E₆₀A NO: 17 | 5' GAG TCC GCA TTT GCT GCT GCT CAA ACC TAT CCG CCC GCA AGT TAA 3' | 188, 191, 209 |
| S₆₁A NO: 18 | 5' GAT GAT CAA ACC TAT CCG CCC GAA GCT TAA 3' | 211, 212 |

The name of the mutated nanowire is provided in the first (left) column, where the nanowire name is the original amino acid one-letter symbol followed by the position of the amino acid (as a subscript), which is then followed by the one-letter symbol for the replacement amino acid. The middle column shows the oligonucleotide sequence with the mutagenized codon (in bold) and mutated nucleotide(s) (underlined). The positions of the replaced nucleotides in the pilA nucleotide sequence are shown in the last (right).

The amino acid sequences of the nanowire peptides encoded by these nucleic acids are as follows.

The Y₅₇F peptide is shown below as SEQ ID NO:19.

```
 1    FTLIELLIVV AIIGILAAIA IPQFSAYRVK AYNSAASSDL
41    RNLKTALESA FADDQTFPPE S
```

The Y₃₂F peptide is shown below as SEQ ID NO:20.

```
 1    FTLIELLIVV AIIGILAAIA IPQFSAYRVK AFNSAASSDL
41    RNLKTALESA FADDQTYPPE S
```

The Y₂₇F peptide is shown below as SEQ ID NO:21.

```
 1    FTLIELLIVV AIIGILAAIA IPQFSAFRVK AYNSAASSDL
41    RNLKTALESA FADDQTYPPE S
```

The E₆₀A peptide is shown below as SEQ ID NO:22.

```
 1    FTLIELLIVV AIIGILAAIA IPQFSAYRVK AYNSAASSDL
41    RNLKTALESA FADDQTYPPA S
```

The D₅₃A D₅₄A peptide is shown below as SEQ ID NO:23.

```
 1    FTLIELLIVV AIIGILAAIA IPQFSAYRVK AYNSAASSDL
41    RNLKTALESA FAAAQTYPPE S
```

The D₅₃A D₅₄A E₆₀A peptide is shown below as SEQ ID NO:24.

```
 1    FTLIELLIVV AIIGILAAIA IPQFSAYRVK AYNSAASSDL
41    RNLKTALESA FAAAQTYPPA S
```

The S₆₁A peptide is shown below as SEQ ID NO:25.

```
 1    FTLIELLIVV AIIGILAAIA IPQFSAYRVK AYNSAASSDL
41    RNLKTALESA FADDQTYPPE A
```

The constructs were transfected into *G. sulfurreducens* strain PCA. Cells were routinely grown at 30° C. in NB medium (Coppi et al., APPL. ENVIRON. MICROBIOL. 67: 3180-87 (2001)) supplemented with 15 mM acetate and 40 mM fumarate (NBAF) before been transferred three times in a modified fresh water (FW) medium (Lovley & Philips, APPL. ENVIRON. MICROBIOL. 54: 1472-80 (1988)), supplemented with 15 mM acetate and 40 mM fumarate (FWAF). Briefly, a concentrated (10×) basal FW medium stock containing $NaHCO_3$ (25 g/L), $NaH_2PO_4 \cdot H_2O$ (0.6 g/L), $NH_4Cl$ (2.5 g/L), and KCl (1.0 g/L) was prepared. The electron donor and acceptor were prepared as sterile concentrated stocks (0.75 M sodium acetate and 1 M sodium fumarate, respectively) and the pH of the stock solutions was adjusted to 7 prior to autoclaving. Vitamins were prepared as separate solutions as described by Balch et al. (MICROBIOL. REV. 43: 260-96 (1979)). Trace minerals were prepared as described by Lovley et al. (APPL. ENVIRON. MICROBIOL. 48: 81-87 (1984)), except that $ZnSO_4$ was replaced with $ZnCl_2$ (0.13 g/L), and $Na_2WO_4 \cdot 2H_2O$ (0.025 g/L) was added. FWAF medium contained FW stock (96 ml/L), 0.75 M sodium acetate (20 ml/L), 1 M sodium fumarate (40 ml/L), vitamin solution (10 ml/L), mineral solution (10 ml/L) and $ddH_2O$ to a final volume of 1 L. The medium was dispensed in pressure tubes or serum bottles, sparged with $N_2$:$CO_2$ (80: 20) to remove dissolved oxygen and sealed with butyl rubber stoppers and aluminum tear off seals (Wheaton) prior to autoclaving. For pili induction, exponentially-growing cells from FWAF cultures grown at 30° C. were subcultured in 100 ml of fresh FWAF with 30 mM acetate and 40 mM fumarate and the cells were incubated at 25° C. until they reached early stationary phase (ca. 72 h).

The conductive properties of the mutant nanowires were measured by testing the mutant cells compared to wild-type and PilA– cells in microbial fuel cell assays. Two measurements were made: (i) coulombic efficiency, which measures the amount of electron donor converted into current by the cells, and (ii) the coulombic rates, which measure the coulombic efficiency per day and are proportional to the electron transfer rates along the nanowires of the biofilms formed on the anode electrode.

Figure 16A:
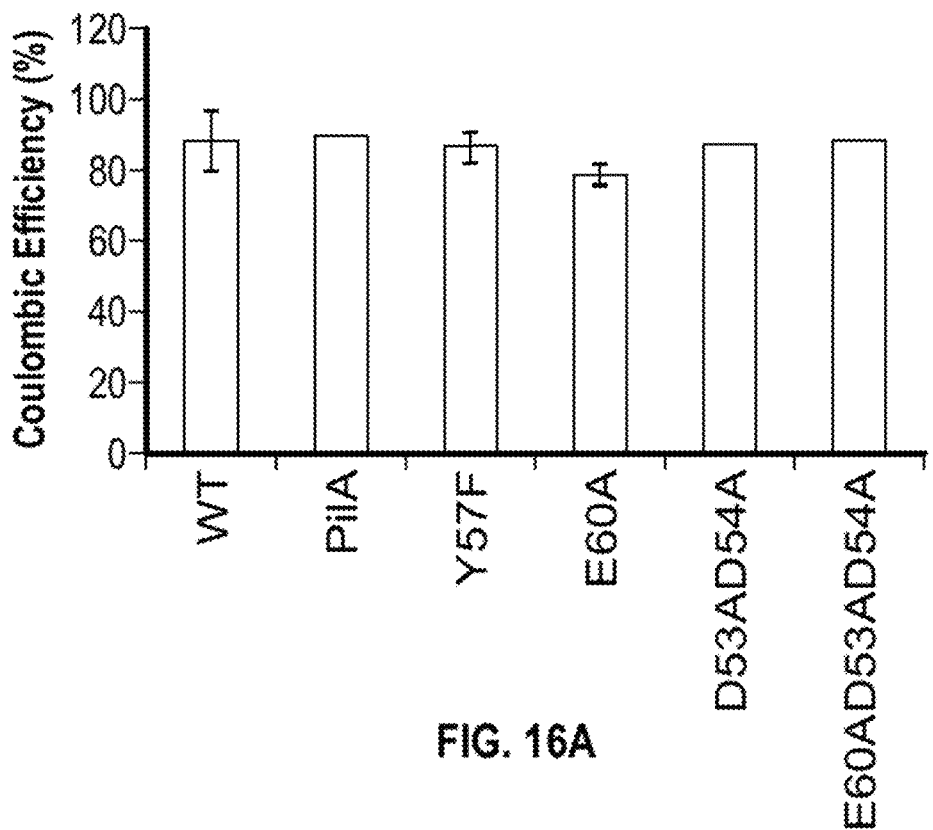
FIGS. 16A and 16B are graphs which show that nanowire conductivity can be manipulated via genetic engineering of the *Geobacter* pilin subunit. Pilin subunits were engineered by using a nanowire peptide having an Y$_{57}$F replacement as starting material (SEQ ID NO:19). The replacement of tyrosine at position 57 with phenylalanine removed one of the tyrosines 20 used for electron hopping along the nanowires. Single mutant (E$_{60}$A), double mutant (D$_{53}$A, D$_{54}$A) and triple mutant (E$_{60}$A, D$_{53}$A, D$_{54}$A) peptides were made where negatively charged amino acids were replaced with alanine residues at position 60, position 53 and/or position 54, as described in the Examples. The negatively charged amino acids act normally as proton acceptors of the tyrosines during electron transfer.
Figure 16B:
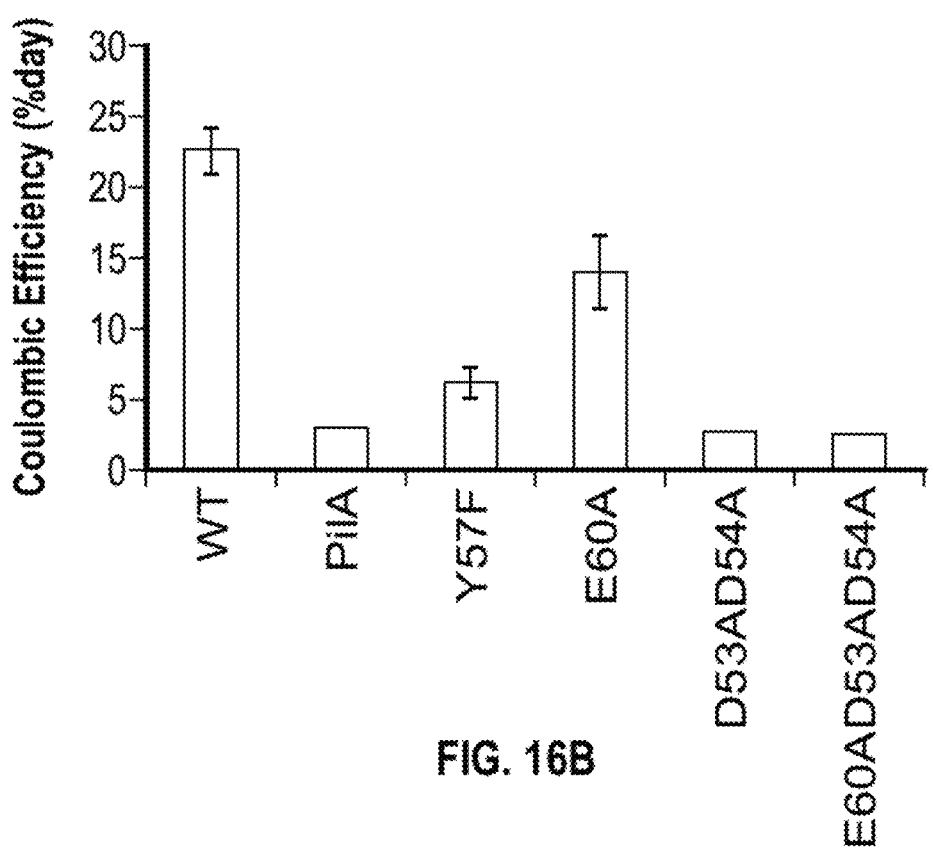

Because the nanowires are the electrical connections of the cells in the anode biofilm, defects in their conductivity translated into defects in the measured coulombic rates. As shown in FIG. 16A, the coulombic efficiency was the same in all the strains, meaning that all the cells converted the same amount of electron donor, acetate, into electricity thus ruling out any metabolic defects of the mutations. However, the amino acid replacements resulted in defects in the coulombic rates (FIG. 16B). The Y57F substitution produced nanowires with rates of electron transfer close to a mutant that did not produce the nanowires (PilA–), suggesting that the interruption of the electron pathway along the nanowire through the removal of one of the "stepping stones" (a tyrosine) produced nanowires with increased resistance to the passage of electrons. The replacement of a single negatively-charged amino acid (E60A), which may serve as a proton acceptor during electron hopping via tyrosines, resulted in a 1.7-fold decrease in the electron transfer rates. Double (D53A D54A) and triple (D53A D54A E60A) mutants produced pili but had coulombic rates comparable to a pilus-deficient mutant.

Figure 17:
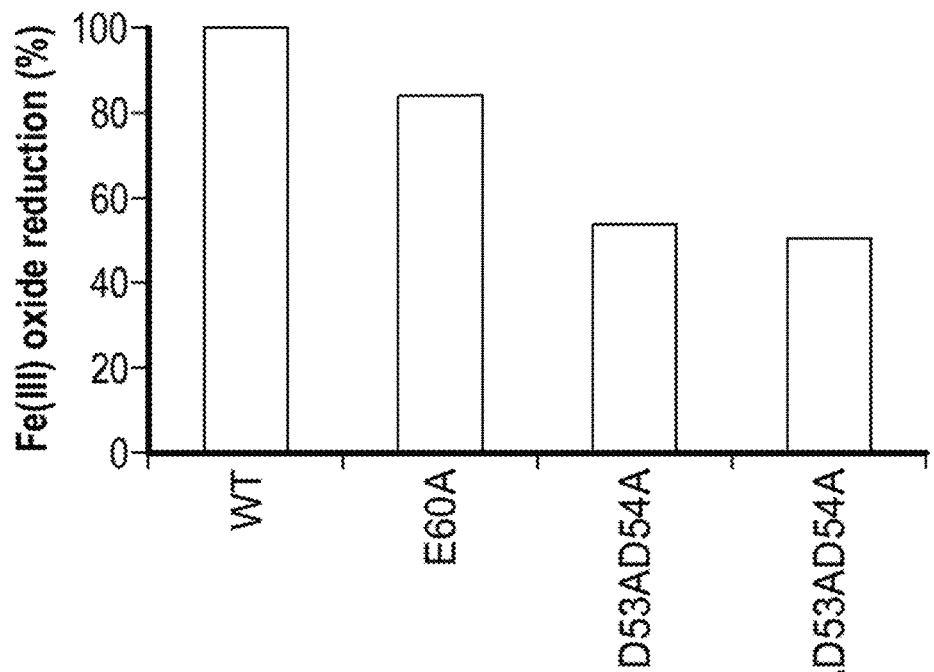
FIG. 17 is a graph illustrating electron transfer to Fe(III) oxides by cells expressing native Wild Type (WT) nanowires or nanowires composed of pilins carrying single (E60A), double (D53A D54A) and triple (E60A D53A D54A) replacements of negatively charged amino acids. The negatively charged amino acids act as proton acceptors of the 5 tyrosines during electron transfer. Their replacement with alanine resulted in nanowires with reduced ability to reduce Fe(III) oxides.

Another measure of the nanowire conductivity is its ability to reduce insoluble Fe(III) oxides into soluble Fe(II), which can be measured to indirectly determine the rates of Fe(III) oxide reduction. As shown in FIG. 17, the replacement of negatively charged amino acids also gave rise to a defect in the reduction of Fe(III) oxides.

These results demonstrate that amino acids in the pilin nanowire subunit can be selectively replaced to modulate the conductive properties of the nanowires pili.

Example 4

Genetic Manipulation of Attachment Points in Pilin Nanowire

This example illustrates that manipulation of non-redox-active amino acids can modulate other functions of the nanowires.

Site-directed mutagenesis was used to replace a C-terminal serine (S61) with an alanine, and generate cells that express a mutant nanowire S61A.

Figure 18A:
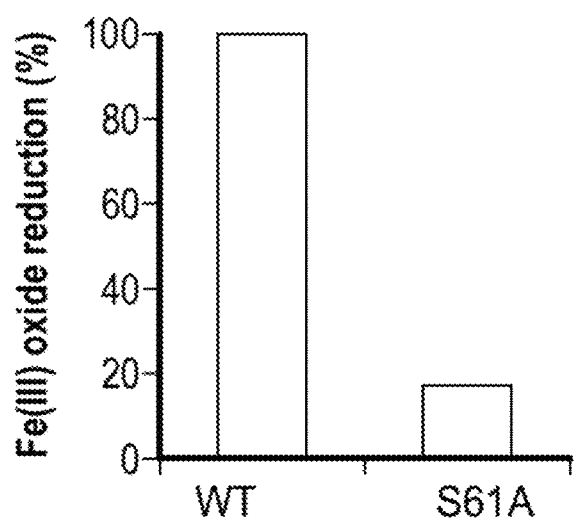
FIGS. 18A-18C are graphs which illustrate that the adhesive properties of nanowires can be manipulated via genetic engineering. Nanowires were engineered with a S61A replacement to remove 10 the glycosylation of serine at position 61. The replacement resulted in nanowires with reduced binding but same conductivity, as indicated by the defect in Fe(III) oxide reduction (FIG. 18A), the maintenance of the coulombic efficiency (FIG. 18B) and the electron transfer rates to electrodes (FIG. 18C) in microbial fuel cells.
Figure 18B:
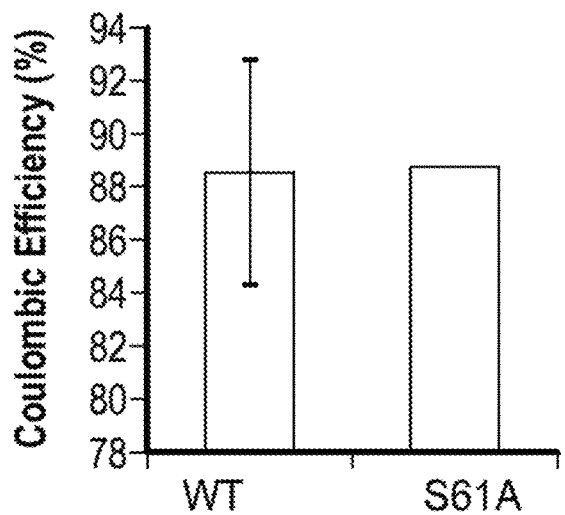
Figure 18C:
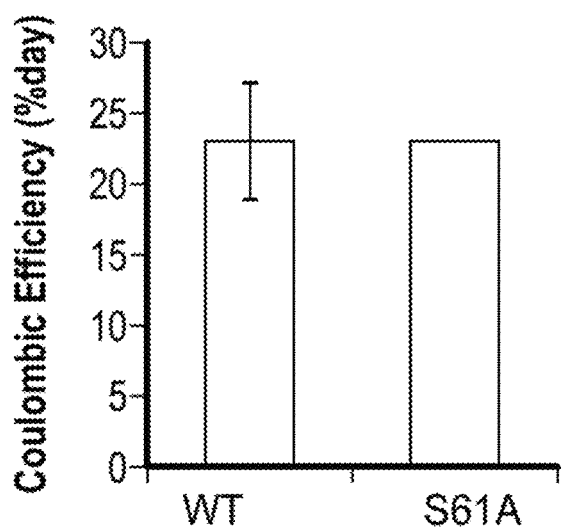

As shown in FIG. 18A, the S61A nanowires had a defect in Fe(III) oxide reduction that may be caused by defective binding or defective nanowire conductivity of the nanowires. Thus, the conductive properties of the S61A nanowires were tested in microbial fuel cell assays. In this case, the coulombic efficiencies and coulombic rates were the same in the wild-type and S61A nanowires, demonstrating that the conductive properties of the nanowires were unaltered.

Thus, the defect in Fe(III) oxide reduction but the existence of wild-type coulombic rates in the S61A nanowires indicates that the replacement of serine at position 61 affected the adhesive properties of the nanowires. Thus, genetic engineering can be used to manipulate properties of the nanowires other than conductivity to suit specific applications such as the controlled deposition of the nanowires on various surfaces.

Example 5

Pili Expression Promotes Extracellular U(VI) Reduction

Materials and Methods
Strains and Culture Conditions

Wild-type (WT) $G.\ sulfurreducens$ PCA (ATCC 51573), a pilin-deficient mutant (PHA) (19), and its genetically complemented strain (pRG5::pilA) (19) were grown in fresh water (FW) medium supplemented with 15 mM acetate and 40 mM fumarate. All cultures were incubated at pili-inducing temperatures (25° C.), except for the nonpiliated $WT_{P-}$ controls, which were grown at 30° C.

Cells were routinely revived from frozen stocks in NB medium (51) supplemented with 15 mM acetate and 40 mM fumarate (NBAF) and incubated at 30° C. The cultures were transferred three times in fresh water (FW) medium (S2), prepared with the modifications described below, and supplemented with 15 mM acetate and 40 mM fumarate (FWAF). The electron donor and acceptor were prepared as autoclaved concentrated stocks (0.75 M sodium acetate and 1 M sodium fumarate at pH 7, respectively). FW medium was prepared from a concentrated (10×) basal FW medium stock containing $NaHCO_3$ (25 g/L), $NaH_2PO_4.H_2O$ (0.6 g/L), $NH_4Cl$ (2.5 g/L), and KCl (1.0 g/L). Vitamins were prepared as separate solutions as previously described (S3). Trace minerals were prepared as previously described (S4), except that $ZnSO_4$ was replaced with $ZnCl_2$ (0.13 g/L), and $Na_2WO_4.2H_2O$ (0.025 g/L) was added. FWAF medium contained FW stock (96 ml/L), 0.75 M sodium acetate (20 ml/L), 1 M sodium fumarate (40 ml/L), vitamin solution (10 ml/L), mineral solution (10 ml/L). The medium was dispensed in pressure tubes or serum bottles, sparged with $N_2:CO_2$ (80:20) to remove dissolved oxygen and sealed with butyl rubber stoppers and aluminum tear off seals (Wheaton) prior to autoclaving. Unless otherwise indicated, all cultures were incubated at 30° C.

U(VI) Resting Cell Suspension Assays

Resting cell suspensions were prepared as described elsewhere (13), except that cells were harvested from mid-log phase cultures ($OD_{600}$, 0.3-0.5) and resuspended in 100 ml reaction buffer with 20 mM sodium acetate to a final $OD_{600}$ of 0.1. Heat-killed controls were prepared by autoclaving the cultures for 30 min. Suspensions were incubated for 6 h at 30° C. with 1 mM uranyl acetate (Electron Microscopy Sciences), as previously described (13). After incubation, 500-µl samples were withdrawn, filtered (0.22-µm Millex-GS filter, Millipore) to separate the cells, acidified in 2% nitric acid (500 µl), and stored at −20° C. All procedures were performed anaerobically inside a vinyl glove bag (Coy Labs) containing a $H_2:CO_2:N_2$ (7:10:83) atmosphere. The amount of U(VI) removed from solution was estimated from the initial and final concentration of U(VI) measured in the acidified samples using a Platform Inductively Coupled Plasma Mass Spectrometer (ICP-MS) (Micromass, Thermo Scientific).

X-ray Adsorption Spectroscopy (XAS) Analyses

Resting cells incubated with U for 6 h were harvested by centrifugation (13,000×g, 10 min, 4° C.) and loaded into custom-made plastic holders, triply packaged in Kapton® film and sealed with Kapton® tape (DuPont), under anaerobic conditions. Samples were stored at −80° C. and kept frozen during XAS measurements, which were performed with a multielement Ge detector in fluorescence mode, using the PNC-CAT beamline 20-BM at the Advanced Photon Source (Argonne National Laboratory) and standard beamline parameters, as described elsewhere (37). XANES measurements were used to calculate the relative amount of U(VI) to U(IV) by linear combination fitting of the spectrum with U(VI) and U(IV) standards. The spectra were energy aligned by simultaneously measured uranyl nitrate standards.

Transmission Electron Microscopy (TEM)

After U exposure, resting cells were adsorbed onto 300-mesh carbon-coated copper grids (Ted Pella), fixed with 1% glutaraldehyde for 5 min, and washed 3 times with $ddH_2O$ for 2 min. Unstained cells were directly imaged with a JEOL100CX operated at a 100-kV accelerating voltage.

Vitality and Viability Assays

The RedoxSensor™ Green vitality assay (Molecular Probes) was used to measure the cell's vitality (broadly defined as the levels of activity of cell's vital reactions) remaining after U exposure and in reference to controls not exposed to U. This reagent yields green fluorescence when modified by the bacterial reductases, which are mostly located in the electron transport system of the cell envelope. Resting cells were harvested in a microcentrifuge (12,000× g), washed, and resuspended in a 100 µl Tris-Buffered Saline (TBS) before mixing it with an equal volume of a working concentration of the dye. Fluorescence was measured in two biological replicates, with two technical replicates each, using a SpectraMax M5 plate reader (Molecular Devices) with an excitation of 490 nm and emission of 520 nm. Cell viability after U exposure in comparison to controls without U was assayed by recovering the resting cells in NB medium with acetate and fumarate (NBAF) and measuring the length of the lag phase, as described before (54).

Prior to inoculation, resting cell suspensions were gassed for 15 min with filtered-sterilized air so as to reoxidize the U deposits (13) without compromising *G. sulfurreducens* viability (54). Cells were harvested by centrifugation (1,200×g, 5 min), resuspended in 1 ml of wash buffer (final $OD_{600}$ of 0.4), and mixed with 10 ml of NBAF in pressure tubes. The cultures were incubated at 25° C. and growth was periodically monitored as $OD_{600}$.

Pili Induction at Suboptimal Growth Temperatures

WT controls expressing pili ($WT_{P+}$) were obtained by growing WT cells at suboptimal growth temperatures (25° C.). Bacterial pili expression is often thermoregulated (S5), an adaptive mechanism that enables bacteria to rapidly assemble the pili in environments where pili functions are advantageous. As in other bacteria (S7), pili production in *Geobacter* is induced at suboptimal growth temperatures (25° C.) mimicking the suboptimal growth conditions that the cells encountered during the reduction of Fe(III) oxides. In contrast, growth at 30° C. prevents pili assembly produced by a pili-deficient strain, $WT_P$.

EXAFS Analyses

The uranium EXAFS spectra were processed using the methods (S9) in Athena (S10) and were modeled using FEFFIT (S11) with theoretically generated models from FEFF 7.02 (S12), as described elsewhere (S13). Multiple scattering paths from distant C3 and Odist atoms were also included in the model, yet did not have a significant contribution. The coordination number for U-Oax (Noax values) obtained from EXAFS measurements of 3 to 4 biological replicates from at least two independent experiments also was used to estimate the amount of U(VI) reduced to U(IV) in each sample. For example, a Noax value of 0.3 was obtained for one of the biological replicates of the $WT_{P+}$ (as given in Table 8). 100% of U(VI) would have a U-Oax coordination number of 2.0. Therefore the amount of U(VI) that corresponds to the $WT_{P+}$ Noax is 0.3/2.0=0.15. This indicates that there is 15% U(VI) and 85% U(IV) in this sample.

Pili Purification, Quantification, and Biochemical Characterization

Pili were purified as detergent-insoluble fractions from cells first lysed by sonication and treated with RNase, DNase and lysozyme enzymes (S14). Three biological replicates were used for each strain. Cell membranes and proteins in the extracts were solubilized with sodium dodecyl sulfate (SDS, 1% final concentration) and separated by preparative 12% polyacrylamide gel electrophoresis (5% stacking gel, 40 mA for 5 h) using a Prep Cell 491 apparatus (Bio-Rad). The detergent-insoluble fraction, which did not enter the stacking gel, was recovered by aspiration, washed in $ddH_2O$, extracted once with 95% ethanol (Decon Laboratories), and dried in a SpeedVac system (Savant Instruments Inc.) at room temperature for 20 min.

The dry sample was resuspended in 1 ml of $ddH_2O$ and vortexed for 60 seconds to break up large clumps before extracting and poorly bound, soluble protein with 0.2 M glycine (pH 1.5, adjusted with HCl; Invitrogen™) at 100° C. for 10 min. The insoluble fraction was recovered by centrifugation (16,000×g, 25 min, 4° C.), washed five times with $ddH_2O$, and dried in a SpeedVac at room temperature prior to storing it at −20° C. The amount of pili protein was measured after resuspending the dry samples in 10 mM CHES buffer (pH 9.5), incubating at 4° C. overnight, mixing 1:1 with the working reagent solution of the Pierce Microplate BCA protein assay kit (reducing agent compatible, Thermo). The samples were incubated at 60° C. for 1 h before spectrophotometric measurements. BSA was used as a standard For PAGE analyses, dried preparations of purified pili were resuspended in 5 µl of $ddH_2O$ containing 10% (w/v) Octyl-β-D-Glucopyranoside (OG) (Sigma, 98%) and incubated at room temperature for 2 h. The samples were diluted with 5 volumes of $ddH_2O$ to reduce the OG concentration to 2% (v/v) and incubated for an additional 24 h period at room temperature. The OG-treated sample was boiled in SDS-PAGE sample buffer (S15) and subjected to electrophoresis through a 10-20% Tris/Tricine ReadyGel (Bio-Rad) using a Mini Protean Tetra Cell apparatus (Bio-Rad). After electrophoresis, the gels were silver stained using the Pierce™ Silver Stain for Mass Spectrometry kit (Thermo Scientific), following the instructions supplied by manufacturer, and scanned.

The migration of the molecular mass standards in the gradient gel was estimated and fitted a polynomial distribution ($R^2$=0.95523), which was used to calculate the molecular mass of unknown bands. Duplicate gels were also electrophoretically transferred to a PVDF membrane (Hy-Bond LFP™, Amersham GE Healthcare) at 25 V for 150 min using a Mini Protean Tetra Cell apparatus (Bio-Rad). The Amersham ECL Plex Western blotting kit was used for the electrophoretic transfer and membrane blocking, following manufacturer's recommendations. After blocking, the membrane was incubated in 10 ml antibody diluent solution (90 min, room temperature, gentle agitation) containing a 1:5,000 dilution of the primary antibody (rabbit α-PilA polyclonal antibodies raised against the 42 C-t amino acids of *G. sulfurreducens* PilA protein) and a 1:2,500 dilution of goat α-rabbit IgG antibodies conjugated to the Cytm 5 fluorescence dye (ECL™ Plex, Amersham GE Healthcare).

The membrane was washed for 5 minutes in wash buffer (TBS-T, pH 7.4, 0.1% Tween 20) and rinsed three times in wash buffer without Tween 20. The protein bands that hybridized with the primary antibodies were visualized after scanning the membrane blot with a Typhoon imager operated in fluorescence mode (excitation at 633 nm, 670 BP 30 filter, and PMT setting at 600 V).

qRT-PCR Gene Expression Analyses

Quantitative reverse-transcriptase PCR (qRT-PCR) was used to quantify pilA and recA transcripts in RNA extracted from resting cells of the WTP+ and WTP− strains before and after incubation with uranyl acetate for 6 h. WTP+ controls incubated in the same reaction buffer without uranyl acetate also were included. RNA was extracted using the TRIzol reagent (Life Technologies Corp., Carlsbad, Calif.), and treated with RQ1 RNase-free DNase (Promega, Madison, Wis.) according to the manufacturer's instructions. Reverse transcription was performed using Superscript III Reverse Transcriptase (Life Technologies Corp., Carlsbad, Calif.) following manufacturer's recommendations. Primer pairs RT_ORF02545_F and RT_ORF02545_R were used for pilA and recA660f and recA737r were used for recA. For qRT-PCR, the cDNA generated after reverse transcription was diluted 1:1000 in a 25-μl reaction that contained each primer (5 μM) and SYBR® Green MasterMix (Applied Biosystems, Foster City, Calif.), according to the manufacturer's instructions. Samples were amplified using a Bio-Rad (Hercules, Calif.) iCycler (iQ5 Multicolor Real-Time PCR Detection System).

The comparative CT method was used to calculate the relative expression of the pilA gene using the recA constitutive expression as internal control. Briefly, the ΔCt value (CT (pilA)–CT (recA)) was calculated for triplicate biological replicates before (0 h) and after (6 h) incubation with U(VI) acetate. The average of the difference between the 6 h and 0 h CT values was used to calculate the ΔΔCT. The relative fold change in pilA expression versus the recA internal control was calculated with the formula 2-ΔΔCT.

Transmission Electron Microscopy (TEM) and Confocal Laser Scanning Microscopy (CLSM)

Detergent-insoluble fractions were examined by TEM and CLSM. For TEM, an aqueous solution of purified pili was adsorbed on a carbon-copper grid (Mesh 300, Electron Microscopy Sciences), negatively stained with 1% (w/v) uranyl acetate in distilled water, and examined with a JEOL 100 CX electron microscope (Japan Electron Optic Laboratory) operated at 100 kV. For CLSM, detergent-insoluble fractions were dissolved in phosphate buffer saline (PBS, pH 7), adsorbed onto glass coverslips for 30 min, washed with PBS and fixed with 3.7% paraformaldehyde in PBS. The samples were then incubated for 30 min in PBS-1% BSA, before overnight incubation at 4° C. with a 1:100 dilution anti-PilA primary antibody in PBS-1% BSA.

After three washes in PBS-1% BSA, the samples were incubated with a 1:1,000 dilution of anti-rabbit antibodies conjugated to the Alexa Fluor 488 dye (Molecular Probes, Life Technologies Corp.) for 1 h. The coverslips were then washed 3 times with PBS and examined with a Zeiss LSM Pascal confocal microscope equipped with a Plan-Neofluar 63× oil objective (excitation, 488 nm; emission, 505-535 nm).

TEM and Energy Dispersive Spectroscopy (EDS) Analyses

Cells from resting cell suspensions incubated for 6 h with uranyl acetate were adsorbed onto 300-mesh carbon-coated copper grids (Ted Pella, Redding, Calif.), fixed with 1% glutaraldehyde for 5 min, and washed 3 times with ddH$_2$O for 2 min. Imaging and elemental analysis of the extracellular uranium precipitates were performed with a JEOL 2200FS operated at 200 kV and an Energy Dispersive Spectroscopy (EDS) detector.

For thin sections, cells were harvested by centrifugation (1,200×g, 30 min, room temperature) and prepared as previously described, except that a Power Tome XL (RMC Products, Boeckler Instruments, Tucson, Ariz.) was used for sample sectioning. Thin sections were imaged with a JEOL100CX operated at 80 kV. Approximately 400-500 cells from randomly taken, thin-sectioned fields were also examined for periplasmic mineralization. A cell was considered to have a mineralized periplasm when it contained both a fully mineralized outer membrane and generalized mineralization in the periplasm or inner membrane.

SDS-PAGE and Protein Staining

Outer membrane c-cytochromes were mechanically detached from all the strains and isolated as previously described. A mutant deficient in the outer membrane c-cytochrome OmcS and grown at 25° C. was included as a control. Proteins (2.5 μg) in the supernatant fluids were separated by Tris-Glycine denaturing polyacrylamide gel electrophoresis using a 12% Mini-Protean TGX gel (Bio-Rad). The Novex Sharp molecular weight markers (Life Technologies Corp.) were used as standards. Reducing agents were omitted from the SDS-sample buffer and the samples were loaded onto the gel without boiling to prevent the loss of heme groups. C-type cytochromes were detected as heme-stained bands using N,N,N',N'-tetramethylbenzidine, as previously described. After heme-staining, the gels were photographed, destained with 70 mM sodium sulphite, and silver-stained for total protein with the Pierce silver stain for Mass Spectrometry (Thermo).

Pili Expression Promotes U(VI) Reduction

Figure 19:
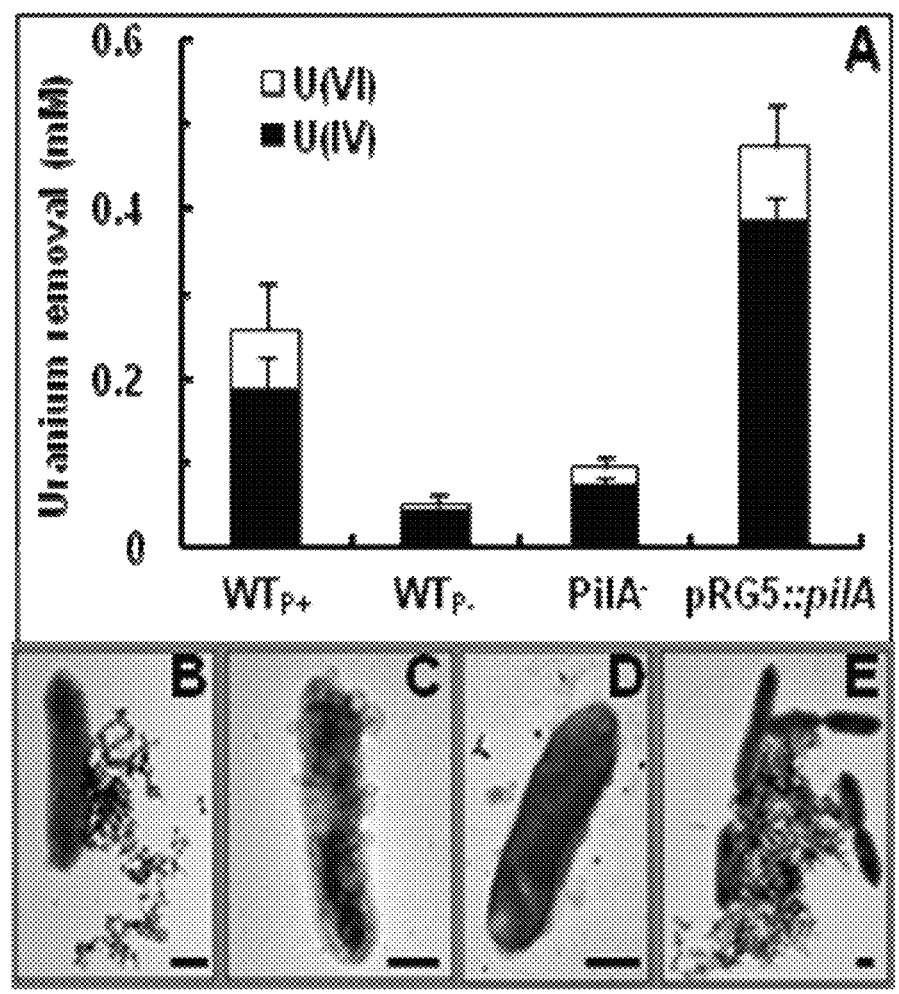
FIGS. 19A-19E include a bar graph (FIG. 19A) showing Uranium (VI) (U(VI)) to U(IV) reduction and TEM images (FIGS. 19B-19E) of unstained whole cells showing the subcellular U deposit localization in the Wild Type cell incubated at 25° C. (WTP+) (FIG. 19B), Wild Type cell incubated at 30° C. (WTP−) (FIG. 19C), PilA− (FIG. 19D) and pRG5::pilA (FIG. 19E) strains. Bar, 0.5 μm.
Figure 20:
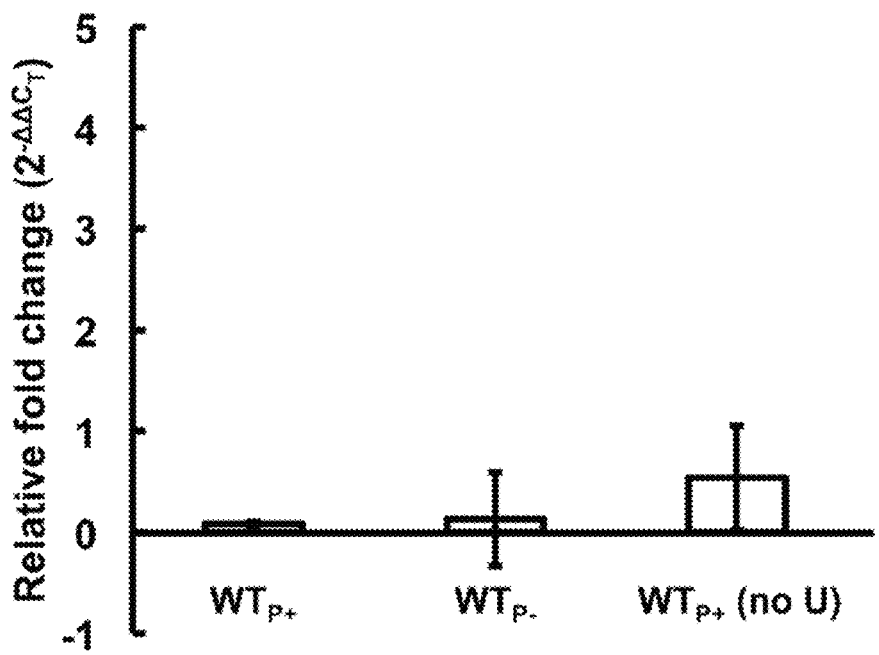
FIG. 20 is a graph showing fold change expression of pilA relative to recA in resting cell suspensions of the WTP+ and WTP− strains after 6 h of incubation with 1 mM U(VI) acetate. A WTP+ control incubated in reaction buffer without U(VI) acetate also is shown (WTP+ (no U)).
Figure 21:
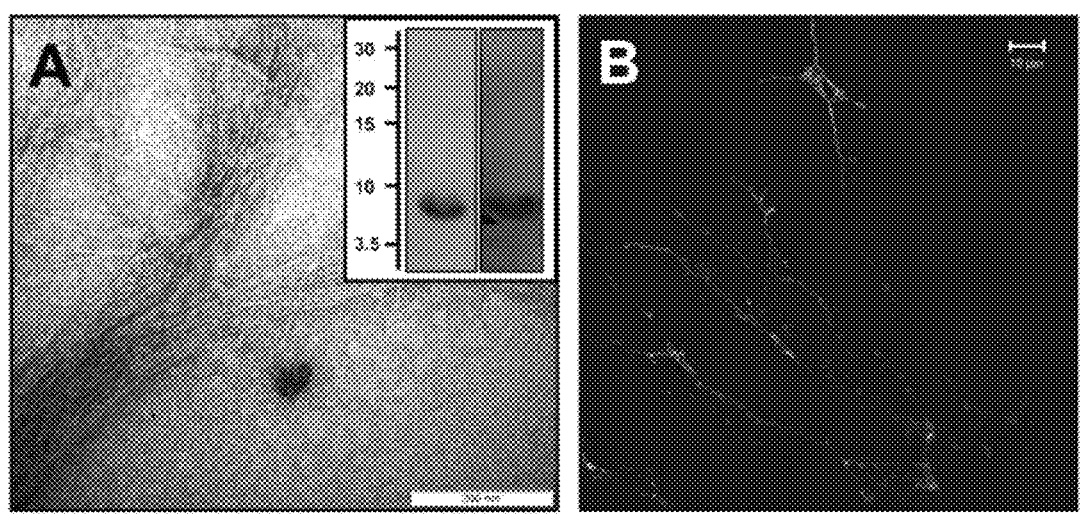
FIGS. 21A and 21B are TEM images (FIG. 21A) and Confocal Laser Scanning Microscopy micrographs (CLSM) (FIG. 21B) of negatively-stained and anti-PilA immunodetected pilus fibers isolated as detergent-insoluble fractions in the WTP+. Inset in (FIG. 21A): SDS-PAGE Tricine gel (left) and Western blot using anti-PilA polyclonal antibodies (right) showing the depolymerization of the purified pili into the PilA peptide subunits. Numbers at left are molecular mass standards in KDa and were used to estimate the apparent mass of the PilA band (6.6 kDa, as predicted for the mature PilA based on amino acid sequence).

The correspondence between pili expression and U immobilization was examined by monitoring the removal of U(VI) acetate from solution by resting wild-type cells incubated at 25° C. (WTP+) or 30° C. (WTP−) to induce or prevent pili assembly, respectively. Controls with a pilin-deficient mutant (PilA−) and its genetically complemented strain (pRG5::pilA) were also included. The piliated strains WTP+ and pRG5::pilA removed substantially more U(VI) from solution than the nonpiliated strains WTP− and PilA− (FIG. 19A). The activity was biological in nature, inasmuch as heat-killed WTP+ and WTP− controls did not remove U(VI) significantly (0.02±0.04 and 0.05±0.02 mM, respectively). X-ray Absorption Near Edge Structure (XANES) spectroscopy confirmed the reductive nature of the U removal activity and measured an average of 70-85% U(IV) in all samples (FIG. 19A). Furthermore, the expression of the pilA gene relative to the internal control recA did not change during the assay (FIG. 20), thus ruling out any de novo pilin expression. The extent of U(VI) removal corresponded well with the levels of piliation, which were measured as the protein content of purified PilA− containing pili samples (FIGS. 21A and 21B). The pRG5::pilA piliation (3.6±1.7 μg pili/OD600) was 2.5-fold higher than WTP+ (1.5±0.1 μg/OD600), which matched well with its superior capacity to remove U(VI) from solution (1.8±1.0-fold higher than WTP+). By contrast, WTP− and PilA− samples had no detectable pili protein and reduced less U(VI).

Figure 22:
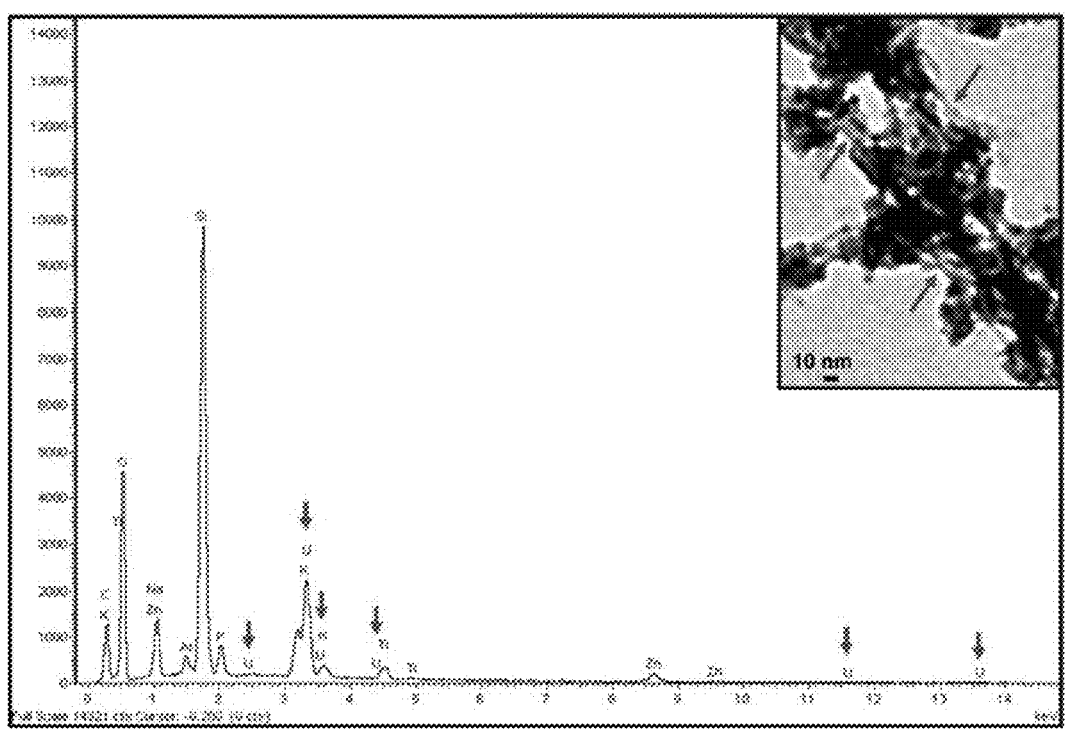
FIG. 22 shows an energy dispersive X-ray spectrum of the pili-associated electron-dense deposits imaged by TEM (inset). Uranium peaks are highlighted with arrows. Inset shows pili filaments (red arrows) interspersed with the electron-dense uranium deposits.
Figure 23:
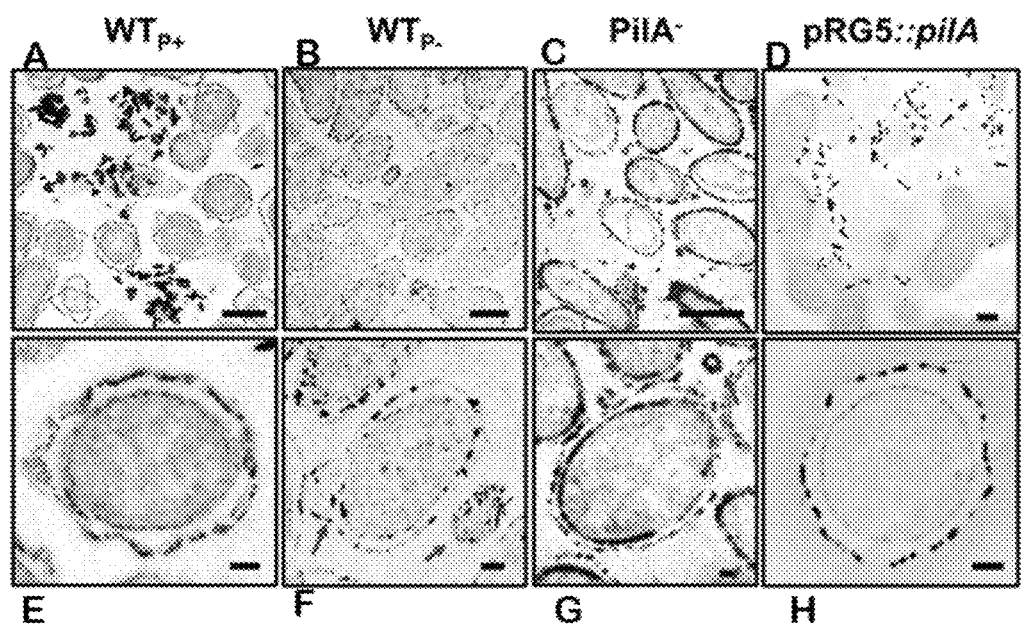
FIGS. 23A-23H are TEM images of subcellular localization of uranium deposits of thin piliated sections (WTP+ and pRG5::pilA) and non-piliated (WTP− and PilA−) cells. Top panels (FIGS. 23A-23D) show large fields (bar, 500 nm) and bottom panels (FIGS. 23E-23H) show close-ups of a representative cell (bar, 100 nm). Needle-like extracellular precipitates are noticeable in the top micrographs (FIGS. 23A-23D) of the piliated strains, which is consistent with pili-associated uranium deposits. Discreet uranium deposits on the outer membrane are also noticeable in most cells of the WTP+ and WTP− and in a few cells of the pRG5::pilA strain, while fully mineralized outer membranes and periplasmic deposition is the observed in most PilA− cells (top and bottom panels). Mineralized membrane vesicles budding from the cell (WTP−) or detached (PilA−) are indicated with red arrows.

The location of the U reductase system was studied by examining the cellular localization of the U deposits in unstained whole cells by TEM (FIGS. 19B-19E). The piliated strains, WTP+ and pRG5::pilA, preferentially deposited the U extracellularly and in a monolateral fashion, consistent with the localization of *Geobacter* conductive pili to one side of the cell. The pili filaments were interspersed with the dense deposits (FIG. 22). Elemental composition analyses of the pili-associated deposits by TEM-EDS in the WTP+ confirmed the presence of U (FIG. 22). In contrast, extracellular U mineralization in the non-piliated strains, WTP− and PilA− was limited to the cell surface and to membrane vesicles. TEM thin sections of the unstained cells confirmed the presence of extracellular, needle-like U deposits in the piliated strains as well as discreet regions of U deposition on the outer membrane (FIGS. 23A-23H). Only a few cells (8±3% of the WTP+ and <1% of the pRG5::pilA) had periplasmic mineralization.

Figure 24:
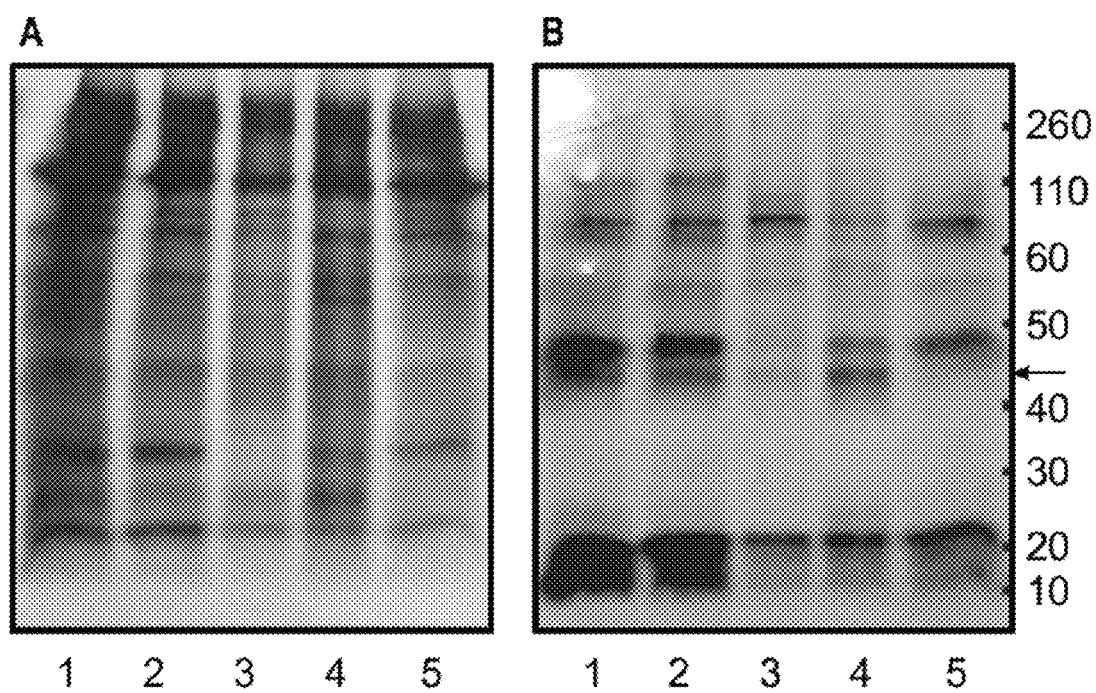
FIGS. 24A and 24B are images showing SDS-PAGE profiling of mechanically detached outer membrane proteins. Samples were resolved in 12% (wt/vol) SDS-PAGE gels and silver-stained for total protein (FIG. 24A) and for heme content (FIG. 24B). Approximately 2.5 μg of protein were loaded per lane. Lanes: 1, WTP+; 2, WTP−; 3, PilA− mutant; 4, pRG5::pilA; and 5, OmcS-mutant. Numbers at right are molecular weight standards in kDa. The migration of the OmcS c-cytochrome is marked with an arrow.

Outer membrane foci of U deposition were also noticeable in the WTP−, but more cells (37±13%) had periplasmic deposition. The increased periplasmic mineralization in the WTP− cannot be attributed to a differential expression of outer membrane c-cytochromes, as outer membrane protein fractions had the same heme profile and content as the WTP+(FIG. 24). By contrast, the PilA− mutant was partially defective in outer membrane c-cytochrome production (FIG. 24) and had the highest levels of periplasmic mineralization (85±12% of the cells) (FIGS. 23A-23H).

EXAFS Analyses Demonstrate the Reduction of U(VI) to Mononuclear U(IV)

Figure 25:
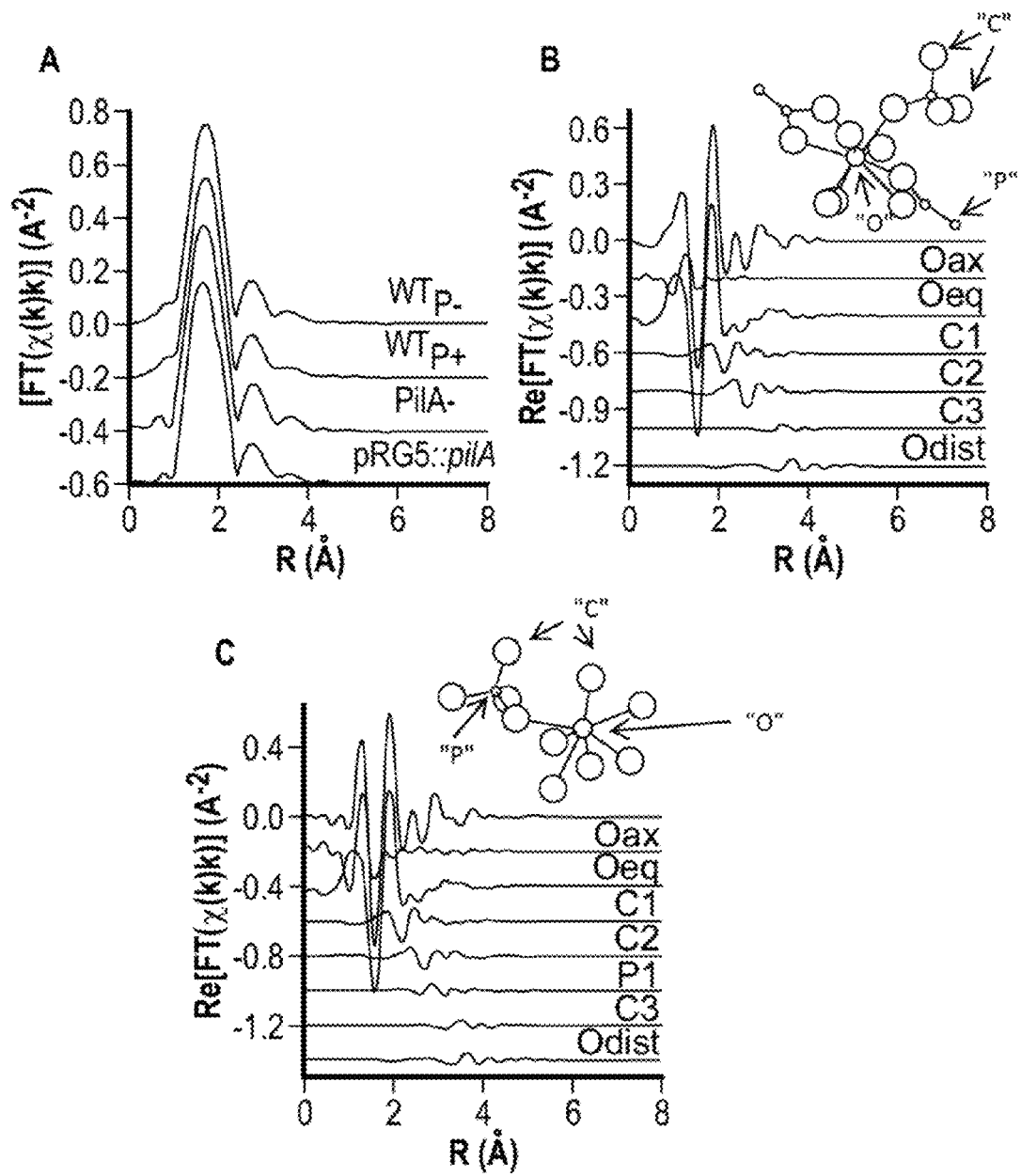
FIGS. 25A-25C show U LIII-edge Extended X-Ray Absorption Fine Structure (EXAFS) spectra (symbols) and models (line) (FIG. 25A). Magnitude of Fourier transform spectra are offset for clarity (FIGS. 25B and 25C). Real part of Fourier transform of WTP+ is shown in FIG. 25B and real part of Fourier transform of PilA− is shown in FIG. 25C. The components of the model are shown offset beneath the total model. Insets in FIGS. 25B and 25C show the U(IV) moiety that is consistent with the measured EXAFS spectra (U(IV), namely, medium-sized circles "O," large-sized circles "C" and small-sized circles "P".

U LIII-edge EXAFS spectra were modeled to determine the atomic coordination about U and characterize the U(IV) product in all the strain. Models for the EXAFS spectra included signals from neighboring P, U, and Fe atoms, but only C neighbors were found to accurately reproduce the measured spectra. The spectra were best described by a mixture of U(IV) and U(VI) coordinated by C-containing ligands. Only the PilA− mutant required an additional P ligand. A U signal corresponding to the U—U distance in uraninite at 3.87 Å was tested but was inconsistent with the measured spectra. FIG. 25A shows the magnitude of the Fourier transformed spectra and models for each spectrum.

FIGS. 25B and 25C show, as examples, the contribution of each path in the model in the real part of the Fourier transform for the WTP+ and PilA− cells and insets in each of FIGS. 25B and 25C show a molecular moiety of the U(IV) atomic environment that is consistent with the measured EXAFS. The WTP+ model includes one C ligand bound to two O atoms of U in a bidentate fashion and followed by a distant C atom (C3) and another C ligand bonded to one O atom of U(IV) in a monodentate fashion and attached to a distant O atom (Odist). This model was simultaneously refined to all spectra and was insufficient to reproduce the PilA− spectrum, which required an additional monodentate P ligand (FIG. 25C). The distances and σ2 values used to model the spectra are listed in Table 8.

TABLE 8

EXAFS modeling results for R and $\alpha^2$**

| Path | CN | R (Å) | $\alpha^2$ ($\cdot 10^{-3}$ Å$^2$) |
|---|---|---|---|
| Oax | Noax | 1.79 ± 0.01 | 2* |
| Oeq | Noeq | 2.37 ± 0.01 | 15 ± 1 |
| C1 | Nc1 | 2.94 ± 0.01 | 5 ± 2 |
| C2 | Nc2 | 3.43 ± 0.01 | 5 ± 2 |
| Oax1-Oax2 | Noax | 3.58 ± 0.01 | 4* |
| Oax1-U-Oax2 | Noax | 3.58 ± 0.01 | 4* |
| Oax1-U-Oax1 | 2Noax | 3.58 ± 0.01 | 8* |
| P1** | Np1 | 3.57 ± 0.05 | 5 ± 2 |
| C3 | Nc1 | 4.41 ± 0.02 | 5 ± 2 |
| C1-C3 | 2Nc1 | 4.41 ± 0.02 | 5 ± 2 |
| C1-C3-C1 | Nc1 | 4.41 ± 0.02 | 5 ± 2 |
| Odist | Nc2 | 4.55 ± 0.02 | 5 ± 2 |
| C2-Odist | 2Nc2 | 4.58 ± 0.02 | 5 ± 2 |
| C2-Odist-C2 | Nc2 | 4.60 ± 0.02 | 5 ± 2 |

*value held
**for the PilA− mutant data set only

The coordination numbers (Table 9) are consistent with 1 to 2 bidentate C ligands and 2 monodentate C ligands per U atom.

TABLE 9

EXAFS modeling results for coordination numbers.

| data set | Noax | Noeq | C1 | P1 | C2 |
|---|---|---|---|---|---|
| WT$_{P+}$ | 0.3 ± 0.1 | 7.6 ± 0.4 | 1.8 ± 0.3 | — | 2.5 ± 0.4 |
| WT$_{P-}$ | 0.4 ± 0.1 | 7.5 ± 0.3 | 1.7 ± 0.3 | — | 2.5 ± 0.4 |
| PilA− | 0.9 ± 0.1 | 7.1 ± 0.4 | 2.0 ± 0.3 | 0.5 ± 0.3 | 2.3 ± 0.5 |
| pRG5::pilA | 0.8 ± 0.1 | 7.1 ± 0.4 | 1.6 ± 0.3 | | 2.3 ± 0.5 |

The number of Oax atoms (Noax) was also used to estimate the amount of U(IV) in these samples, as there are two Oax atoms for each U(VI) atom and none for U(IV) (23). An average of 3-4 replicates for each strain gives the values of 72±16% (WT$_{P+}$), 81±6% (pRG5::pilA), 85±5% (WT$_{P-}$), and 76±10% (PilA−). This provides additional evidence that the extent of U(VI) removal depended on the expression of the pili.

Figure 26:
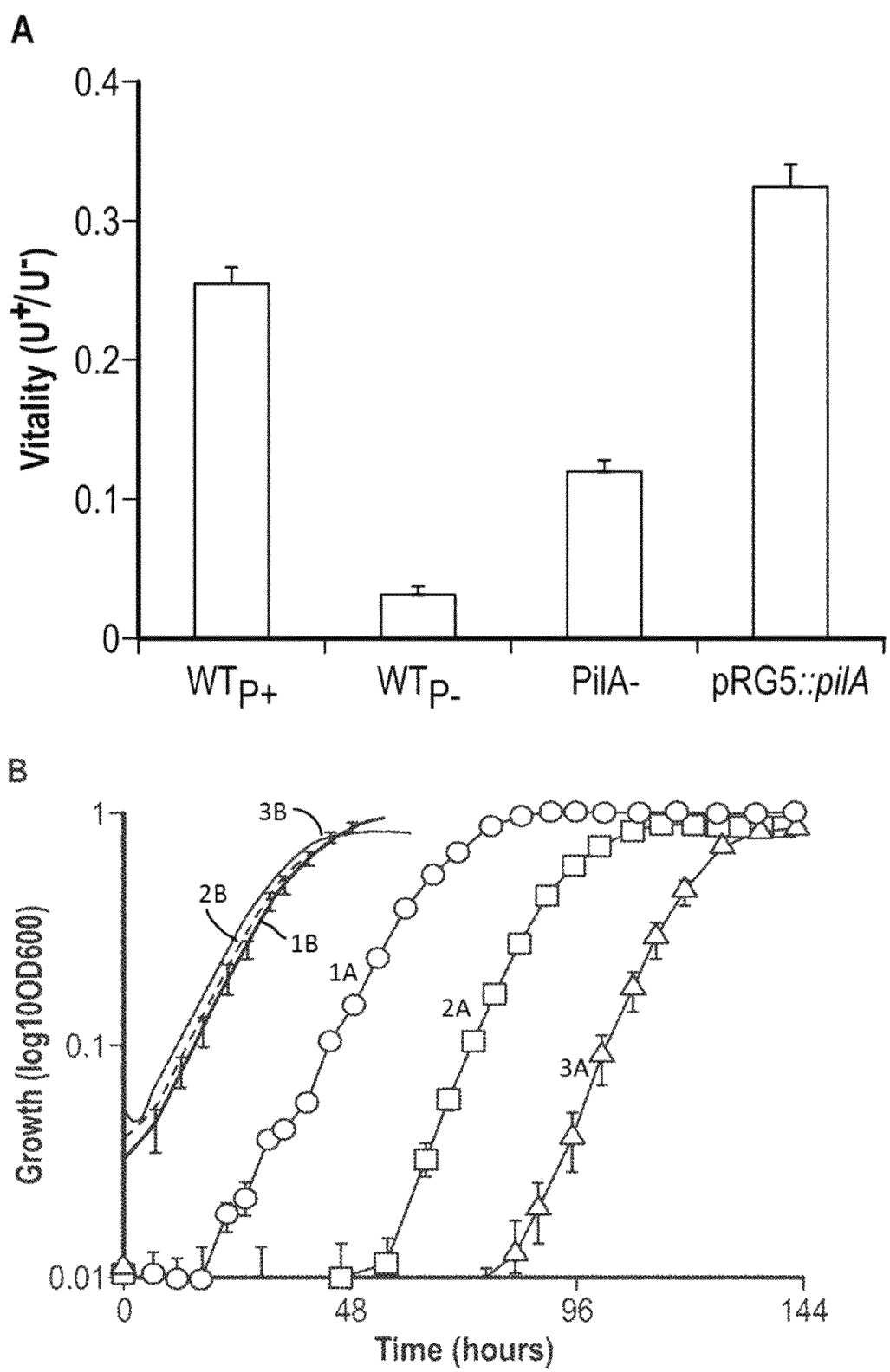
FIGS. 26A and 26B are graphs showing the effect of U(VI) exposure on cell vitality (FIG. 26A) and viability (FIG. 26B). Vitality (FIG. 26A) was measured as bacterial reductase (respiratory) activity with the RedoxSensor™ dye in resting cells of the pili-expressing (WTP+ and pRG5::pilA) and non-expressing (WTP− and PilA−) strains and expressed as the ratio of relative fluorescence units emitted by cells incubated with (U+) or without (U−) U. Growth recovery (FIG. 26B) of resting cells of the pRG5::pilA (1A—circles), WTP+(2A—squares), and WTP− (3A—triangles) after 6 h of U exposure (lines 1A, 2A and 3A) are shown in comparison to controls without U (lines 1B, 2B and 3B).

Reduction of U to mononuclear U(IV) phases. Despite differences in the mechanism and yields of U reduction, the strains with the lowest levels of periplasmic mineralization (WT$_{P+}$, pRG5::pilA and WT$_{P-}$) produced similar U L$_{III}$-edge EXAFS spectra that were modeled as mostly U(IV) coordinated by C-containing ligands in bidentate and monodentate fashion and that lacked any Fe- or P-containing ligands. The bidentate C1-C3 ligand is likely biological in nature as reported for the carboxyl coordinations involving amino acids and lipolysaccharide sugars. In contrast, the PilA− mutant, which had the highest degree of periplasmic mineralization, required an additional monodentate P ligand. This signal was small with a coordination number of 0.5±0.3, indicating that, on average, 50% of the U atoms contained a P ligand while the other 50% shared the atomic coordination of the other strains U reduction via pili as a cellular protective mechanism. The reverse correlation between piliation and periplasmic mineralization suggested that the pili-mediated reduction prevented U from permeating and being reduced in the periplasm, thus preserving vital functions of the cell envelope. To test this, we used the fluorogenic RedoxSensor™ Green dye to measure the cell's reductase activity (mostly, respiratory activity of the strains after U exposure in reference to unexposed controls. The respiratory activity or 'vitality' remaining after U exposure was higher in the piliated strains and proportional to the levels of piliation (pRG5::pilA>WTP+) (FIG. 26A). Inasmuch as the activity of the electron transport chain is a vital function of the cell, these results suggested that the pili-catalyzed reduction of U also preserved the cell's viability.

To test this hypothesis, we recovered the resting cells in growth medium and studied the cell's survival (defined as the cell's ability to maintain its integrity and undertake division) after exposure to U as a function of the length of the lag phase (FIG. 26B). While cells that had not been exposed to U recovered rapidly and simultaneously, the strains exposed to U recovered in a step-wise fashion. The lag phase was shortest (~18 h) in the hyperpiliated pRG5::pilA cells, followed by the WTP+ (~56 h) and the WTP− (~81 h), and correlated well with the levels of periplasmic mineralization of the strains (R2=0.947). The PilA− mutant recovery was similar to the other non-piliated strain, WTP−, yet more variable (lag phases ranging from 72 to 82 h). It also grew faster (~9 h doubling time compared to ~11 h for the WT and pRG5::pilA strains) than the other strains, which is expected to accelerate recovery. Despite these differences, the survival rates (calculated as the reverse of the length of the lag phase) of all the strains followed a linear regression (R2=0.908) with the levels of pili protein.

The results show that piliated cells immobilized a greater amount of U and also prevented it from permeating inside the periplasm, where it would have otherwise been reduced nonspecifically by c-cytochromes and other low potential electron donors. As a result, the extracellular reduction of U via pili also preserved the vital functions of the cell envelope and the cell's viability. When a temperature-dependent regulatory switch to produce WT controls (WTP−) was used, the WTP− did not assemble pili, yet had WT levels and profiles of outer membrane cytochromes.

The lack of pili in the WTP− strain significantly diminished the cell's ability to remove U(VI) from solution, increased the degree of periplasmic mineralization, and reduced the respiratory activity of the cell envelope and the cell's viability. WTP− cells also had extensive outer membrane vesiculation, a process linked to the selective detoxification of unwanted periplasmic materials by cells undergoing cell envelope stress. Similarly, the inability of a PilA− mutant to produce pili impaired the yields of U reduction. This mutant strain also had a reduced outer membrane cytochrome content and, as a result, more U traversed the outer membrane and precipitated in the periplasm.

Figure 27:
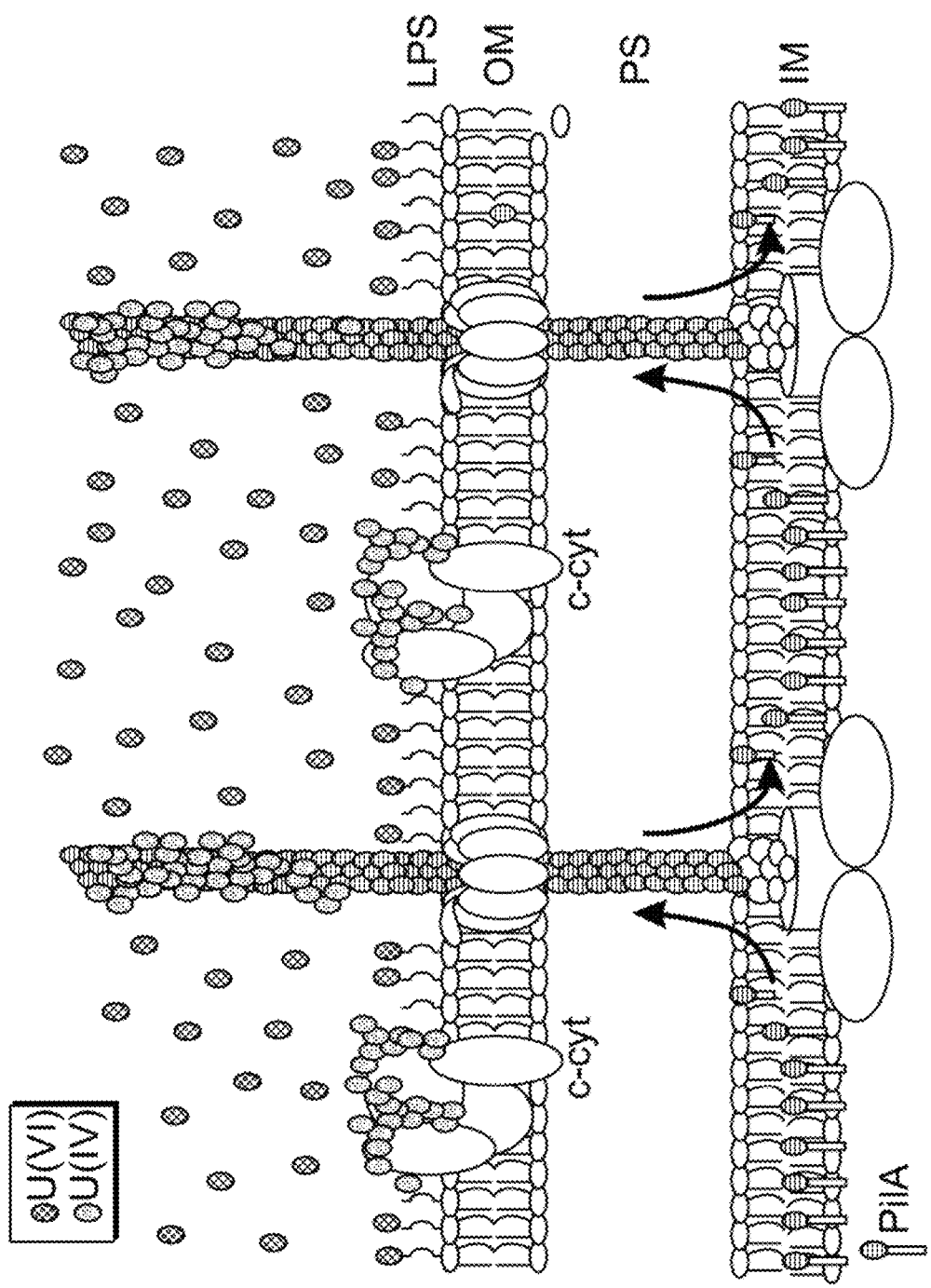
FIG. 27 is a schematic illustration of a model for the extracellular reduction of U(VI) to U(IV) with conductive pili functioning as primary uranium reductases and c-cytochrome foci (c-cyt) as secondary reduction sites. Abbreviations: inner membrane (IM), periplasmic space (PS), outer membrane (OM), lipopolysaccharide (LPS).

The correspondence observed between piliation, extent of U(VI) reduction, cell envelope respiratory activities and cell viability support a model in which the conductive pili function as the primary mechanism for U reduction and cellular protection (FIG. 27). Pili can reach several μm in length, thereby increasing the redox-active surface area available for binding and reducing U(VI) outside the cell. Although most of the U reduced by the piliated cells was extracellular and associated to the pili, discreet regions of the outer membrane also participated in the reduction of U. In *G. sulfurreducens* most of the redox activity of the outer membrane is provided by abundant c-cytochromes that decorate the cell surface as defined foci. Thus, they can provide a mechanism for reducing U in localized regions of the membrane and preventing it from permeating into the periplasm. In support of this conclusion, the PilA− mutant cells, which had reduced outer membrane cytochrome content, preferentially reduced U in the periplasm.

Example 6

Biofilms and Uranium Reduction or Removal

Strains and Culture Conditions

Wild-type (WT) *Geobacter sulfurreducens* PCA (ATCC 51573), a pilin-deficient mutant (PilA−), and its genetically complemented strain (pRG5::pilA) were routinely cultured in fresh water (FW) medium with the modifications described previously, and supplemented with 15 mM acetate and 40 mM fumarate (FWAF). The medium was dispensed into serum bottles, sparged with $N_2:CO_2$ (80:20), sealed with butyl rubber stoppers (Bellco) and aluminum tear-off seals (Wheaton), and autoclaved 30 minutes. Biofilms were grown on 6-well cell-culture-treated plates (Corning), or glass coverslips (Corning). Prior to inoculation the glass coverslips were acid-washed overnight with a 50/50 (vol/vol) $HCl/NO_3^-$ mixture or a 15% (vol/vol) $HCl/H_2O$ mixture, rinsed thoroughly with dd$H_2O$, and inserted into sliced rubber stoppers (4 coverslips/stopper), as previously described (36). Immediately prior to inoculation, the stopper-coverslip assembly was autoclaved in FW medium lacking vitamins, minerals, acetate, and fumarate. Each stopper-coverslip assembly was placed in a sterile 50 ml conical tube (Corning). Biofilm assays were inoculated with an early stationary-phase FWAF culture to a final $OD_{600}$ of 0.04, grown anaerobically inside a vinyl glove bag (Coy Labs) with a $H_2:CO_2:N_2$ (7:10:83) atmosphere, and incubated at 30° C. for 24, 48, or 72 h, as specified.

Biofilm Protein Determination

For determination of the total protein content of the biofilms, biofilms were grown for 24, 48 or 72 h in 6-well plates, scraped off, and harvested by centrifugation (5 min, 12,000×g). The resulting cell pellet was boiled for 1 h in 2M NaOH, allowed to cool, and then neutralized with an equal volume of 2M HCl. The sample was centrifuged to remove cellular debris, and the resulting supernatant analyzed for total protein content. Protein was quantified using a Pierce Microplate BCA Protein Assay Kit (reducing reagent compatible, Thermo Scientific) with BSA standards, according to the manufacturer's specifications. Protein was measured as an $OD_{562}$ on a Tecan Sunrise Plate Reader (Tecan, Inc.).

U(VI) Resting Cell Suspension and Biofilm Assays

The ability of cells to remove U(VI), provided as uranyl acetate, from solution was assayed in resting planktonic and biofilm cell suspensions using protocols adapted from those described previously. Heat-killed and uninoculated controls were also included to rule out any abiotic removal activity or absorption. Resting biofilm suspensions were prepared from biofilms grown on stopper-coverslip assemblies for 24, 48, or 72 h, as described above. The culture broth was decanted, the assembly rinsed gently with sterile, anaerobically-prepared wash buffer, and 20 ml of reaction buffer supplemented with 20 mM sodium acetate and 1 mM uranyl acetate (Electron Microscopy Sciences) prepared in 30 mM bicarbonate buffer was added. Resting planktonic and biofilm cell suspensions were incubated for 24 h at 30° C. Following incubation, 500 μl samples of the supernatant were removed, filtered (0.22 μm Millex-GS filter, Millipore), acidified in 2% nitric acid (500 μL), and stored at −20° C. For kinetic studies of U(VI) removal, samples were taken every 6 h. All procedures were performed inside an anaerobic glove bag, as described above. The concentration of U(VI) in the acidified samples was measured using a Platform Inductively Coupled Plasma Mass Spectrometer (ICP-MS) (Micromass, Thermo Scientific) or a Kinetic Phosphorescence Analyzer (KPA) (Chemchek).

Vitality Fluorescent Assays

The respiratory activity of biofilm cells after exposure to uranium was assayed using the fluorescent RedoxSensor™ vitality kit (Life Technologies Corp.), as previously described. WT biofilms were grown on coverslips for 48 h and incubated in reaction buffer with 1 mM, 2.5 mM and 5 mM concentrations of uranyl acetate. Control biofilms incubated in reaction buffer without uranyl acetate were also included. After 24 h of incubation, the reaction buffer was decanted from the tubes and the stopper-coverslip assemblies were washed with wash buffer. The biofilms were then scraped from the assembly and resuspended in 1 ml reaction buffer. Samples were vortexed briefly, mixed 1:1 with Redox dye solution, and incubated 10 min before measuring fluorescence (490 nm excitation, 520 nm emission) on a SpectraMax M5 plate reader (Molecular Devices). The respiratory activity of the biofilms was calculated as the fluorescence emission of the Redox Sensor dye relative to the metabolic activity of controls without uranium. Separate aliquots of the samples were stained with SYTO 9 (Life Technologies Corp.) to confirm that the samples had the same amount of cells.

Microscopy

Biofilm growth on 6-well plates was examined by Confocal Laser Scanning Microscopy (CLSM). Following the specified incubation period, planktonic growth was carefully removed and the remaining biofilm was stained with LIVE/DEAD BacLight Bacterial Viability Kit (Life Technologies Corp.) dye solution, following the manufacturer's recommendations. The biofilms were stained for approximately 15 min, washed once in PBS, and imaged on a Zeiss Pascal LSM microscope (Carl Zeiss Microscopy, LLC) equipped with an Achroplan 40x/0,80W dipping objective. COMSTAT analyses were carried out using images from three biological replicates, with 6-10 distinct fields-of-view (1,024×1,024 pixels, 0.22 μm/pixel) for each. Images were collected every 1.14 μm, and projections were created using Zeiss LSM Image Browser software (Carl Zeiss Microscopy, LLC). The structure of the biofilms was characterized using COMSTAT image analysis software using connected volume filtration to remove noise in the data, as described previously.

When indicated, the biofilms were also examined with a Scanning Electron Microscope (SEM). Biofilms were grown for 48 h on round glass coverslips (12-mm diameter), and exposed to 1 mM uranyl acetate for 24 h. The biofilms were then fixed at 4° C. for 1-2 h in 4% glutaraldehyde, rinsed briefly in 0.1M sodium phosphate buffer, and dehydrated in a series of ethanol washes (25%, 50%, 75%, 95%, 10 minutes each), followed by three 10 min washes in 100% ethanol. The samples were critical-point dried using a Blazers 010 critical point dryer (Blazers Union Ltd.) with liquid $CO_2$ as the transitional fluid. Once dry, the coverslips containing the biofilm samples were mounted on aluminum stubs using epoxy glue and coated with ~10 nm of osmium using a NEOC-AT osmium coater (Meiwafosis Co., Ltd.). Samples were examined with a JEOL JSM-7500F SEM equipped with an Energy Dispersive Spectroscopy (EDS) 30 $mm^2$ detector crystal for elemental analyses.

X-ray Absorption Spectroscopy (XAS)

The valence and speciation of U in the biofilms was estimated by XANES (X-ray Absorption Near Edge Spectroscopy) and EXAFS (Extended X-ray Absorption Fine Structure Analysis), respectively. For these analyses, biofilms were grown on stopper-coverslip assemblies, and exposed to U for 24 h, as described above. After rinsing the assemblies gently with wash buffer, the biofilm biomass was scraped off the assemblies using and resuspended in 2 ml of reaction buffer. The cells were then harvested by centrifugation (12,000×g, 10 min), loaded into custom-made plastic holders, and stored at −80° C. All procedures were carried out in an anaerobic chamber, and samples were kept frozen during XAS measurements. XANES and EXAFS measurements were performed using standard beamline parameters and a multielement Ge detector in fluorescence mode using the PNC-CAT beamline 20-BM at the Advanced Photon Source (Argonne National Laboratory). Data obtained from XANES and EXAFS analysis was processed according to the combination of protocols described previously.

SDS-PAGE and Protein Staining

The exopolysaccharide matrix (EPS) was extracted from biofilms grown 48 h on 6-well plates using a modification of a protocol described previously (8, 38). Briefly, biofilms were scraped and collected in reaction buffer. The solution was centrifuged for 10 minutes at 13,000×g and the resulting pellet was resuspended in ⅕ volume of THE and vortexed for 1 min. SDS was added to a final concentration of 0.1%, and the solution was mixed at room temperature for 5 min. The samples were then passed 10 times through an 18G needle, and centrifuged at 15,500×g to collect the sheared materials as an insoluble fraction. The resulting pellet was washed 5 times before resuspending it in 10 mM Tris-HCl, pH 7.5.

To identify heme-containing proteins in the EPS matrix, 20 μg of protein from each EPS isolation was boiled for 10 min and separated on a 12% Mini-Protean TGX gel (Bio-Rad) at 250V for 30 min. The Novex Sharp™ markers (Life Technologies Corp.) were used a molecular weight standard. Heme-containing proteins were visualized on the gel with N,N,N',N'-tetramethylbenzidine staining, as described previously (10, 41). A duplicate gel was run in parallel and stained for total protein using Coomassie Brilliant Blue G-250 (BioRad) according to the manufacturer's recommendations.

Enhanced U(VI) Immobilization and Tolerance by Biofilms

Figure 28:
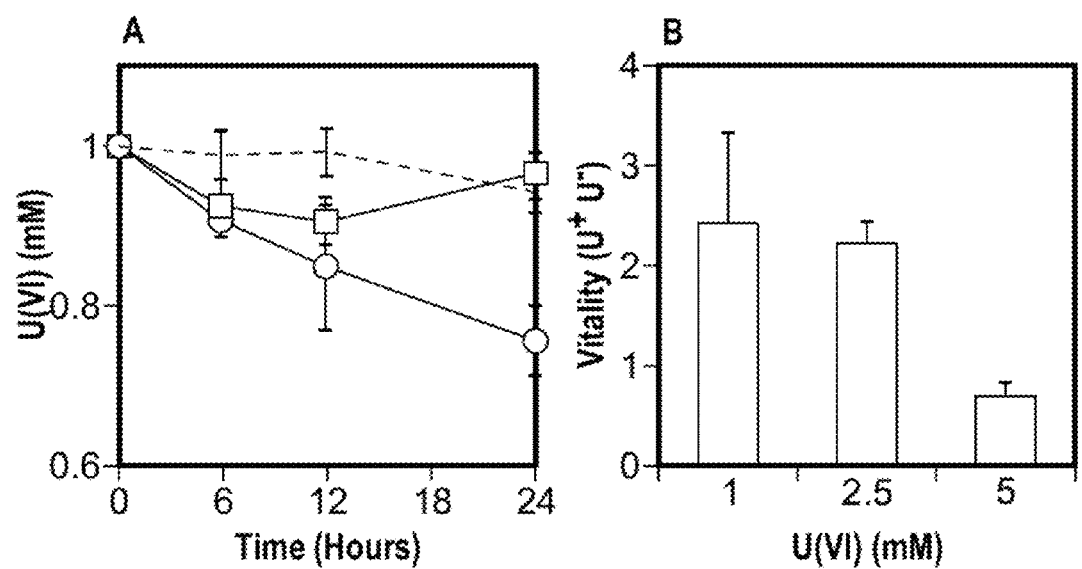
FIGS. 28A and 28B are graphs which show that biofilms maintain vital activities through 24 h of U exposure. The FIG. 28A graph shows removal of U(VI) from solution by 48 h biofilms of $G.$ $sulfurreducens$ (solid symbols) showing the linearity of the reaction for 24 hours. Controls with planktonic cells (open symbols) and uninoculated biofilm assemblies (dashed line) are also shown. The FIG. 28B graph shows the effect of 24 h exposure to increasing concentrations of U(VI) (1, 2.5, and 5 mM) on the respiratory activity of 48-h biofilms (vitality measured with the RedoxSensor™ dye and expressed as the ratio of relative fluorescence units emitted by cells incubated with (C) and without (U−) U).

The kinetics of U(VI) immobilization were investigated in resting 48 h biofilms in reference to planktonic cells (FIG. 28A).

The rates of U removal during the first 6-12 h were similar in planktonic cells and biofilms. However, while the biofilms immobilized U linearly for up to 24 h, the removal activities of the planktonic cells stopped after 12 h and the cell-associated U was solubilized again. As a result, the biofilms immobilized twice more U than the planktonic cells. Cell viability, which is crucial for assessing the capacity for U(VI) reduction, can only be preserved in planktonic cells for the first 7 h under the conditions used in this assay. After this time, osmotic pressure causes the cells to lyse and the viability of the resting cells declines rapidly. The sustained removal of U by the biofilms suggests that the biofilms remain viable and metabolically active even after prolonged exposure to the contaminant. To investigate this, we used the fluorogenic RedoxSensor™ Green dye to measure the respiratory activities of biofilm cells exposed to U for 24 h (U+) in reference to unexposed biofilm controls (U−) (FIG. 28B). The dye yields green fluorescence when modified by the bacterial reductases, which are mostly located in the electron transport system of the cell envelope. As respiration is a vital activity of the cell, the dye also measures the cell's vitality and serves as a proxy for the cell's viability. As shown in FIG. 28B, the respiratory activities of biofilm cells exposed to 1 mM U for 24 h were 2.4-fold higher than control biofilms incubated under identical conditions but without U. Furthermore, similar increases in respiratory activities were measured in biofilms exposed to 2.5 mM concentrations of U for 24 h and decreases in respiratory activity (ca. 70%) were only measured after exposing the biofilms to 5 mM concentrations of U for the same period of time. Thus, the results are consistent with increased respiratory activities and cell viability in cells within biofilms.

Extracellular Reduction of U by Biofilms

Figure 29:
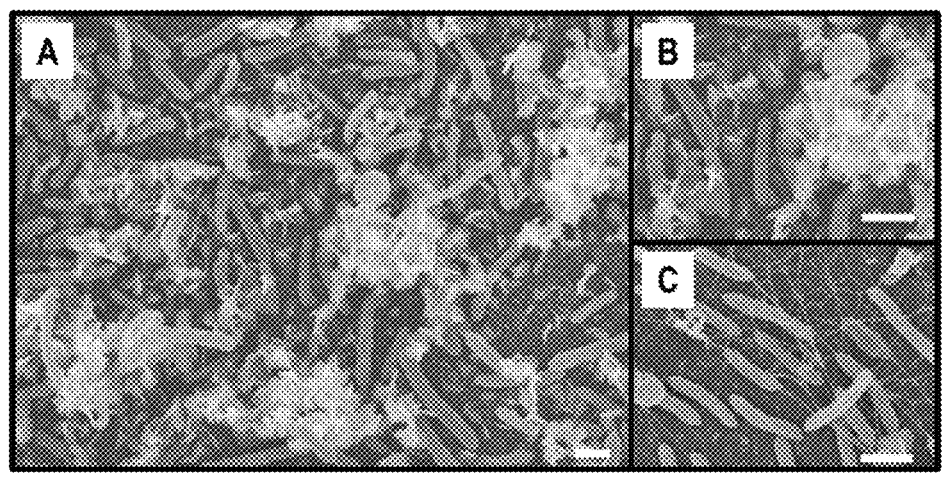
FIGS. 29A-29C are SEM micrographs of 48 h biofilms exposed to U for 24 h (FIGS. 29A and 29B) showing the extracellular needle-like, white precipitates of uranium associated with the biofilm microcolonies. Control biofilms not exposed to U are also shown (FIG. 29C). Scale bar, 1 µm.
Figure 32:
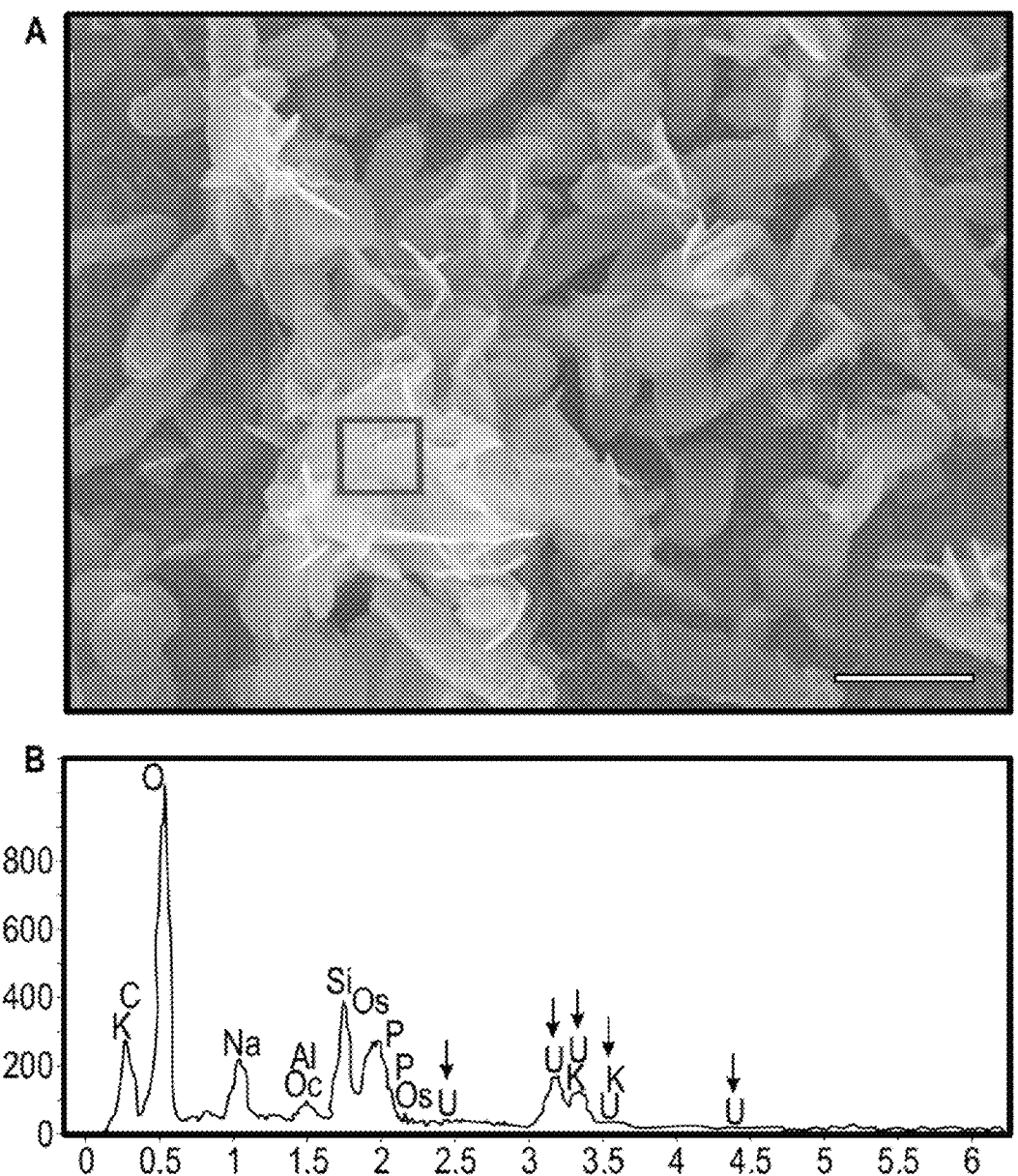
FIGS. 32A and 32B are a SEM micrograph (FIG. 32A) and EDS analysis of U precipitates (FIG. 32B), with FIG. 32A showing 48-h biofilms exposed to U for 24-h, with the area of EDS analysis indicated by the red box, and FIG. 32B showing EDS spectrum of the white precipitates within the boxed region, with U peaks indicated by arrows. Scale bar, 1 µm.
Figure 33:
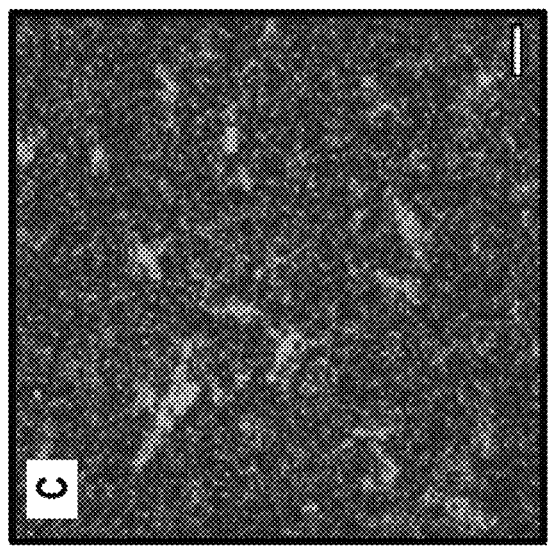
FIGS. 33A-33E are black and white CLSM micrographs showing top view projections of 24-, 48-, and 72-h WT (FIGS. 33A-33C), 48-h HA− (FIG. 33D), and 48-h pRG5::pilA (FIG. 33E) biofilms stained with the fluorescent BacLight™ viability kit. Scale bar, 20 µm.
Figure 33:
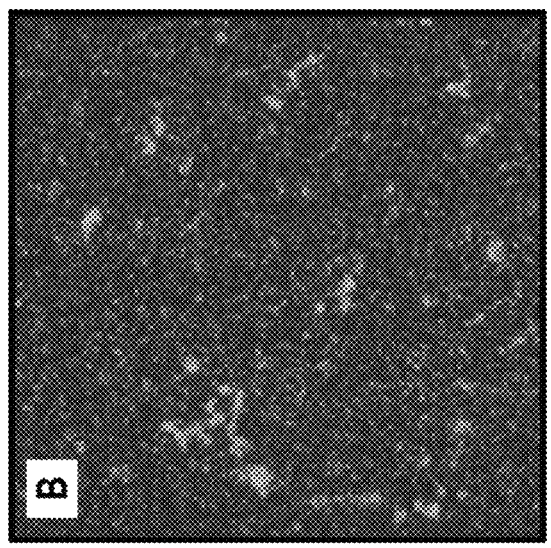
Figure 33:
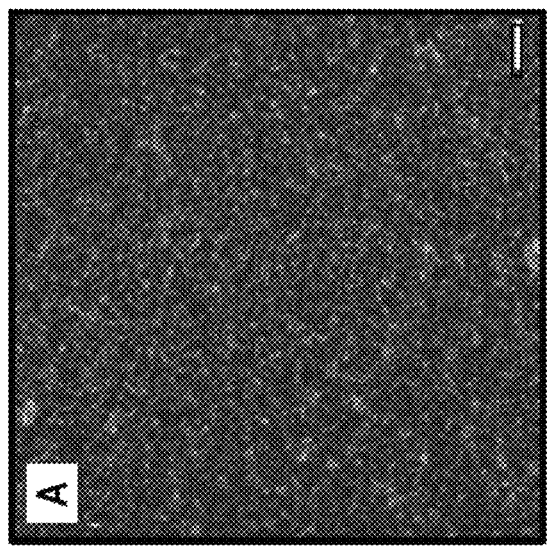
Figure 33:
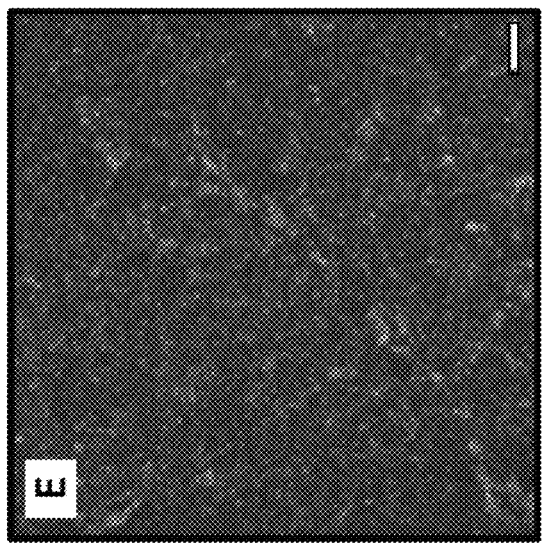
Figure 33:
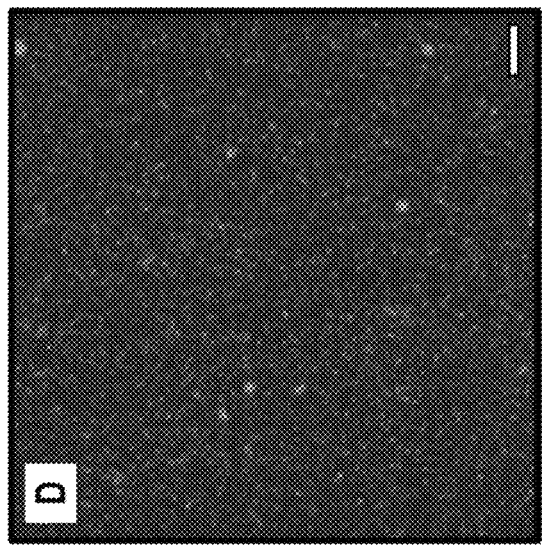
Figure 34:
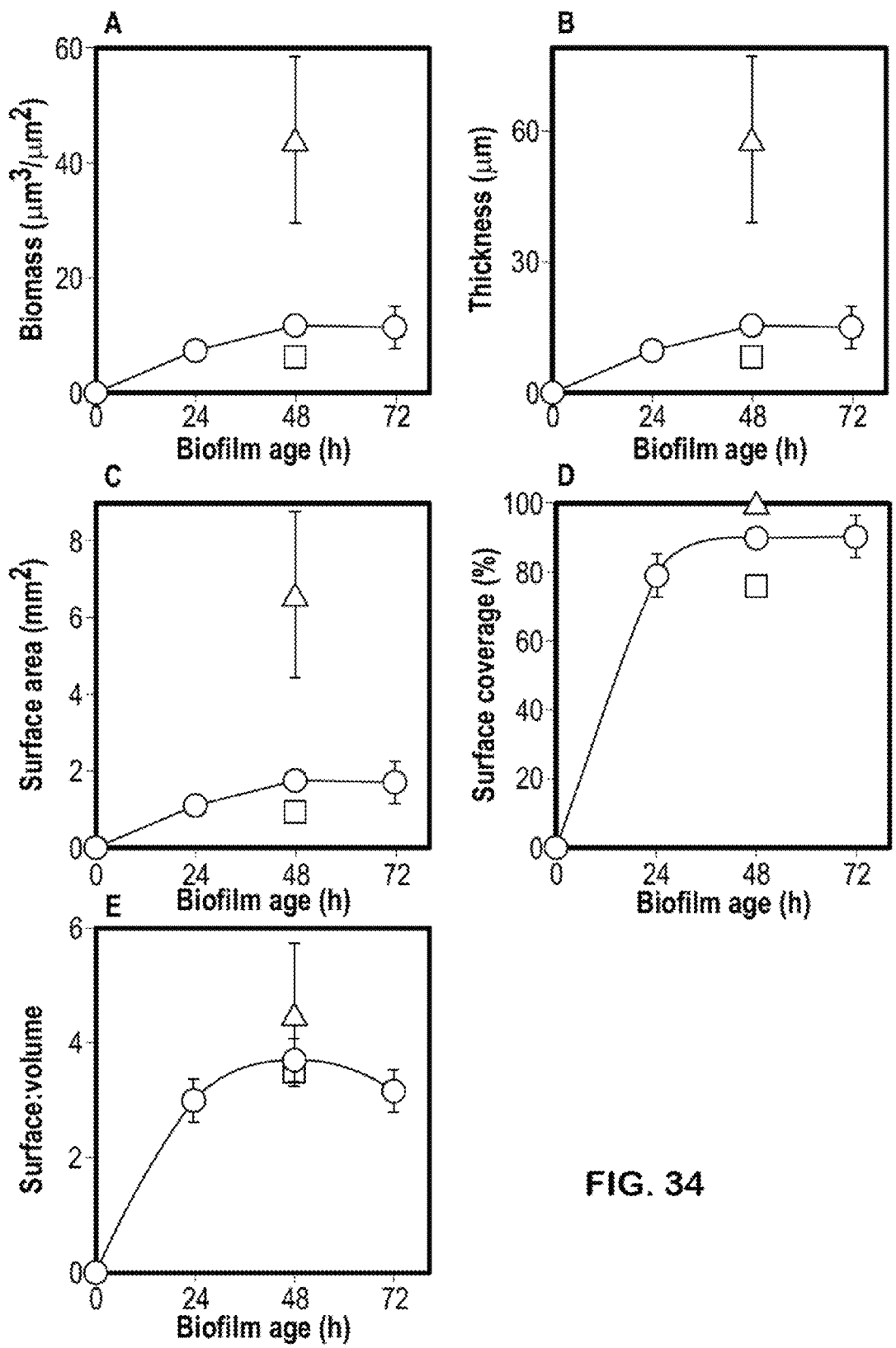
FIGS. 34A-34E are graphs showing correlation of biofilm age and biofilm biomass (FIG. 34A), thickness (FIG. 34B), surface area (FIG. 34C), surface coverage (FIG. 34D), and surface:volume ratio (FIG. 34E). Values were determined using COMSTAT analysis software (17). WT (circles), PilA− (squares), and pRG5::pilA (triangles) strains are shown.

Approximately 67% (±4%) of the U(VI) immobilized by 48 h biofilms after 24 h was reduced to U(IV). Thus, the immobilization of U(VI) by the biofilms was coupled to its reduction of U(IV). Examination of the biofilms after exposure to 1 mM U for 24 h by SEM showed needle-like, extracellular precipitates that coated the biofilm microcolonies (FIG. 29A), which elemental analyses with an EDS detector confirmed to be composed of U (FIG. 32).

At higher magnification (FIGS. 29B and 29C) the U precipitates were observed as interspersed with extracellular filaments, some with diameters (ca. 4 nm) matching well the diameters reported for the conductive pili of *G. sulfurreducens* and some with larger diameters (ca. 15-20 nm) consistent with dehydrated EPS fibers. As the biofilms grow and mature, more conductive pili and more EPS matrix with c-cytochromes are available to participate in the redox reactions of the biofilms. Hence, the ability of biofilms grown for 24, 48 and 72 h to immobilize and reduce U(VI) after 24 h of exposure to the contaminant were studied (FIG. 30A).

Figure 30:
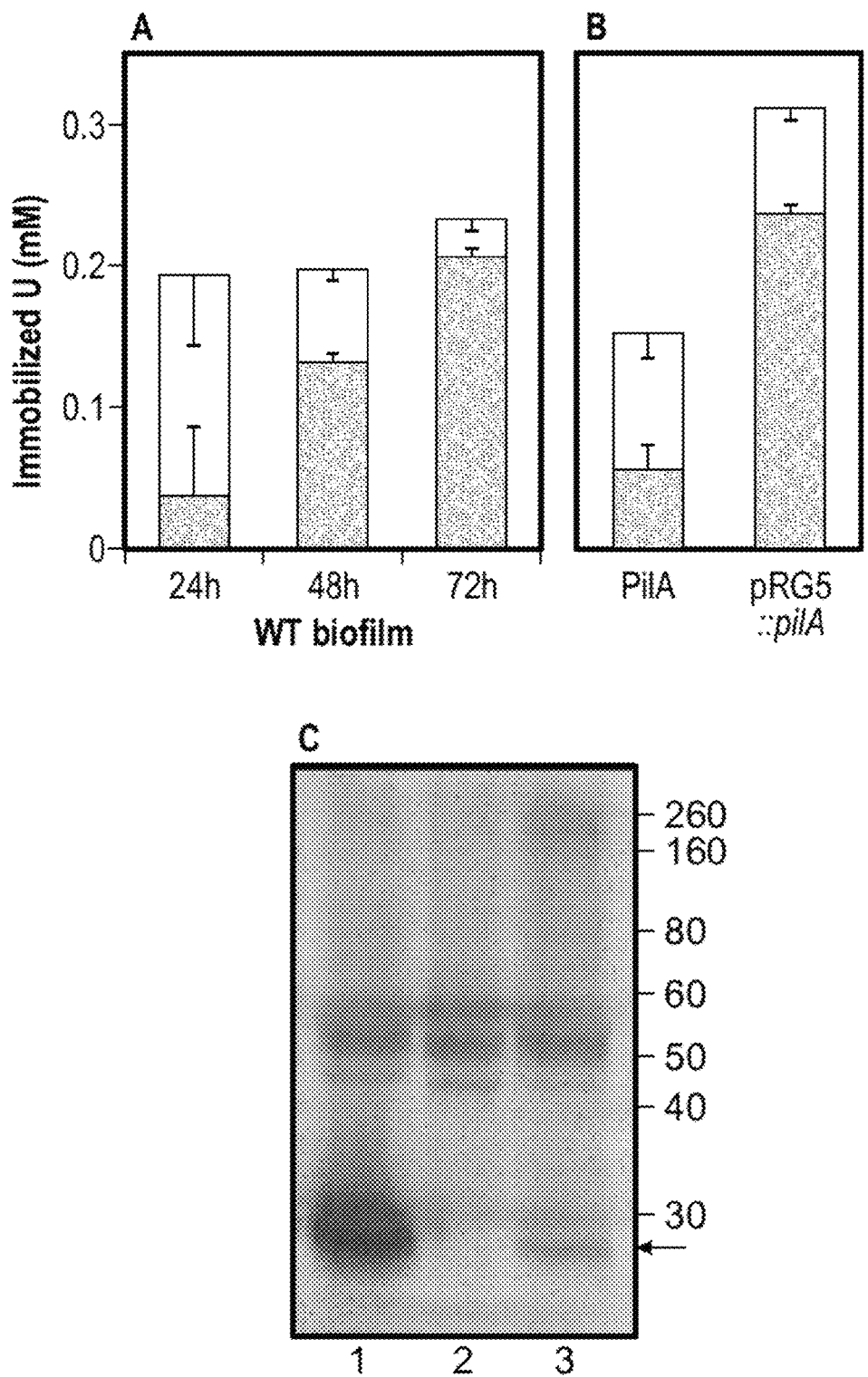
FIGS. 30A-30C show U(VI) immobilization/reduction and a cytochrome profile of the WT, PilA−, and pRG5::pilA strains, with bar graphs in FIGS. 30A and 30B showing reduction of U(VI) (open blocks) to U(IV) (solid blocks) by WT biofilms grown for 24, 48 and 72 h (FIG. 30A) and by 48 h biofilms of the pilin-deficient PilA− mutant and the hyperpiliated pRG5::pilA strain (FIG. 30B)
Figure 31:
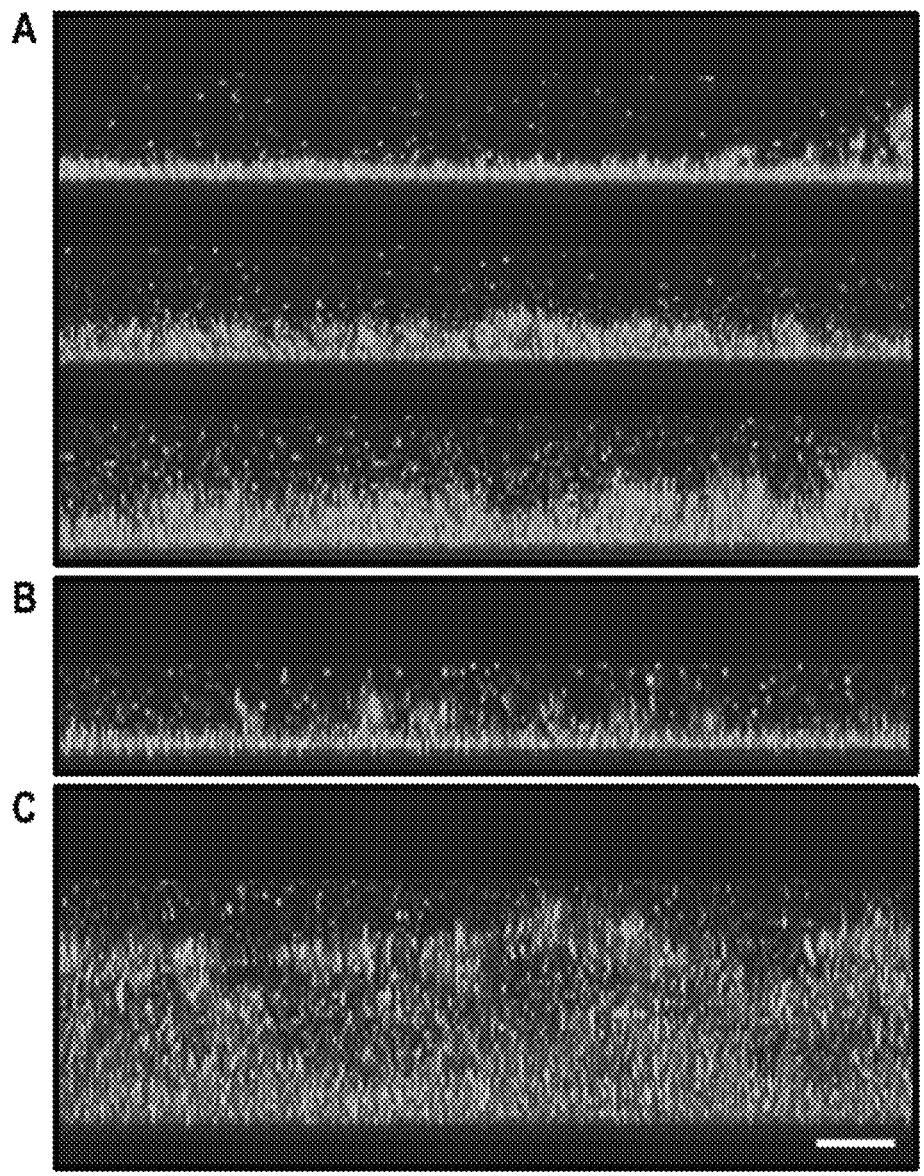
FIGS. 31A-31C are black and white CLSM micrographs showing side view projections of WT (24, 48 and 72 h) (FIG. 31A), PilA− (48 h) (FIG. 31B), and pRG5::pilA (48-h) biofilms stained with the fluorescent BacLight™ viability kit (FIG. 31C). Scale bar, 20 µm. The top view projections corresponding to these images are shown in FIGS. 33A-33E.

While the removal activities of the biofilms were similar, U reduction increased proportionally to the biofilm age and was highest in the 72 h biofilms (FIG. 30A). CLSM micrographs of the biofilms revealed visual differences in biofilm thickness and structure in 24, 48, and 72 h biofilms (FIG. 31A and FIGS. 33A-33E).

Biofilm parameters calculated using the COMSTAT analysis software such as biomass, thickness and surface area, increased linearly during the first 48 h of biofilm growth and remained unchanged in 72 h biofilms (FIG.

30A). The surface coverage and surface to volume ratio values did not change substantially as the biofilms aged (FIGS. 34A-34E, Table 10).

TABLE 10

COMSTAT analysis.

| Biofilm | Total biomass ($\mu^3/\mu m^2$) | Average Thickness ($\mu m$) | Surface Area ($mm^2$) | Surface Coverage (%) | Surface to volume ratio ($\mu m^2/\mu m^3$) |
|---|---|---|---|---|---|
| WT 24 h | 6.4 ± 1.0 | 7.8 ± 1.1 | 0.6 ± 0.1 | 80.7 ± 5.2 | 2.9 ± 0.3 |
| WT 48 h | 10.6 ± 1.3 | 13.3 ± 1.8 | 1.2 ± 0.1 | 91.8 ± 1.7 | 3.6 ± 0.4 |
| WT 72 h | 10.6 ± 3.3 | 13.9 ± 3.9 | 1.0 ± 0.2 | 92.2 ± 6.6 | 3.1 ± 0.4 |
| PilA⁻ 48 h | 5.2 ± 0.7 | 6.8 ± 1.0 | 0.6 ± 0.1 | 77.8 ± 3.6 | 3.4 ± 0.3 |
| pRG5::pilA 48 h | 43.4 ± 14.8 | 60.1 ± 18.9 | 6.1 ± 2.5 | 99.5 ± 0.5 | 1.2 ± 0.7 |

Figure 35:
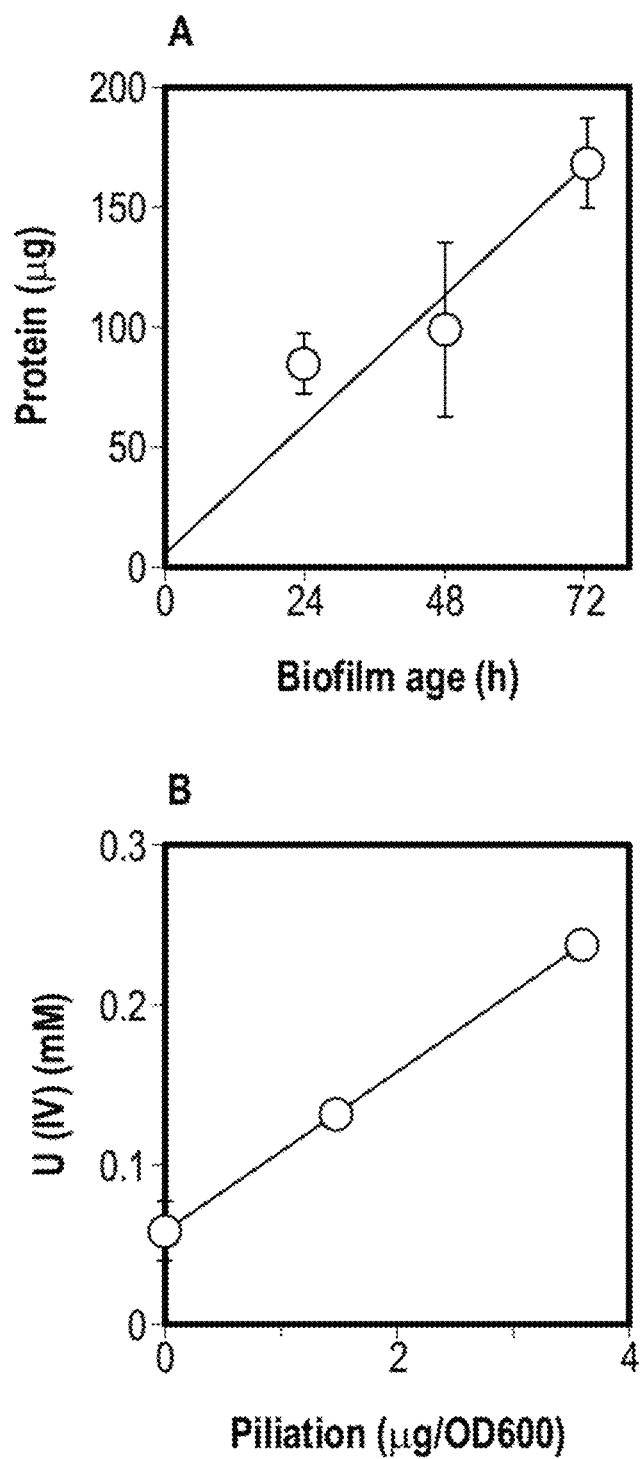
FIGS. 35A and 35B are graphs showing linear correlation between total protein content of biofilms and biofilm age ($R^2$=0.94) (FIG. 35A) and between piliation (planktonic cells grown under pili-inducing conditions at 25° C.) and U reduction by 48 h biofilms of the WT, PilA− and pRG5:: pilA strains ($R^2$=0.999) (FIG. 35B).

Consistent with this, we measured linear increases in the total protein content of the biofilms, which includes the protein from the cells and from the biofilm matrix (FIG. 35), that cannot be accounted for by increases in cell numbers calculated as biomass in the COMSTAT analyses (FIGS. 34A-34E). This supports the notion that there are specific redox-active components expressed during biofilm formation that catalyze the reduction of U.

Role of conductive pili and c-cytochromes of the biofilm matrix in U reduction. The role of the biofilm pili in U reduction was studied for the ability of 48 h biofilms of a pilin-deficient (PilA−) mutant to immobilize and reduce U compared to its genetically complemented strain pRG5::pilA (FIG. 30B). The mutant carries a deletion in the gene encoding the pilin subunit, which reduces the ability of planktonic cells to reduce U extracellularly. The mutant biofilms attached and grew on the surface but had fewer microcolonies (FIG. 31B and FIGS. 33A-33E). By contrast, it's genetically complemented strain, pRG5::pilA, which is hyperpiliated, formed very thick biofilms after only 48 h of incubation (FIG. 17 and FIGS. 33A-33E). In general, all the biofilm parameters measured in the mutant biofilms (such as biomass, thickness, surface coverage, and the like.) were similar to those measured in 24 h biofilms of the WT strain (FIGS. 34A-E), consistent with the previously reported role of Geobacter pili in microcolony formation. The mutant biofilms also removed and reduced less U than 48 h WT biofilms (FIG. 30B). By contrast, the hyperpiliation of the strain pRG5::pilA promoted biofilm formation (FIG. 31D and FIGS. 33A-E) and resulted in substantial increases in biofilm biomass, thickness and surface area but similar values for surface coverage and surface:volume ratio (FIGS. 34A-34E). The hyperpiliated biofilms also removed 1.6 times more U than the WT biofilms and reduced 76% (±3%) of U(VI) to U(IV) (FIG. 30B).

When compared to 48 h WT biofilms, the U removal and reduction activities of the PilA− and pRG5::pilA biofilms correlated strongly with the biofilm biomass and average thickness (R2=0.99), but required a logarithmic fit. This indicates that a biofilm's ability to adsorb or reduce U based solely on its biomass characteristics is finite. Hence, increases in biofilm biomass cannot solely account for the differences in U removal and reduction observed in the biofilms formed by strains with different levels of piliation. We observed a positive linear correlation between surface coverage and U removal (R2=0.82) and reduction (R2=0.92), and an inverse linear relationship between roughness and U removal (R2=0.91) and reduction (R2=0.98). Surface coverage represents the amount of cells attached to the substratum, or biofilm confluence. The roughness coefficient is a measurement of the variations in biofilm thickness. Thus, a lower roughness coefficient indicates a more uniform biofilm and a higher coefficient a more variable one. Taken together these results demonstrate that the thickness/biomass of a biofilm can be used as an initial prediction of the amount of U that can be immobilized and reduced, but the ultimate determination of the U transformation phenotype is made by structural characteristics determined by specific biofilm components, such as the pilus nanowires.

As the PilA− mutant also has defects in outer membrane c-cytochromes required for metal reduction such as OmcS and these cytochromes are anchored in the biofilm EPS matrix, we examined the heme-containing proteins associated to the biofilm matrix of the WT, PilA− and pRG5::pilA biofilms (FIG. 30C). A band with a relative molecular weight similar to that of OmcS (~47 KDa) was present in both the WT and the PilA− mutant matrices. The only heme-containing band present in the WT matrix and absent in the PilA− matrix was one with a relative molecular weight of 30 KDa. This size matches that of OmcZS, a processed isoform of the OmcZ cytochrome of G. sulfurreducens that is required for optimal current production by anode biofilms in microbial fuel cells. In vitro studies show that the purified OmcZS protein can reduce U. Thus, OmcZS could contribute to the reduction of U in the biofilms as well. The pRG5::pilA heme-stain profile also shows defects in OmcZS levels (FIG. 30C), yet produces more conductive pili and reduces more U than the WT biofilms (FIG. 30B). Furthermore, we observed a strong linear correlation (R2=0.999) between the levels of piliation of the three strains grown under pili-inducing conditions (25° C.) and the extent of U reduction by the biofilms (FIG. 35B). Hence, the results support the notion that the conductive pili are the primary U reductase of the biofilms.

XAS analyses. U L3-edge EXAFS spectra from WT and PilA− biofilms were modeled to determine the atomic coordination about U. The spectra were best described by a mixture of U(IV) and U(VI) coordinated by carbon atoms. The magnitude of the Fourier transformed spectra and models are shown in FIG. 36A, with the spectra offset for clarity.

Figure 36A:
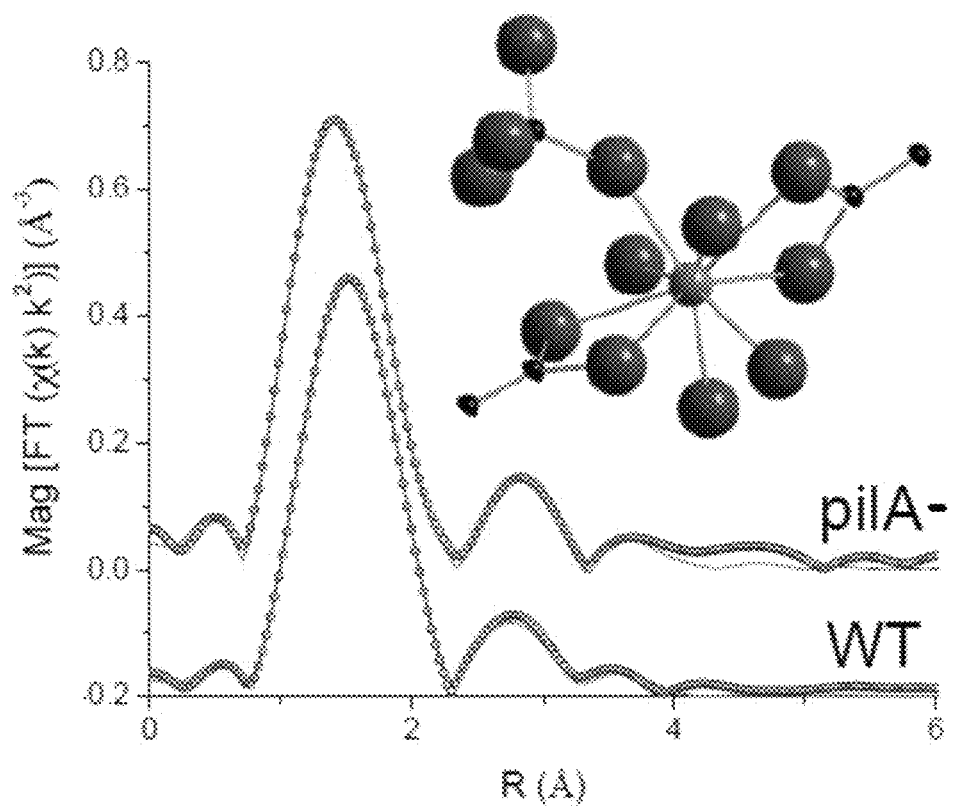
FIGS. 36A-36C are U L$_3$-edge XAFS spectra of 48 hr WT and PilA− biofilms.
Figure 36B:
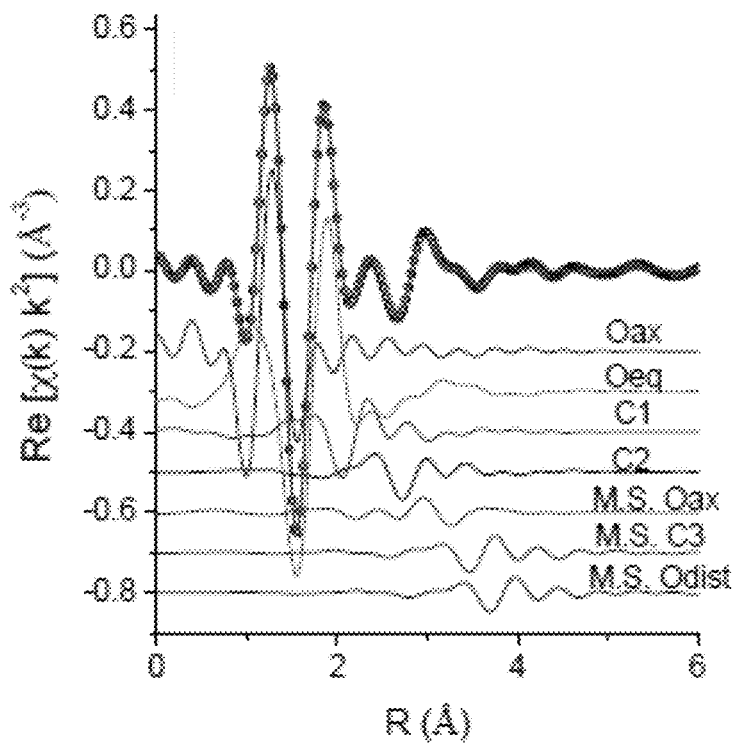
Figure 36C:
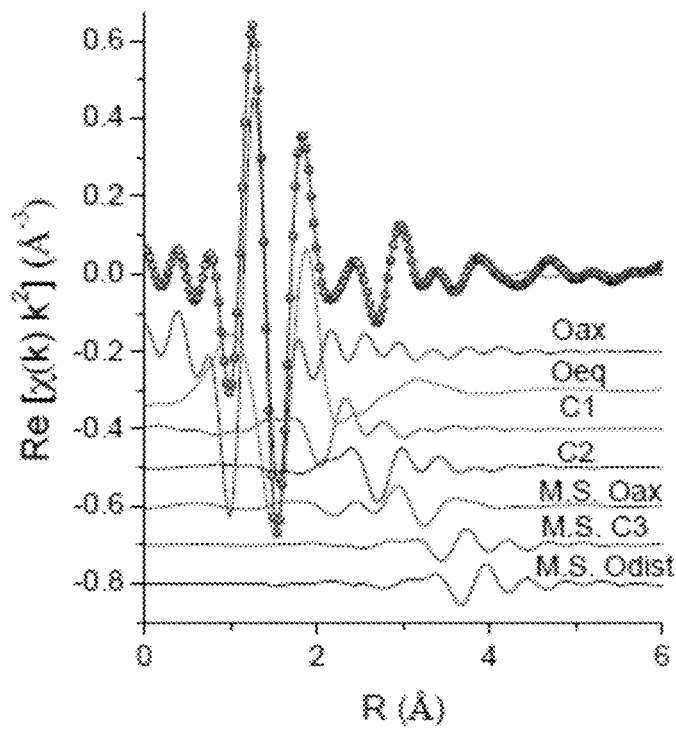

A molecular moiety that is consistent with both the WT and PilA− model is shown in the inset of FIG. 36A. FIGS. 36B and 36C show the contribution of each path in the model in the real part of the Fourier transform for the WT and PilA− samples, respectively. The model includes two types of carbon ligands. One of the C-ligands is bound to two oxygen atoms of U in a bidentate fashion and is followed by a distant carbon (C3) atom. The other C-ligand is bound to one oxygen atom of U in a monodentate fashion and is attached to a distant oxygen (Odist) atom. Multiple scattering paths from distant C3 and Odist atoms were included in the model. This model was simultaneously refined to both spectra. The distances and σ2 values used to model the spectra are listed in Table 11. Table 12 lists the coordination numbers. The coordination numbers are consistent with 1 to 2 bidentate C-ligands and 1 to 2 monodentate C-ligands per U atom. The number of Oax atoms can be used to estimate the amount of U(IV) in these samples, since there are two Oax atoms for each U(VI) atom and no Oax atoms for U(IV). The Noax values indicate that PilA− and WT contain approximately 25%, and 48% U(IV) with an estimated uncertainty of 10%. These values are consistent with U XANES measurements indicating more U(IV) in the WT sample as compared to the PilA− sample.

TABLE 11

EXAFS modeling results for R and $\sigma^2$**

| Path | CN | R (Å) | $\sigma^2$ ($\cdot 10^{-3}$ Å$^2$) |
|---|---|---|---|
| Oax | Noax | 1.80 ± 0.01 | 1* |
| Oeq | Noeq | 2.38 ± 0.02 | ** |
| C1 | Nc1 | 2.86 ± 0.01 | 2 ± 7 |
| C2 | Nc2 | 3.49 ± 0.03 | 2 ± 7 |
| Oax1-Oax2 | Noax | 3.61 ± 0.02 | 2* |
| Oax1-U-Oax2 | Noax | 3.61 ± 0.02 | 2* |
| Oax1-U-Oax1 | 2Noax | 3.61 ± 0.02 | 4* |
| C3 | Nc1 | 4.54 ± 0.07 | 2 ± 7 |
| C1-C3 | 2Nc1 | 4.54 ± 0.07 | 2 ± 7 |
| C1-C3-C1 | Nc1 | 4.54 ± 0.07 | 2 ± 7 |
| Odist | Nc2 | 4.69 ± 0.08 | 2 ± 7 |
| C2-Odist | 2Nc2 | 4.72 ± 0.08 | 2 ± 7 |
| C2-Odist-C2 | Nc2 | 4.74 ± 0.08 | 2 ± 7 |

*value held,
**PilA: 25 ± 6, WT: 18 ± 4

TABLE 12

EXAFS modeling results for coordination numbers

| Data Set | Noax | Noeq | C1 | C2 |
|---|---|---|---|---|
| PilA− | 1.5 ± 0.1 | 6.9 ± 2.2 | 1.2 ± 0.7 | 1.2 ± 0.7 |
| WT | 1.0 ± 0.1 | 6.3 ± 1.4 | 1.4 ± 0.7 | 1.4 ± 0.8 |

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

Although specific embodiments have been illustrated and described herein, it will be appreciated by those of ordinary skill in the art that any procedure that is calculated to achieve the same purpose may be substituted for the specific embodiments shown. This application is intended to cover any adaptations or variations of the present subject matter. For example, although the discussion herein has focused on removal of uranium, it is expected that other soluble metals, such as other heavy metals can also be removed with the nanowires described herein. Therefore, it is manifestly intended that embodiments of this invention be limited only by the claims and the equivalents thereof.

What is claimed is:

1. An isolated or recombinant Geobacteraceae nanowire peptide comprising a truncated nanowire peptide fused to a fusion partner peptide at the N-terminus of the nanowire peptide, wherein the truncation comprises a one to 29 amino acid truncation at the N-terminus or at the C-terminus of a nanowire peptide, and wherein the truncated nanowire peptide assembles into a conductive pilus and is electrically conductive, the nanowire peptide comprising an amino acid sequence selected from SEQ ID NO:1-10 and variants thereof.

2. The nanowire peptide of claim 1, wherein the peptide is genetically or chemically modified to modulate the conductive, adhesive, assembly or coupling properties of the nanowire peptide.

3. A pilus comprising the nanowire peptide of claim 1.

4. The nanowire peptide of claim 1, wherein the nanowire peptide is truncated at the N-terminus.

5. The nanowire peptide of claim 1, wherein the nanowire peptide is truncated at the N-terminus by 1 to 29 amino acids.

6. The nanowire peptide of claim 1, wherein the nanowire peptide is truncated at the N-terminus by 10 to 29 amino acids.

7. The nanowire peptide of claim 1, wherein the amino acid sequence of the nanowire peptide has at least 95% amino acid identity with any of SEQ ID NOS: 1-10.

8. The nanowire peptide of claim 1, wherein the truncated nanowire peptide comprises an amino acid sequence selected from SEQ ID NOS: 26-29 and variants or combinations thereof.

9. The nanowire peptide of claim 8, wherein the amino acid sequence of the truncated nanowire peptide has at least 95% amino acid identity to any of SEQ ID NOS: 26-29 or combinations thereof.

10. A method of producing nanowire peptides fused to a fusion partner peptide at the N-terminus of the nanowire peptide comprising:
expressing a fusion protein comprising a fusion partner peptide fused to the N-terminus of a nanowire peptide, wherein the fusion protein is expressed by a host cell, and the nanowire peptides comprise an isolated or recombinant Geobacteraceae nanowire peptide comprising a truncated nanowire peptide, wherein the truncation comprises a one to 29 amino acid truncation at the N-terminus or at the C-terminus of the nanowire peptide, and wherein the nanowire peptide assembles into a conductive pilus and is electrically conductive, the nanowire peptide comprising an amino acid sequence selected from SEQ ID NO:1-10 and variants thereof.

11. The method of claim 10 wherein the fusion partner peptide comprises a chitin-binding domain.

12. The method of claim 10 further comprising affinity purifying the fusion protein; and removing the fusion partner peptide from the fusion protein to allow the nanowire peptide to assemble.

13. The method of claim 12, wherein a pilin within each of the one or more conductive pili comprises a truncated nanowire peptide from Geobacteraceae bacterium wherein the truncation comprises a one to 29 amino acid truncation at an N-terminus or at a C-terminus, and wherein the polypeptide assembles into the conductive pilus.

14. The method of claim 12 wherein the conductive pili are expressed in biofilms.

15. An isolated or recombinant Geobacteraceae nanowire peptide comprising a truncated nanowire peptide fused to a fusion partner peptide comprising a chitin-binding domain (CBD) at the N-terminus of the nanowire peptide, wherein the truncation comprises a one to 29 amino acid truncation at the N-terminus or at the C-terminus of a nanowire peptide, and wherein the truncated nanowire peptide assembles into a conductive pilus and is electrically conductive, the nanowire peptide comprising an amino acid sequence selected from SEQ ID NO:1-10 and variants thereof.

* * * * *

UNITED STATES PATENT AND TRADEMARK OFFICE
CERTIFICATE OF CORRECTION

PATENT NO. : 9,601,227 B2
APPLICATION NO. : 14/193943
DATED : March 21, 2017
INVENTOR(S) : Reguera et al.

It is certified that error appears in the above-identified patent and that said Letters Patent is hereby corrected as shown below:

On the Title Page

Item (56)

Other Publications/Column 2/Line 15: Error reads as "Microbology," and should read as "Microbiology,"
Page 2/Other Publications/Column 2/Line 54: Error reads as "at at.," and should read as "et al.,"
Page 3/Other Publications/Column 1/Line 10: Error reads as "at al., "Purificaton" and should read as "et al., "Purification"
Page 3/Other Publications/Column 1/Line 45: Error reads as "Prerequisitetto" and should read as "Prerequisite to"
Page 3/Other Publications/Column 2/Line 9: Error reads as "ZP 05310612.1," and should read as "ZP_05310612.1,"
Page 3/Other Publications/Column 2/Line 12: Error reads as "at al.," and should read as "et al.,"
Page 3/Other Publications/Column 2/Line 50: Error reads as ""Genome-Wde" and should read as ""Genome-Wide"

In the Specification

Column 1/Line 26: Error reads as "or and" and should read as "and/or"
Column 2/Line 17: Error reads as "dichrosim" and should read as "dichroism"
Column 2/Line 24: Error reads as "β-D-glucopyrano side" and should read as "β-D-glucopyranoside"
Column 4/Line 66: Error reads as "ofPilA-" and should read as "of PilA-"
Column 5/Line 37: Error reads as "(C)" and should read as "(U$^+$)"
Column 8/Line 26: Error reads as "Citruline (Cit) and homocycteine" and should read as "Citrulline (Cit) and homocysteine"
Column 13/Line 65: Error reads as "intermelocular" and should read as "intermolecular"
Column 27/Line 7: Error reads as "Magnaporth" and should read as "Magnaporthe"
Column 29/Line 20-21: Error reads as "archeabacteria" and should read as "archaebacterial"

Signed and Sealed this
Sixth Day of June, 2017

Michelle K. Lee
*Director of the United States Patent and Trademark Office*

CERTIFICATE OF CORRECTION (continued)

Column 31/Line 46: Error reads as "and or" and should read as "and/or"
Column 44/Line 31: Error reads as "dichrosim" and should read as "dichroism"
Column 44/Line 32: Error reads as "dichrosim" and should read as "dichroism"
Column 44/Line 45: Error reads as "Savitsky-Golay" and should read as "Savitzky-Golay"
Column 47/Line 63: Error reads as "dichrosim" and should read as "dichroism"
Column 48/Line 7-8: Error reads as "dichrosim" and should read as "dichroism"
Column 48/Line 38: Error reads as "DICROWEB" and should read as "DICHROWEB"
Column 48/Line 52: Error reads as "NRMSD" and should read as "NMRSD"
Column 48/Line 58: Error reads as "(NRMSD)" and should read as "(NMRSD)"
Column 48/Line 64: Error reads as "NRMSD" and should read as "NMRSD"
Column 49/Line 9: Error reads as "NRMSD" and should read as "NMRSD"
Column 49-50/Line 13/Table 6: Error reads as "NRMSD" and should read as "NMRSD"
Column 49-50/Line 16/Table 6: Error reads as "NRMSD" and should read as "NMRSD"
Column 51/Line 53: Error reads as "Wycomb," and should read as "Wycombe,"
Column 54/Line 47: Error reads as "Appi." and should read as "Appl."
Column 57/Line 57: Error reads as "(PHA)" and should read as "(PilA$^-$)"
Column 57/Line 64: Error reads as "(51)" and should read as "(S1)"
Column 58/Line 39: Error reads as "Adsorption" and should read as "Absorption"
Column 61/Line 51: Error reads as "Boeckler" and should read as "Boeckeler"
Column 64/Line 13: Error reads as "lipolysaccharide" and should read as "lipopolysaccharide"